US008021650B2

(12) United States Patent
Tamareselvy et al.

(10) Patent No.: US 8,021,650 B2
(45) Date of Patent: Sep. 20, 2011

(54) POLYMERS CONTAINING SILICONE COPOLYOL MACROMERS AND PERSONAL CARE COMPOSITIONS CONTAINING SAME

(75) Inventors: Krishnan Tamareselvy, Brecksville, OH (US); Thomas Barker, Akron, OH (US); Deborah Filla, Twinsburg, OH (US); Aroop Kumar Roy, Broadview Heights, OH (US); Carol Kyer, Canal Fulton, OH (US); Denise Rafferty, Sagamore Hills, OH (US); Joseph Zellia, Barberton, OH (US); Regina Klump, Parma, OH (US)

(73) Assignee: Lubrizol Advanced Materials, Inc., Cleveland, OH (US)

( * ) Notice: Subject to any disclaimer, the term of this patent is extended or adjusted under 35 U.S.C. 154(b) by 1156 days.

(21) Appl. No.: 11/677,751

(22) Filed: Feb. 22, 2007

(65) Prior Publication Data
US 2007/0202069 A1 Aug. 30, 2007

Related U.S. Application Data

(60) Provisional application No. 60/776,852, filed on Feb. 24, 2006.

(51) Int. Cl.
*A61Q 5/12* (2006.01)
*C08F 220/12* (2006.01)
(52) U.S. Cl. ............... 424/70.12; 524/858; 556/450; 556/453; 556/462; 556/436; 556/437
(58) Field of Classification Search .......... 524/556, 524/858; 556/450, 453, 462, 436, 437, 465, 556/466; 528/29; 424/70.12
See application file for complete search history.

(56) References Cited

U.S. PATENT DOCUMENTS

| | | | |
|---|---|---|---|
| 2,798,053 | A | 7/1957 | Brown |
| 3,560,544 | A | 2/1971 | Haluska |
| 4,384,096 | A | 5/1983 | Sonnabend |
| 4,421,902 | A | 12/1983 | Chang et al. |
| 4,514,552 | A | 4/1985 | Shay et al. |
| 4,600,761 | A | 7/1986 | Ruffner et al. |
| 4,693,935 | A | 9/1987 | Mazurek |
| 4,728,571 | A | 3/1988 | Clemens et al. |
| 4,753,659 | A | 6/1988 | Bayerlein et al. |
| RE33,156 | E | 1/1990 | Shay et al. |
| 4,902,499 | A | 2/1990 | Bolish, Jr. et al. |
| 5,011,978 | A | 4/1991 | Barron et al. |
| 5,162,472 | A | 11/1992 | O'Lenick, Jr. |
| 5,292,843 | A | 3/1994 | Jenkins et al. |
| 5,294,692 | A | 3/1994 | Barron et al. |

(Continued)

FOREIGN PATENT DOCUMENTS
WO WO2004/112733 12/2004
(Continued)

OTHER PUBLICATIONS

Geroge R. Whalley, Fabric Conditioning Agents, HAPPI, pp. 55-58, Feb. 1995.

(Continued)

*Primary Examiner* — Michael M Bernshteyn
(74) *Attorney, Agent, or Firm* — Thoburn T. Dunlap

(57) ABSTRACT

Dimethicone copolyol polymers are synthesized from dimethicone copolyol macromers. Polymers containing the macromer repeating units are useful in a variety of applications including personal care, textile and industrial formulations to deliver softness, lubricity, fixative, humidity resistance, water repellency, gloss, surface modification, and surfactant properties.

24 Claims, 9 Drawing Sheets

U.S. PATENT DOCUMENTS

| | | | |
|---|---|---|---|
| 5,296,625 A * | 3/1994 | O'Lenick et al. | 556/437 |
| 5,385,999 A | 1/1995 | D'Anvers et al. | |
| 5,412,142 A | 5/1995 | Wilkerson, III et al. | |
| 5,770,760 A | 6/1998 | Robinson | |
| 6,140,435 A | 10/2000 | Zanotti-Russo | |
| 6,197,317 B1 | 3/2001 | Klein | |
| 6,403,074 B1 | 6/2002 | Blankenburg et al. | |
| 6,635,702 B1 | 10/2003 | Schmucker-Castner et al. | |
| 2003/0211051 A1 | 11/2003 | Majeti et al. | |
| 2004/0038151 A1 * | 2/2004 | Berger et al. | 430/271.1 |
| 2004/0087469 A1 * | 5/2004 | Carswell | 510/499 |

FOREIGN PATENT DOCUMENTS

| | | |
|---|---|---|
| WO | WO2004/113390 | 12/2004 |
| WO | 2007/035315 | 3/2007 |
| WO | WO 2007035315 A2 * | 3/2007 |

OTHER PUBLICATIONS

Kenneth A. Kasprzak, Volatile Silicones, Soap/Cosmetics/Chemical Specialties, pp. 40-43, Dec. 1986.

Emil G. Klarmann, Suntan Preparations, Cosmetics, Science and Technology by Segarin et al., Chapter 8, pp. 189-212.

Evaluation of Performance, Harry's Cosmeticology, Ch. 30, 8th Ed., M. J. Rieger, Ph.D. (ed.) pp. 666-667, Chemical Publishing Co., Inc., New York, NY 2000.

Diaz et al, J. Soc. Cosmet. Chem, 34, pp. 205-212, Jul. 1983.

64 Federal Register, vol. 64, No. 98, pp. 27666-27693, May 21, 1999.

Todd and Byers, Volatile Silicone Fluids for Cosmetics, Cosmetics and Toiletries, vol. 91, pp. 29-32, 1976.

* cited by examiner

POLYMERS CONTAINING SILICONE COPOLYOL MACROMERS AND PERSONAL CARE COMPOSITIONS CONTAINING SAME

RELATED U.S. APPLICATION

This application claims the benefit of priority from U.S. provisional application Ser. No. 60/776,852 filed on Feb. 24, 2006

FIELD OF THE INVENTION

The present invention relates to polymerizable dimethicone copolyol macromers containing ethylenic unsaturation and to polymers obtained therefrom. The ethylenically polymerizable macromer is formed from the reaction of a dimethicone copolyol containing terminal or pendant hydroxyl groups and itaconic anhydride. The obtained macromer is homopolymerizable or copolymerizable with ethylenically unsaturated monomers and the polymers prepared therefrom are useful in a variety of industrial, home care, and personal care applications.

BACKGROUND

A class of silicon containing polymers known as polydimethylsiloxanes is widely employed in the coatings and personal care industries. In coatings formulations, polydimethylsiloxane and its derivatives are being increasingly used for general modification of surface properties as they provide water and oil repellency, stain resistance, barrier properties, surfactant properties and lubricity. In personal care formulations, the use of polydimethylsiloxane and derivatives thereof, particularly dimethicone copolyols, has gained wide acceptance for the latter's surfactant characteristics and positive effect on sensory properties of a given composition.

Attempts to improve the physical properties of such formulations by incorporating dimethicone copolyols into the composition have met with limited success. These polydimethylsiloxane derivatives were frequently incompatible with the polar polymers and/or other ingredients typically contained in coatings and personal care compositions. Often times auxiliary additives have to be employed to compatibilize the polydimethylsiloxane derivative and the anionic and cationic polymers typically used in the coatings and personal care industries to prevent phase separation of the key components during extended storage periods.

Accordingly, efforts have been made to covalently incorporate the polydimethylsiloxane derivatives into the target polymer backbone in an effort to compatibilize the silicone and polymer components of the formulation. U.S. Pat. No. 6,403,074 discloses a silicone containing polymer obtained by polymerizing ethylenically unsaturated monomers in the presence of dimethicone copolyol via a free radical mechanism. The patent disclosure surmises that grafting of the monomers onto the dimethicone copolyol occurs during the polymerization reaction. However, it is not evident from the disclosure to what extent (if any) that the dimethicone copolyol is covalently incorporated into the polymer backbone or whether an interpolymer of the dimethicone copolyol and the free radically polymerized monomers is formed. For polyhydroxy carbinol compounds, chain transfer can often be a significant problem during free radical polymerization, and this may prevent effective copolymerization of such compounds with other ethylenically unsaturated monomers.

In another approach, silicone containing macromers containing terminal unsaturation have been synthesized via the anionic polymerization of hexamethylcylotrisiloxane monomer (D3) to from a living polymer of controlled molecular weight. Termination of the anionic polymerization reaction is achieved via the direct reaction of the living polymeric anion with halogen-containing termination agents, such as, chlorosilane compounds containing a polymerizable vinyl group. The obtained vinyl terminated siloxane containing macromers in turn can be polymerized with other copolymerizable unsaturated monomers to obtain silicone containing copolymers as disclosed in U.S. Pat. Nos. 4,693,935 and 4,728,571. However, the synthesis of these macromers is very difficult and given the relatively high molecular weight of the macromer it is arduous to separate the unreacted impurities from the reaction product.

In U.S. Pat. No. 5,162,472, there is disclosed a vinyl terminated dimethicone copolyol macromer that is prophetically reported to be synthesized by esterifying acrylic acid with a hydroxyl terminated dimethicone copolyol. The reaction mass is heated to 140 to 180° C. and the disclosure states that the purportedly obtained vinyl containing silicone ester is subsequently copolymerized without additional purification. As is well known the esterification of carboxylic acid with an alcohol is a slow reaction with moderate yields for oligomeric or polymeric substrates. Further, is also well known in the art of acrylic acid chemistry that this highly reactive monomer spontaneously dimerizes at room temperatures via a thermally induced ionic mechanism wherein the proton dissociates from the carboxylic acid group forming a carboxylate anion which subsequently adds to acrylic acid via Michael-type addition to give the dimer. This phenomenon is substantially accelerated at increasing temperatures. At the reaction temperatures reported in the '472 disclosure the acrylic acid starting material would rapidly dimerize consuming most if not all of this reactant to yield a complex mixture of products. Given that the esterification of a carboxylic acid with an alcohol is slow and that acrylic acid rapidly oligomerizes at the reaction temperatures reported in the '472 disclosure, it is difficult to perceive how the purported product is obtained. Even if some product is formed it would be difficult, time consuming and costly to separate the desired product from the reaction mass.

A more traditional esterification procedure for functionalizing a dimethicone copolyol with a vinyl end group is to react an acid chloride such as acryloyl chloride with the dimethicone copolyol and employing a base to remove the liberated HCl. The use of the acryloyl chloride eliminates the spontaneous oligomerization issues suffered from the use of acrylic acid as set forth in the '472 disclosure. However, a salt is generated as a by-product of the esterification reaction. Salts are not only difficult to remove from macromers but may also be deleterious to the subsequent polymerization of the macromer.

In addition to the problems faced in synthesizing the foregoing macromers, the polymerization activities of these acrylate-type macromers are similar to the polymerization activities of the comonomers intended for copolymerization into the polymer backbone due to the unhindered nature of the carbon-carbon unsaturation in the terminal vinyl group. It is common practice to vary monomer reactivity as one approach to altering the copolymer structure and thereby the latter's physical and chemical properties.

Accordingly, there is a need for newer silicone containing macromers that are easily synthesized and purified and exhibit polymerization activities that allow flexibility in copolymerization to generate copolymers with desirable properties. We have now unexpectedly discovered such a silicone macromer via a reaction originally intended to prepare readily polymerizable compounds containing the itaconate moiety.

The present invention provides dimethicone copolyol macromers that are easily synthesized and that have unexpected polymerization activities which allow ready copolymerization to generate products with desirable properties. The copolyol macromers of the invention are synthesized from the reaction of a dimethicone copolyol and itaconic anhydride. Dimethicone copolyols contain terminal or pendant polyether groups that terminate in an active hydroxyl group. The reaction of a hydroxy silicone compound such as dimethicone copolyol with a cyclic anhydride is known. As disclosed in U.S. Pat. Nos. 3,560,544 and 5,296,625 the reaction of the active hydroxyl group(s) on the copolyol with the anhydride yields the copolyol half-ester of the anhydride. While these patents disclose the reaction of a dimethicone copolyol with a variety of cyclic anhydrides (including the olefinically unsaturated maleic anhydride), the use of anhydrides containing exocylic olefinic unsaturation is not described or suggested. Moreover, the '544 patent mentions that the derivatized silicone polymer is used as a surfactant, a wetting agent, detergent, emulsifier or fiber lubricant, and the '625 disclosure teaches that the obtained esters are useful in textile and personal care applications to render softness and lubrication to treated substrates. There is no teaching or suggestion in any of these disclosures that the reaction product of a hydroxy silicone with an anhydride containing any type of unsaturation can be employed as polymerizable macromer in the synthesis of polymers and copolymers.

Unexpectedly, it has been discovered that the half-ester formed from the reaction of itaconic anhydride (containing exocylic unsaturation) with a dimethicone copolyol yields a mixture of various isomers of citraconate mono-esters formed from the rapid isomerization itaconic anhydride to citraconic anhydride and subsequent reaction of the citraconic anhydride with the silicone copolyol. More surprisingly, given that the olefinic double bond in the citraconate moiety of the so-formed macromer is sterically encumbered by triple substitution, and the well known fact that trisubstituted olefins do not readily free radically polymerize at useful rates, we have found the citraconate dimethicone copolyol esters are easily copolymerized with a variety of monomers containing free radically polymerizable olefinic unsaturation. This is a novel and unexpected finding in the preparation of ethylenically unsaturated silicone copolyol esters. Itaconic anhydride is known to react with alcohols to generate the expected itaconate esters.

DESCRIPTION OF EXEMPLARY EMBODIMENTS

Figure 1:
FIG. 1 is a photograph of a Caucasian hair mannequin head in which one half of the head is styled with a hair fixative composition containing a polymer of the invention and the other half of the head is styled with a control fixative composition. The photograph is taken before humidity chamber exposure.

The dimethicone copolyol macromers of the present invention are obtained from the isomerization of itaconic anhydride and the subsequent esterification of isomerization products with a hydroxy containing dimethicone copolyol. Itaconic anhydride contains exocylic unsaturation as set forth in the structure below:

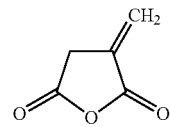

The exocyclic unsaturation is depicted as the carbon-carbon double bond between the ring carbon atom and the alkylidene, e.g., methylene, group.

In the reaction medium comprising a dimethicone copolyol (DMC-OH) and itaconic anhydride, the itaconic anhydride nearly instantaneously isomerizes to citraconic anhydride which then reacts with the copolyol to give the citraconate dimethicone copolyol ester (and the regio- and stereo isomers thereof). Minor amounts of the regio-isomers of itaconate esters are also formed. An illustrative general reaction scheme is as follows:

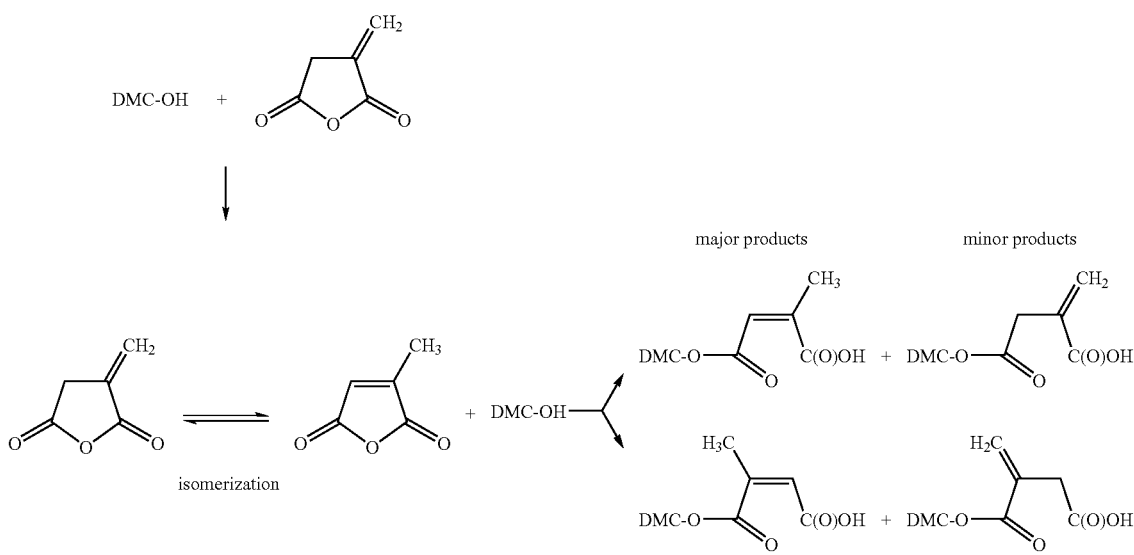

Minor amounts (less than 10 wt. % of the total ester formed) of the itaconate ester are formed due to an equilibrium between the citraconic anhydride and itaconic anhydride.

It is to be noted that the dimethicone copolyol represented by DMC-OH contains one or more anhydride reactive hydroxyl groups that can be located at a terminal end(s) of the dimethicone backbone or can be located as part of one or more pendant groups on the dimethicone backbone. Representative dimethicone copolyols are set forth under Formulae I and II below.

The esterification reaction can be carried out with or without a catalyst. When conducting the esterification reaction without catalyst the reaction mixture is heated to reaction temperatures of about 75° C. to about 90° C. The reaction can be run with either a stoichiometric amount of the dimethicone copolyol (based on the OH number) and the anhydride, or a slight excess of either reactant. In one embodiment of the invention, the amount of anhydride loading to dimethicone copolyol in the reaction mixture ranges between 0.1 equivalent to 1 equivalent based on the OH number of the dimethicone copolyol. In another embodiment the loading of anhydride to dimethicone copolyol is between 0.25 equivalent to 0.75 equivalent based on the OH number of the copolyol, and in still another embodiment the loading is between 0.5 equivalent to 0.75 equivalent. The reaction can be carried out from 1 to 3 hours. The reaction is conducted under an inert atmosphere such as a nitrogen blanket and can be carried out in a suitable solvent.

When carrying out the reaction in the presence of an esterification catalyst, the reaction rates are significantly accelerated. Standard esterification catalysts can be used at concentrations of between 0.05% to 0.50% based on the weight of the anhydride and the dimethicone copolyol in the reaction mixture. Suitable esterification catalysts include but are not limited to sulfuric acid, elemental tin, elemental zinc, elemental titanium, organo titanate compounds, organo tin compounds, organo zinc compounds, zinc oxide, magnesium oxide, calcium oxide, stannous oxide, and the alkali metal acetates such as sodium acetate and potassium acetate. Reaction temperatures can range from ambient room temperature to about 90° C. Typically ambient room temperature ranges from about 20° C. to about 26° C. All other reaction conditions are as above for the non-catalyzed reactions.

In another embodiment of the invention, citraconic anhydride which has methyl substitution on the double bond can be used in lieu of itaconic anhydride in the esterification reaction.

In one embodiment of the invention the dimethicone copolyol suitable for the esterification reaction contains a terminal hydroxy end group(s) and can be represented by Formula I below:

Formula I

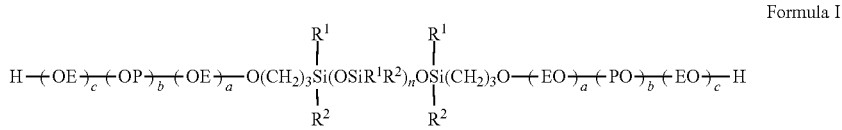

wherein $R^1$ and $R^2$ independently represent a radical selected from $C_1$ to $C_{30}$ alkyl, $C_1$ to $C_{20}$ halo substituted alkyl (e.g., $-CCl_3$, $-CBr_3$, $CF_3$), $C_3$ to $C_8$ cycloalkyl, $C_6$ to $C_{14}$ aryl, and $C_2$ to $C_{20}$ alkenyl; E represents a divalent ethylene radical ($-CH_2CH_2-$); P independently represents a divalent propylene radical ($-CH_2CH(CH_3)-$) or ($-CH_2CH_2CH_2-$); a, b, and c are independently 0 to 100; and n is 0 to 200. E taken together with the oxygen atom to which is attached represents an ethylene oxide residue (EO or OE) and P taken together with the oxygen atom to which it is attached represents a propylene oxide residue (PO or OP). The EO/PO residues can be arranged in random, non-random, or blocky sequences. As used here and throughout the specification the terms halogen and halo include but are not limited to bromo, chloro, and fluoro.

Exemplary $R^1$ and $R^2$ radicals include but are not limited to methyl, ethyl, propyl, butyl, pentyl, hexyl, cyclopentyl, cyclohexyl, phenyl, vinyl, and allyl. Each of the foregoing radicals as well as the generic $R^1$ and $R^2$ radicals set forth above are optionally substituted with $C_1$ to $C_5$ alkyl, halogen, and halo($C_1$ to $C_5$)alkyl (e.g., —$CCl_3$, —$CBr_3$, $CF_3$).

In one embodiment of the invention the dimethicone copolyol suitable for the esterification reaction contains a pendant hydroxy group(s) and can be represented by Formula II below:

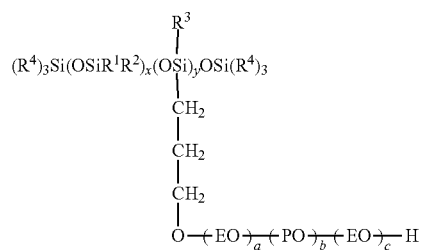

Formula II wherein $R^3$ represents a radical selected from $C_1$ to $C_{30}$ alkyl, halo($C_1$ to $C_{20}$) alkyl (e.g., —$CCl_3$, —$CBr_3$, $CF_3$), $C_3$ to $C_8$ cycloalkyl, $C_6$ to $C_{14}$ aryl, and $C_2$ to $C_{20}$ alkenyl; $R^4$ independently represents a radical selected from $C_1$ to $C_{30}$ alkyl, $C_6$ to $C_{14}$ aryl, and $C_2$ to $C_{20}$ alkenyl; EO (OE) and PO(OP) represent ethylene oxide and propylene oxide residues as previously defined; a, b, and c are independently 0 to 100; x is 0 to 200; and y is 1 to 200. The EO/PO residues can be arranged in random, non-random, or blocky sequences.

Exemplary $R^3$ radicals include but are not limited to methyl, ethyl, propyl, butyl, pentyl, hexyl, cyclopentyl, cyclohexyl, phenyl, vinyl, and allyl. Each of the foregoing radicals as well as the generic $R^3$ radicals described above are optionally substituted with $C_1$ to $C_5$ alkyl, halogen, and halo ($C_1$ to $C_{20}$) alkyl (e.g., —$CCl_3$, —$CBr_3$, $CF_3$).

Exemplary $R^4$ radicals include but are not limited to methyl, phenyl, and vinyl. Each of the foregoing radicals as well as the generic $R^4$ radicals described above are optionally substituted with $C_1$ to $C_5$ alkyl, halogen, and halo($C_1$ to $C_{20}$) alkyl (e.g., —$CCl_3$, —$CBr_3$, $CF_3$).

Exemplary dimethicone copolyol reactant materials suitable for the esterification are disclosed in U.S. Pat. Nos. 5,136,063 and 5,180,843, the disclosures of which are incorporated herein by reference. In addition, dimethicone copolyols are commercially available under the Silsoft® and Silwet® brand names from the General Electric Company (GE-OSi). Specific product designations include but are not limited to Silsoft 305, 430, 475, 810, 895, Silwet L 7604 (GE-OSi) and DC 5103 (Dow Corning Corporation).

An exemplary reaction scheme illustrating the esterification of a dimethicone copolyol of Formula I is as follows:

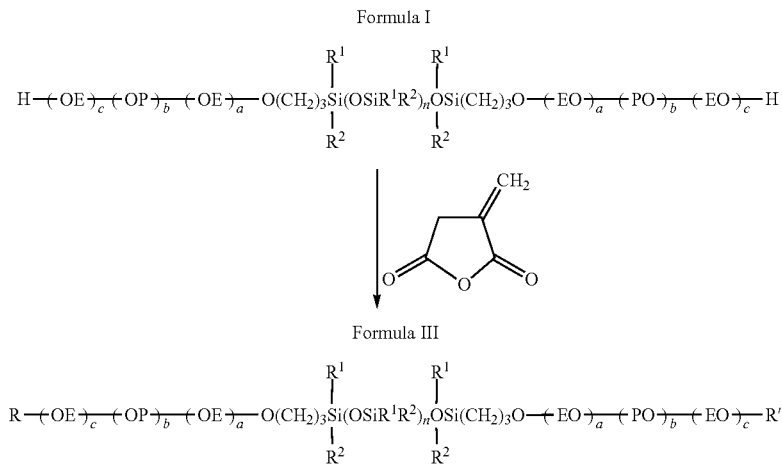

wherein R and R' independently represent hydrogen and a cyclic anhydride residue (half ester) represented by the formulae:

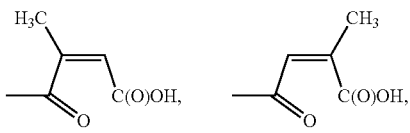

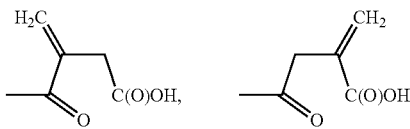

and all isomers thereof; subject to the proviso that R and R' can not both be hydrogen at the same time; and $R^1$, $R^2$, EO, OE, PO, OP, a, b, c, and n are as previously defined. The reaction product represented by Formula III will contain a mixture of dimethicone copolyol citraconates and itaconates including the regio— and stereo isomers thereof (isomers).

An exemplary reaction scheme illustrating the esterification of a dimethicone copolyol of Formula II is as follows:

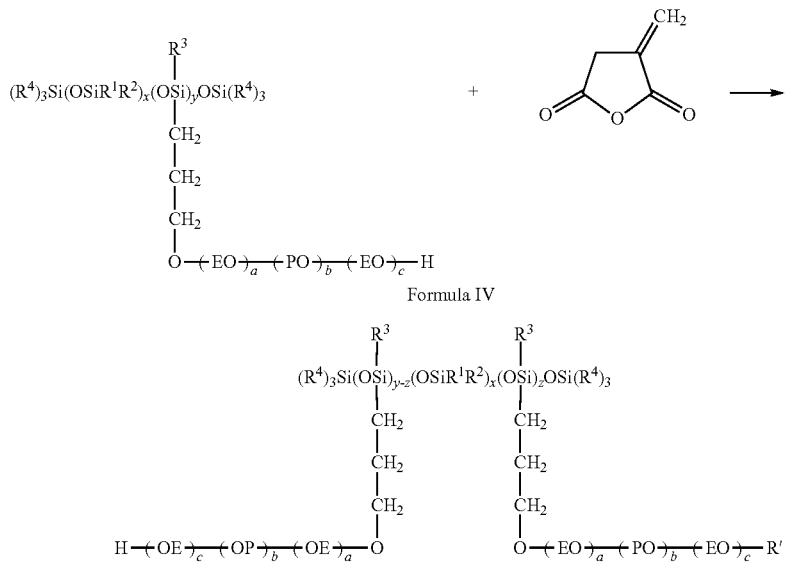

Formula II / Formula IV wherein R' is a cyclic anhydride residue as previously defined, and, $R^1, R^2, R^3, R^4$, EO, (OE), PO, (OP), a, b, c, x and y are as previously defined, and z is $\leq y$. The reaction product represented by Formula IV will contain a mixture of dimethicone copolyol citraconates (in major portion) and itaconates (in minor portion) including the isomers thereof.

Surprisingly, it has been discovered that the dimethicone copolyol citraconates of Formulae III and IV wherein the R and R' groups contain olefinic unsaturation are readily polymerizable. It has also been found that the half esters formed from dimethicone copolyols and maleic anhydride are also polymerizable with a variety of copolymerizable monomers.

In one embodiment of the present invention the polymerizable dimethicone copolyol macromers conform to the following structures:

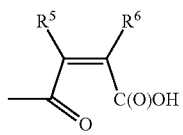

wherein $R^5$ and $R^6$ are defined as above. In one embodiment at least one of $R^5$ and $R^6$ in the formulae above is methyl.

In one embodiment of the invention, the dimethicone copolyol macromers set forth under Formulae III, IIIa, IV, and IVa are free radically polymerizable. The copolyol macromers are homopolymerizable and can be employed as building blocks to create a star-like, comb-like, brush-like,

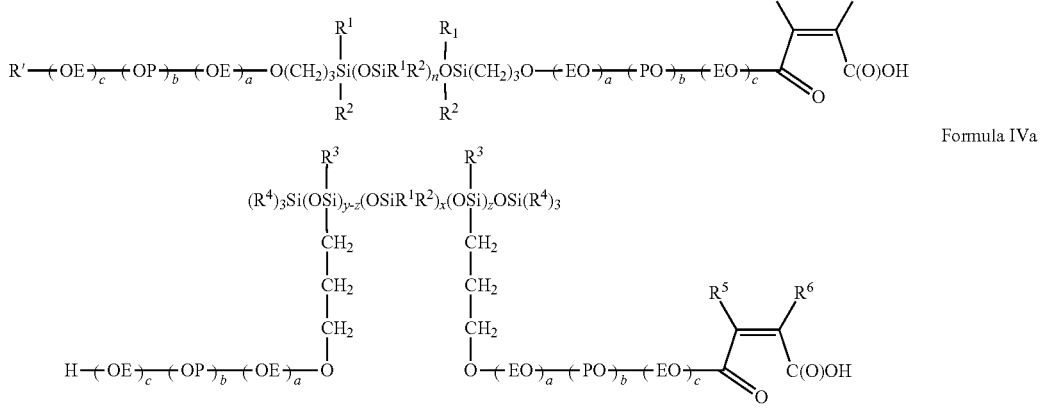

Formula IIIa / Formula IVa wherein $R^1, R^2, R^3, R^4$, EO (OE), PO(OP), a, b, c, n, x, y and z are as previously defined; $R^5$ and $R^6$ are independently selected from hydrogen and methyl, subject to the proviso that $R^5$ and $R^6$ can not both represent methyl at the same time; and R' represents hydrogen or a radical represented by the structure:

and/or flower-like polymers) or are copolymerizable and can be utilized as building blocks to design well-defined structure like arms, branches, rakes, combs graft copolymers) with ethylenically unsaturated free radically polymerizable monomers. By ethylenically unsaturated is meant that the monomer possesses at least one polymerizable carbon-carbon double bond. The macromers of this invention can be employed in the synthesis of polymers to convey properties inherent to dimethicone copolyols to a particular polymer backbone. Such polymers can be used in personal care, textile and industrial formulations to deliver softness, lubricity, sensory, fixative, conditioning, water repellency, gloss, surface, and solubility properties, to name a few.

In one embodiment, the polymers of the invention can be polymerized from a monomer mixture comprising (on a total monomer weight basis): (a) about 0.1 to 100 wt. % of at least one dimethicone copolyol macromer selected from Formulae II, IIIa, IV and IVa above; (b) 0 to 99.9 wt. % of a non-ionic monomer; (c) 0 to 99.9 wt. % of at least an acidic vinyl monomer; (d) 0 to 99.9 wt. % of at least one cationic vinyl monomer; (e) 0 to 99.9 wt. % of at least one associative vinyl monomer; (f) 0 to 99.9 wt. % of at least one semihydrophobic vinyl monomer; and (g) 0 to 5 wt. % of a crosslinking monomer. The amount and selection of each monomer employed in the polymerizable monomer mixture will depend on the desired properties of the polymer product. Suitable monomers that are copolymerizable with the dimethicone copolyol macromers are described below. While overlapping weight ranges for the various monomer components that make up the polymerizable monomer mixture have been expressed for selected embodiments of the invention, it should be readily apparent that the specific amount of each monomer component in the monomer mixture will be selected from its disclosed range such that the desired amount of each monomer will be adjusted so that the sum of all monomer components in the polymerizable monomer mixture will total 100 wt. %.

The polymers can optionally be prepared from a monomer mixture comprising one or more chain transfer agents, which are well known in the polymer arts.

The terms "halogen-substituted", "hydroxy-substituted", "carboxy-substituted", "polyoxyalkylene-substituted", "alkyl-substituted", and "aryl-substituted" as used herein in reference to alkyl or aryl groups, and the like, mean that at least one hydrogen atom on an alkyl, aryl, or like group has been replaced by at least one halogen atom, hydroxyl group, carboxyl group, polyoxyalkylene group, alkyl group, or aryl group, respectively. As used herein, the terms "(meth)acrylic" acid, "(meth)acrylate", and "(meth)acrylamide" are meant to include the corresponding methyl derivatives of acrylic acid, alkyl acrylate, and acrylamide. For example, "(meth)acrylic" acid refers to acrylic acid and/or methacrylic acid, "(meth)acrylate" refers to alkyl acrylate and/or alkyl methacrylate, and "(meth)acrylamide" refers to acrylamide and/or methacrylamide derivatives.

Nonionic Vinyl Monomer

Nonionic vinyl monomers suitable for use in the present invention are copolymerizable, nonionic, ethylenically unsaturated monomers, which are well known in the art. In one embodiment the nonionic monomers are compounds having either of the following Formulae:

$$CH_2=C(X)Z, \quad (V)$$

$$CH_2=CH-OC(O)R^7; \quad (VI)$$

wherein, in each of formulas (V) and (VI), X is H or methyl; and Z is $-C(O)OR^8$, $-C(O)NH_2$, $-C(O)NHR^8$, $-C(O)N(R^8)_2$, $-C_6H_4R^8$, $-C_6H_4OR^8$, $-C_6H_4Cl$, $-C_6H_{11}$, $-C_6H_7(R^8)(R^8)(R^8)$ (e.g., tri-substituted cyclohexyl), $-CN$, $-NHC(O)CH_3$, $-NHC(O)H$, N-(2-pyrrolidonyl), N-caprolactamyl, $-C(O)NHC(CH_3)_3$, $-C(O)NHCH_2CH_2-$N-ethyleneurea, $-Si(R^7)_3$, $-C(O)O(CH_2)_xSi(R^7)_3$, $-C(O)NH(CH_2)_xSi(R^7)_3$, or $-(CH_2)_xSi(R^7)_3$; x is an integer in the range of 1 to about 6; each $R^7$ is independently linear and branched $C_1$ to $C_{18}$ alkyl; each $R^8$ is independently linear and branched $C_1$ to $C_{30}$ alkyl, hydroxy-substituted $C_2$ to $C_{30}$ alkyl, or halogen-substituted $C_1$ to $C_{30}$ alkyl.

Non limiting examples of suitable nonionic monomers include $C_1$ to $C_{30}$ alkyl (meth)acrylates; cyclohexyl(meth)acrylates; 3,3,5-trimethylcyclohexyl(meth)acrylates (TMCHMA); $C_1$ to $C_{30}$ alkyl (meth)acrylamides; styrene; substituted styrenes, such as vinyl toluene (e.g., 2-methyl styrene), butyl styrene, isopropyl styrene, p-chloro styrene, and the like; vinyl esters, such as vinyl acetate, vinyl butyrate, vinyl caprolate, vinyl pivalate, vinyl neodecanoate, and the like; unsaturated nitriles, such as methacrylonitrile, acrylonitrile, and the like; and unsaturated silanes, such as trimethylvinylsilane, dimethylethylvinylsilane, allyldimethylphenylsilane, allyltrimethylsilane, 3-acrylamidopropyltrimethylsilane, 3-trimethylsilylpropyl methacrylate, and the like. Non limiting examples of suitable water soluble nonionic monomers are $C_1$ to $C_6$ hydroxyalkyl (meth)acrylates, such as 2-hydroxyethyl methacrylate (HEMA), 2-hydroxyethyl acrylate (2-HEA), 3-hydroxypropyl acrylate; glycerol mono(meth)acrylate; tris(hydroxymethyl)ethane mono(meth)acrylate; pentaerythritol mono(meth)acrylate; N-hydroxymethyl (meth)acrylamide; 2-hydroxyethyl (meth)acrylamide; 3-hydroxypropyl (meth)acrylamide; (meth)acrylamide; t-octyl (meth)acrylamide; N-(2,3-dihydroxypropyl)acrylamide; t-butyl(meth)acrylamide; N-vinyl caprolactam; N-vinyl pyrrolidone; methacrylamidoethyl-N-ethyleneurea (e.g., $CH_2=C(CH_3)C(O)NHCH_2CH_2-$N-ethyleneurea), $C_1$ to $C_4$ alkoxy-substituted (meth)acrylates and (meth)acrylamides, such as methoxyethyl (meth)acrylate, 2-(2-ethoxyethoxy)ethyl (meth)acrylate, and the like; and combinations thereof.

Other useful nonionic vinyl monomers include allyl alcohol, glycerol monoallyl ether, 3-methyl-3-buten-1-ol, and vinyl alcohol precursors and equivalents, such as vinyl acetate.

Acidic Vinyl Monomer

The acidic vinyl monomers suitable for use in the present invention are acidic, polymerizable, ethylenically unsaturated monomers preferably containing at least one carboxylic acid, sulfonic acid group, or a phosphonic acid group to provide an acidic or anionic functional site. These acid groups can be derived from monoacids or diacids, anhydrides of dicarboxylic acids, monoesters of diacids, and salts thereof.

Suitable acidic vinyl carboxylic acid-containing monomers include, but are not limited to acrylic acid, methacrylic acid, itaconic acid, citraconic acid, maleic acid, fumaric acid, crotonic acid, aconitic acid, and the like, and $C_1$ to $C_{18}$ alkyl-monoesters of maleic, fumaric, itaconic, or aconitic acid, such as methyl hydrogen maleate, monoisopropyl maleate, butyl hydrogen fumarate, and the like. Anhydrides of dicarboxylic acids, such as maleic anhydride, itaconic anhydride, citraconic anhydride, and the like can also be utilized as acidic vinyl monomers. Such anhydrides generally hydrolyze to the corresponding diacids upon prolonged exposure to water, or at elevated pH.

Suitable sulfonic acid group-containing monomers include, but are not limited to vinyl sulfonic acid, 2-sulfoethyl methacrylate, styrene sulfonic acid, 2-acrylamido-2-methylpropane sulfonic acid (AMPS), allyloxybenzene sulfonic acid, and the like. Particularly preferred are the sodium salt of styrene sulfonic acid (SSSA) and AMPS.

Non limiting examples of suitable phosphonic acid group-containing monomers include vinyl phosphonic acid, allyl phosphonic acid, 3-acrylamidopropyl phosphonic acid, and the like.

Suitable salts include, without limitation thereto, alkali metal salts, such as sodium, potassium and lithium salts; alkaline earth metal salts, such as calcium and magnesium salts; ammonium salts; and alkyl-substituted ammonium salts, such as salts of 2-amino-2-methyl-1-propanol (AMP), ethanolamine, diethanolamine, triethanolamine, triethylamine, and the like.

The foregoing monomers or salts thereof can be used as the acidic vinyl monomer component in mixtures of two or more.

Cationic Vinyl Monomer

Cationic vinyl monomers suitable for copolymerization are basic, polymerizable, ethylenically unsaturated monomers preferably containing at least one amino functional group. These basic amino groups can be derived from mono-, di- or poly-amino alkyl groups or nitrogen containing heteroaromatic groups. The amino group can comprise primary, secondary or tertiary amines. The monomers can be used in the amino form or in the salt form, as desired.

Non limiting examples of suitable cationic monomers can be selected from: a mono-($C_1$ to $C_4$)alkylamino($C_1$ to $C_8$)alkyl (meth)acrylate, a di-($C_1$ to $C_4$)alkylamino($C_1$ to $C_8$)alkyl (meth)acrylate, a mono-($C_1$ to $C_4$)alkylamino($C_1$ to $C_8$)alkyl (meth)acrylamide, a di-($C_1$ to $C_4$)alkylamino($C_1$ to $C_8$)alkyl (meth)acrylamide, a nitrogen-containing heterocyclic (meth)acrylamide, a nitrogen-containing heterocyclic (meth)acrylate, and mixtures thereof.

Specific examples of suitable cationic monomers include, but are not limited to 2-(N,N-dimethylamino)ethyl (meth)acrylate (DMAEMA), 3-(N,N-dimethylamino)propyl (meth)acrylate, 4-(N,N-dimethylamino)butyl (meth)acrylate, (N,N-dimethylamino)-t-butyl(meth)acrylate, 2-(tert-butylamino)ethyl(meth)acrylate (TBAEMA), 2-(N,N-diethylamino) ethyl (meth)acrylate (DEAEMA), 3-(N,N-diethylamino) propyl(meth)acrylate, 2-(N,N-dimethylamino)neopentyl acrylate (DMANPA), 4-(N,N-diethylamino)butyl(meth) acrylate, 2-(N,N-dipropylamino)ethyl (meth)acrylate, 3-(N,N-dipropylamino)propyl (meth)acrylate, 4-(N,N-dipropylamino)butyl (meth)acrylate, 3-(N,N-dimethylamino)propyl (meth)acrylate, 2-(4-morpholinyl)ethyl(meth)acrylate, 2-(4-morpholinyl)ethyl acrylate, N'-(2-N,N-dimethylamino)ethyl (meth)acrylamide, 2-(N,N-dimethylamino)propyl(meth) acrylamide (DMAPMAm), N'-(3-N,N-dimethylamino) propyl (meth)acrylamide, N-(2-pyridyl)acrylamide, N-(2-imidazoyl)(meth)acrylamide, N-(4-morpholinyl) (meth) acrylamide, N-(4-morpholinyl)acrylamide, 2-vinyl pyridine, 4-vinyl pyridine, N-vinyl-2-methylimidazole, N-vinylimidazole, N-vinyl-4-methylimidazole, and N-vinyloxazolidone, and mixtures thereof.

Suitable salt forms of the cationic monomers include, but are not limited to, mineral acid salts such as the hydrochloride, sulfate, $C_1$ to $C_{30}$ alkyl sulfate and phosphate salts; and organic acid salts such as the acetate, maleate, and fumarate salts; and the like.

Non limiting examples of salt forms of the cationic monomers include, but are not limited to, 3-trimethylammonium propyl methacrylamide chloride, 3-trimethylammonium propyl acrylamide chloride, quaternized N,N-dimethylaminoethyl methacrylate using $C_1$ to $C_{30}$ alkyl sulphate, quaternized N,N-dimethylaminoethyl methacrylate using methylchloride, quaternized vinyl imidazole, methacryloyl ethyl betaine, and methacryloyl N-oxide.

Associative Vinyl Monomer

Associative vinyl monomers (hydrophobic monomer) suitable for use in the synthesis of the polymers are compounds having an ethylenically unsaturated end group portion (i) for addition polymerization with the other monomers of the mixture; a polyoxyalkylene midsection portion (ii) for imparting selective hydrophilic properties to the product polymer and a hydrophobic end group portion (iii) for providing selective hydrophobic properties to the polymer.

The portion (i) supplying the ethylenically unsaturated end group preferably is derived from an ethylenically unsaturated mono or di-carboxylic acid or the anhydride thereof, more preferably a $C_3$ or $C_4$ mono- or di-carboxylic acid or the anhydride thereof. Alternatively, portion (i) of the associative monomer can be derived from an allyl ether or vinyl ether; a nonionic vinyl-substituted urethane monomer, such as disclosed in U.S. Reissue Pat. No. 33,156 or U.S. Pat. No. 5,294,692; or a vinyl-substituted urea reaction product, such as disclosed in U.S. Pat. No. 5,011,978; the relevant disclosures of each are incorporated herein by reference.

The midsection portion (ii) is preferably a polyoxyalkylene segment of about 5 to about 250, more preferably about 10 to about 120, and most preferably about 15 to about 60 repeating $C_2$ to $C_7$ alkylene oxide units. Preferred midsection portions (ii) include polyoxyethylene, polyoxypropylene, and polyoxybutylene segments comprising about 5 to about 150, more preferably about 10 to about 100, and most preferably about 15 to about 60 ethylene, propylene or butylene oxide units, and random or non-random sequences of ethylene oxide, propylene oxide and or butylene oxide units.

The hydrophobic end group portion (iii) of the associative monomers is preferably a hydrocarbon moiety belonging to one of the following hydrocarbon classes: a $C_8$ to $C_{40}$ linear alkyl, an aryl-substituted $C_2$ to $C_{40}$ alkyl, a $C_2$ to $C_{40}$ alkyl-substituted phenyl, a $C_8$ to $C_{40}$ branched alkyl, a $C_8$ to $C_{40}$ carbocyclic alkyl; and a $C_8$ to $C_{80}$ complex ester. Complex esters are formed by the esterification of a polyol with a long chained hydroxy acid which contains both a hydroxyl group and a carboxylic group. The carboxylic group of the long chained hydroxy acid reacts with at least one hydroxyl group of the polyol. In turn the hydroxyl group of the long chained hydroxy acid reacts with a carboxylic group of another long chained hydroxy acid and/or another long chained carboxylic acid. By long chained is meant that the hydroxy acid and the carboxylic acid contain from about 10 to 30 carbon atoms. The carbon chain can be saturated or unsaturated. Exemplary non-limiting examples of a suitable polyol are glycerol, sorbitol, pentaerythritol, trimethylol propane. An exemplary non-limiting example of a hydroxy acid is 12-hydroxy steric acid. Exemplary non-limiting long chain carboxylic acids are those that are the fatty acids derived from the vegetable oils and fatty acids set forth herein.

Non limiting examples of suitable hydrophobic end group portions (iii) of the associative monomers are linear or branched alkyl groups having about 8 to about 40 carbon atoms such as capryl ($C_8$), isooctyl (branched $C_8$), decyl ($C_{10}$), lauryl ($C_{12}$), myristyl ($C_{14}$), cetyl ($C_{16}$), cetearyl ($C_{16}$ to $C_{18}$), stearyl ($C_{18}$), isostearyl (branched $C_{18}$), arachidyl ($C_{20}$), behenyl ($C_{22}$), lignoceryl ($C_{24}$), cerotyl ($C_{26}$), montanyl ($C_{28}$), melissyl ($C_{30}$), lacceryl ($C_{32}$), and the like.

Examples of linear and branched alkyl groups having about 8 to about 40 carbon atoms that are derived from a natural source include, without being limited thereto, alkyl groups derived from hydrogenated peanut oil, soybean oil and canola oil (all predominately $C_{18}$), hydrogenated tallow oil ($C_{16}$ to $C_{18}$), and the like; and hydrogenated $C_{10}$ to $C_{30}$ terpenols, such as hydrogenated geraniol (branched $C_{10}$), hydrogenated farnesol (branched $C_{15}$), hydrogenated phytol (branched $C_{20}$), and the like.

Non limiting examples of suitable $C_2$ to $C_{40}$ alkyl-substituted phenyl groups include octylphenyl, nonylphenyl, decylphenyl, dodecylphenyl, hexadecylphenyl, octadecylphenyl, isooctylphenyl, sec-butylphenyl, and the like.

Suitable $C_8$ to $C_{40}$ carbocylic alkyl groups include, without being limited thereto, groups derived from sterols from animal sources, such as cholesterol, lanosterol, 7-dehydrocholesterol, and the like; from vegetable sources, such as phytosterol, stigmasterol, campesterol, and the like; and from yeast sources, such as ergosterol, mycosterol, and the like. Other carbocyclic alkyl hydrophobic end groups useful in the present invention include, without being limited thereto, cyclooctyl, cyclododecyl, adamantyl, decahydronaphthyl, and groups derived from natural carbocyclic materials such as pinene, hydrogenated retinol, camphor, isobornyl alcohol, and the like.

Exemplary aryl-substituted $C_2$ to $C_{40}$ alkyl groups include, without limitation thereto, styryl (e.g., 2-phenylethyl), distyryl (e.g., 2,4-diphenylbutyl), tristyryl (e.g., 2,4,6-triphenylhexyl), 4-phenylbutyl, 2-methyl-2-phenylethyl, tristyrylphenolyl, and the like.

Non limiting examples of suitable $C_8$ to $C_{80}$ complex esters include hydrogenated castor oil (predominately the triglyceride of 12-hydroxystearic acid); 1,2-diacyl glycerols such as 1,2-distearyl glycerol, 1,2-dipalmityl glycerol, 1,2-dimyristyl glycerol, and the like; di-, tri-, or poly-esters of sugars such as 3,4,6-tristearyl glucose, 2,3-dilauryl fructose, and the like; and sorbitan esters such as those disclosed in U.S. Pat. No. 4,600,761 to Ruffner et al., the pertinent disclosures of which are incorporated herein by reference.

Useful associative monomers can be prepared by any method known in the art. See, for example, U.S. Pat. No. 4,421,902 to Chang et al.; No. 4,384,096 to Sonnabend; No. 4,514,552 to Shay et al.; No. 4,600,761 to Ruffner et al.; No. 4,616,074 to Ruffner; No. 5,294,692 to Barron et al.; No. 5,292,843 to Jenkins et al.; No. 5,770,760 to Robinson; and No. 5,412,142 to Wilkerson, III et al.; the pertinent disclosures of which are incorporated herein by reference.

Examples of associative vinyl monomers include those represented by the following Formula (VII):

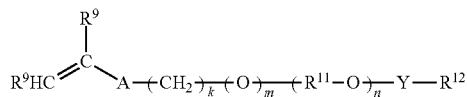

wherein, each $R^9$ is independently H, $C_1$ to $C_{30}$ alkyl, —C(O)OH, or —C(O)OR$^{10}$; $R^{10}$ is $C_1$ to $C_{30}$ alkyl; A is —CH$_2$C(O)O—, —C(O)O—, —O—, —CH$_2$O—, —NHC(O)NH—, —C(O)NH—, —Ar—(CE$_2$)$_z$—NHC(O)O—, —Ar—(CE$_2$)$_z$—NHC(O)NH—, or —CH$_2$CH$_2$NHC(O)—; Ar is a divalent aryl; E is H or methyl; z is 0 or 1; k is an integer in the range of 0 to about 30, and m is 0 or 1, with the proviso that when k is 0, m is 0, and when k is in the range of 1 to about 30, m is 1; $(R^{11}—O)_n$ is a polyoxyalkylene, which is a homopolymer, a random copolymer, or a block copolymer of $C_2$ to $C_4$ oxyalkylene units, wherein $R^{11}$ is $C_2H_4$, $C_3H_6$ (and isomers), $C_4H_8$, or a mixture thereof, and n is an integer in the range of about 5 to about 250, preferably about 5 to about 100, more preferably about 10 to about 80, and most preferably about 15 to about 60; Y is —R$^{11}$O—, —R$^{11}$NH—, —C(O)—, —C(O)NH—, —R$^{11}$NHC(O)NH—, or —C(O)NHC(O)—; and $R^{12}$ is a substituted or unsubstituted alkyl selected from the group consisting of a $C_8$ to $C_{40}$ linear alkyl, a $C_8$ to $C_{40}$ branched alkyl, a $C_8$ to $C_{40}$ carbocyclic alkyl, a $C_2$ to $C_{40}$ alkyl-substituted phenyl, an aryl-substituted $C_2$ to $C_{40}$ alkyl, and a $C_8$ to $C_{80}$ complex ester; wherein the $R^{11}$ alkylene and the $R^{12}$ alkyl group optionally includes one or more substituents selected from a hydroxyl group, a $C_1$ to $C_5$ alkoxyl group, and a halogen group.

Specific examples of associative vinyl monomers of Formula (VII) include cetyl polyethoxylated methacrylate (CEM), cetearyl polyethoxylated methacrylate (CSEM), stearyl polyethoxylated (meth)acrylate, arachidyl polyethoxylated (meth)acrylate, behenyl polyethoxylated methacrylate (BEM), lauryl polyethoxylated methacrylate (LEM), cerotyl polyethoxylated (meth)acrylate, montanyl polyethoxylated (meth)acrylate, melissyl polyethoxylated (meth)acrylate, lacceryl polyethoxylated (meth)acrylate, tristyryl phenolpolyethoxylated methacrylate (TEM), hydrogenated castor oil polyethoxylated methacrylate (HCOEM), canola polyethoxylated (meth)acrylate, and cholesterol polyethoxylated methacrylate (CHEM), where the polyethoxylated portion of the monomer comprises about 5 to about 100, preferably about 10 to about 80, and more preferably about 15 to about 60 ethylene oxide repeating units.

Semihydrophobic Vinyl Monomer

As used herein the term semihydrophobic vinyl monomer refers to compounds having two portions: (i) an ethylenically unsaturated end group moiety for addition polymerization with the other monomers of the reaction mixture, and (ii) a polyoxyalkylene moiety for attenuating the associations between the hydrophobic groups of the polymer or hydrophobic groups from other materials in a composition containing the polymer. A semihydrophobic vinyl monomer is similar in structure to the associative vinyl monomer set forth above, but has a substantially non-hydrophobic end group component and thus, does not impart any associative properties to the polymer.

In one aspect, the unsaturated end group portion (i) supplying the vinyl or other ethylenically unsaturated end group for addition polymerization can be derived from an ethylenically unsaturated mono- or di-carboxylic acid or the anhydride thereof, such as, for example, a $C_3$ or $C_4$ mono- or di-carboxylic acid, or the anhydride thereof. Alternatively, in another aspect, the end group portion (i) can be derived from an allyl ether, vinyl ether or a nonionic unsaturated urethane.

The polymerizable unsaturated end group portion (i) can also be derived from a $C_8$ to $C_{30}$ unsaturated fatty acid group containing at least one free carboxy-functional group. This $C_8$ to $C_{30}$ group is part of the unsaturated end group portion (i) and is different from the hydrophobic groups pendant to the associative monomers, which are specifically separated from the unsaturated end group of the associative monomer by a hydrophilic "spacer" portion.

The polyoxyalkylene portion (ii) specifically comprises a long-chain polyoxyalkylene segment, which is substantially similar to the hydrophilic portion of the associative monomers. Preferred polyoxyalkylene portion (ii) includes polyoxyethylene, polyoxypropylene, and polyoxybutylene units comprising about 5 to about 250, and preferably about 10 to about 100 oxyalkylene units. When the semihydrophobic vinyl monomer comprises more than one type of oxyalkylene unit, the units can be arranged in random, non-random, or block sequences.

In one embodiment, exemplary semihydrophobic vinyl monomers include at least one compound represented by one of the following formulae (VIII) or (IX):

Formula VIII
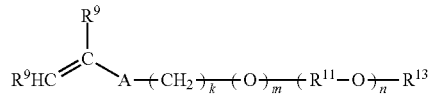

Formula IX

wherein in each of Formulae VIII and IX $R^9$, $R^{11}$, A, k, m, and n are as described previously; D is a $C_8$ to $C_{30}$ unsaturated alkyl, or a carboxy-substituted $C_8$ to $C_{30}$ unsaturated alkyl; and $R^{13}$ is H or $C_1$ to $C_4$ alkyl.

In one embodiment, the semihydrophobic vinyl monomers include monomers having the following formulae:

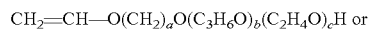

wherein a is an integer of 2, 3, or 4; b is an integer in the range of 1 to about 10 in one aspect, 2 to about 8 in another aspect, and about 3 to about 7 in a further aspect; c is an integer in the range of about 5 to about 50 in one aspect, about 8 to about 40 in another aspect, and about 10 to about 30 in a further aspect;

d is an integer in the range of 1 to about 10 in one aspect, about 2 to about 8 in another aspect, and about 3 to about 7 in a further aspect; and e is an integer in the range of about 5 to about 50 in one aspect, and about 8 to about 40 in another aspect.

Exemplary examples of semihydrophobic vinyl monomers include polymerizable emulsifiers commercially available under the trade names EMULSOGEN® R109, R208, R307, RAL109, RAL208, and RAL307 sold by Clariant Corporation; BX-AA-E5P5 sold by Bimax, Inc.; and MAXEMUL® 5010 and 5011 sold by Uniqema; and combinations thereof. Particularly preferred SVS monomers include EMULSOGEN® R208, R307, and RAL307.

According to the manufacturers EMULSOGEN® R109 is a randomly ethoxylated/propoxylated 1,4-butanediol vinyl ether having the empirical formula $CH_2=CH-O(CH_2)_4O(C_3H_6O)_4(C_2H_4O)_{10}H$; EMULSOGEN® R208 is a randomly ethoxylated/propoxylated 1,4-butanediol vinyl ether having the empirical formula: $CH_2=CH-O(CH_2)_4O(C_3H_6O)_4(C_2H_4O)_{20}H$; EMULSOGEN® R307 is a randomly ethoxylated/propoxylated 1,4-butanediol vinyl ether having the empirical formula: $CH_2=CH-O(CH_2)_4O(C_3H_6O)_4(C_2H_4O)_{30}H$; EMULSOGEN® RAL109 is a randomly ethoxylated/propoxylated allyl ether having the empirical formula $CH_2=CHCH_2O(C_3H_6O)_4(C_2H_4O)_{10}H$; EMULSOGEN® RAL208 is a randomly ethoxylated/propoxylated allyl ether having the empirical formula $CH_2=CHCH_2O(C_3H_6O)_4(C_2H_4O)_{20}H$; EMULSOGEN® RAL307 is a randomly ethoxylated/propoxylated allyl ether having the empirical formula $CH_2=CHCH_2O(C_3H_6O)_4(C_2H_4O)_{30}H$; MAXEMUL® 5010 is a carboxy-functional $C_{12}$ to $C_{15}$ alkenyl hydrophobe, ethoxylated with about 24 ethylene oxide units; MAXEMUL® 5011 is a carboxy-functional $C_{12}$ to $C_{15}$ alkenyl hydrophobe, ethoxylated with about 34 ethylene oxide units; and BX-AA-E5P5 is a randomly ethoxylated/propoxylated allyl ether having the empirical formula $CH_2=CHCH_2O(C_3H_6O)_5(C_2H_4O)_5H$.

Crosslinking Monomer

The polymers of the present invention can be prepared from a monomer mixture comprising one or more crosslinking monomers for introducing branching and controlling molecular weight. Suitable polyunsaturated crosslinkers are well known in the art. Mono-unsaturated compounds carrying a reactive group that is capable of causing a formed copolymer to be crosslinked before, during, or after polymerization has taken place can also be utilized. Other useful crosslinking monomers include polyfunctional monomers containing multiple reactive groups such as epoxide groups, isocyanate groups, and hydrolyzable silane groups. Various polyunsaturated compounds can be utilized to generate either a partially or substantially cross-linked three dimensional network.

Examples of suitable polyunsaturated crosslinking monomer components include, without being limited thereto, polyunsaturated aromatic monomers such as divinylbenzene, divinyl naphthylene, and trivinylbenzene; polyunsaturated alicyclic monomers, such as 1,2,4-trivinylcyclohexane; difunctional esters of phthalic acid such as diallyl phthalate; polyunsaturated aliphatic monomers, such as dienes, trienes, and tetraenes, including isoprene, butadiene, 1,5-hexadiene, 1,5,9-decatriene, 1,9-decadiene, 1,5-heptadiene; and the like.

Other suitable polyunsaturated crosslinking monomers include polyalkenyl ethers such as triallyl pentaerythritol, diallyl pentaerythritol, diallyl sucrose, octaallyl sucrose, and trimethylolpropane diallyl ether; polyunsaturated esters of polyalcohols or polyacids such as 1,6-hexanediol di(meth)acrylate, tetramethylene tri(meth)acrylate, allyl acrylate, diallyl itaconate, diallyl fumarate, diallyl maleate, trimethylolpropane tri(meth)acrylate, trimethylolpropane di(meth)acrylate, and polyethylene glycol di(meth)acrylate; alkylene bisacrylamides, such as methylene bisacrylamide, propylene bisacrylamide, and the like; hydroxy and carboxy derivatives of methylene bisacrylamide, such as N,N'-bismethylol methylene bisacrylamide; polyethyleneglycol di(meth)acrylates, such as ethyleneglycol di(meth)acrylate, diethyleneglycol di(meth)acrylate, and triethyleneglycol di(meth)acrylate; polyunsaturated silanes, such as dimethyldivinylsilane, methyltrivinylsilane, allyldimethylvinylsilane, diallyldimethylsilane, and tetravinylsilane; polyunsaturated stannanes, such as tetraallyl tin, and diallyldimethyl tin; and the like.

Useful monounsaturated compounds carrying a reactive group include N-methylolacrylamide; N-alkoxy(meth)acrylamide, wherein the alkoxy group is a $C_1$ to $C_{18}$ alkoxy; and unsaturated hydrolyzable silanes such as triethoxyvinylsilane, tris-isopropoxyvinylsilane, and 3-triethoxysilylpropyl methacrylate; and the like.

Useful polyfunctional crosslinking monomers containing multiple reactive groups include, but are not limited to, hydrolyzable silanes such as ethyltriethoxysilane and ethyltrimethoxysilane; epoxy-substituted hydrolyzable silanes, such as 2-(3,4-epoxycyclohexyl)ethyltriethoxysilane and 3-glycidoxypropyltrimethyoxysilane; polyisocyanates, such as 1,4-diisocyanatobutane, 1,6-diisocyanatohexane, 1,4-phenylenediisocyanate, and 4,4'-oxybis(phenylisocyanate); unsaturated epoxides, such as glycidyl methacrylate and allylglycidyl ether; polyepoxides, such as diglycidyl ether, 1,2,5,6-diepoxyhexane, and ethyleneglycoldiglycidyl ether; and the like.

Particularly useful are polyunsaturated crosslinkers derived from ethoxylated polyols, such as diols, triols and bis-phenols, ethoxylated with about 2 to about 100 moles of ethylene oxide per mole of hydroxyl functional group and end-capped with a polymerizable unsaturated group such as a vinyl ether, allyl ether, acrylate ester, methacrylate ester, and the like. Examples of such crosslinkers include bisphenol A ethoxylated di(meth)acrylate; bisphenol F ethoxylated di(meth)acrylate, ethoxylated trimethylol propane tri(meth)acrylate, and the like. Other ethoxylated crosslinkers useful in the polymers of the present invention include ethoxylated polyol-derived crosslinkers disclosed in U.S. Pat. No. 6,140,435 to Zanotti-Russo, the pertinent disclosures of which are incorporated herein by reference.

Non limiting examples of crosslinking monomers are acrylate and methacrylate esters of polyols having at least two acrylate or methacrylate ester groups, such as trimethylolpropane triacrylate (TMPTA), trimethylolpropane ethoxylated (15) triacrylate (TMPEO15TA), trimethylolpropane dimethacrylate, triethylene glycol dimethacrylate (TEGDMA), ethoxylated (30) bisphenol A dimethacrylate (EOBDMA), and the like.

Chain Transfer Agent

Suitable chain transfer agents (CTAs) for use in this invention, without being limited thereto, are selected from a variety of thio and disulfide containing compounds, such as $C_1$ to $C_{18}$ alkyl mercaptans, mercaptocarboxylic acids, mercaptocarboxylic esters, thioesters, $C_1$ to $C_{18}$ alkyl disulfides, aryldisulfides, polyfunctional thiols, and the like; phosphites and hypophosphites; haloalkyl compounds, such as carbon tetrachloride, bromotrichloromethane, and the like; and unsaturated chain transfer agents, such as alpha-methylstyrene.

Polyfunctional thiols include trifunctional thiols, such as trimethylolpropane-tris-(3-mercaptopropionate), tetrafunctional thiols, such as pentaerythritol-tetra-(3-mercaptopropionate), pentaerythritol-tetra-(thioglycolate), and pentaerythritol-tetra-(thiolactate); hexafunctional thiols, such as dipentaerythritol-hexa-(thioglycolate); and the like.

Alternatively, the chain transfer agent can be any catalytic chain transfer agent which reduces molecular weight of addition polymers during free radical polymerization of vinyl monomers. Examples of catalytic chain transfer agents include, for example, cobalt complexes (e.g., cobalt (II) chelates). Catalytic chain transfer agents can often be utilized in relatively low concentrations relative to thiol-based CTAs.

In one embodiment of the invention the chain transfer agents include octyl mercaptan, n-dodecyl mercaptan, t-dodecyl mercaptan, hexadecyl mercaptan, octadecyl mercaptan (ODM), isooctyl 3-mercaptopropionate (IMP), butyl 3-mercaptopropionate, 3-mercaptopropionic acid, butyl thioglycolate, isooctyl thioglycolate, dodecyl thioglycolate, and the like. The chain transfer agents can be added to a monomer reaction mixture preferably in amounts of up to about 10 wt. % of polymerizable monomer mixture, based on total monomer mixture weight. In one embodiment, the chain transfer agent is present in an amount of at least about 0.01 percent by weight based on the total monomer weight.

The dimethicone copolyol macromer of the present invention can be polymerized alone or in combination with at least one of copolymerizable monomers (b) through (g). The polymerization can be conducted in the optional presence of a chain transfer agent. The unsaturated monomers can be polymerized by a variety of well known free radical polymerization techniques such as bulk polymerization, photo polymerization, microwave polymerization, solution polymerization, suspension polymerization, emulsion polymerization, inverse emulsion polymerization, microemulsion polymerization and the like.

The ionic content of the polymers of the present invention can be influenced by tailoring the selection of the monomers that are copolymerized with the dimethicone copolyol macromer into the polymer backbone. For example, an anionic, cationic and/or an amphoteric monomer (and the salts of these monomers) can be copolymerized into the polymer backbone to give the polymer ionic character. By anionic, cationic, and amphoteric is meant that the respective monomer (or monomer repeating unit when incorporated into the polymer backbone) contains at least one ionizable moiety capable of forming a salt when neutralized with an acid or a base.

Examples of the anionic monomers capable of conferring ionizable moieties to the polymers of the invention contain the carboxylic acid and sulfonic acid groups described for the acidic vinyl monomers above. Exemplary salts of these monomers/repeating units include but are not limited to the alkali metal and alkaline earth metal (e.g., Li, Na, K, Ca) and the ammonium salts thereof.

Examples of cationic monomers that are capable of conferring ionizable moieties to the polymers of the invention contain the dialkylaminoalkyl moieties described for the cationic vinyl monomers above. Exemplary salts of these monomers/repeating units include but are not limited to the ($C_1$ to $C_{18}$) dialkyl sulphate salts (e.g., dimethyl sulphate, diethylsulphate); hydrogen halide salts (e.g., hydrogen chloride, hydrogen fluoride, hydrogen bromide and hydrogen iodide); and combinations thereof.

By amphoteric is meant that the polymer backbone contains both the anionic and cationic ionizable moieties described above.

The respective anionic and cationic vinyl monomers can be polymerized in the salt form (ionized) or they can be polymerized into the polymer backbone as the anionic or cationic monomer (non-ionized) and then subsequently ionized by neutralization with a base or acid, respectively.

In one embodiment, polymers containing anionic repeating units can be synthesized by polymerizing a monomer composition comprising an anionic vinyl monomer selected from one or more carboxylic acid containing monomers; one or more sulfonic acid containing monomers; one or more salts of said one or more carboxylic acid containing monomers, one or more salts of said one or more sulfonic acid containing monomers; and combinations thereof with the desired dimethicone copolyol macromer. In one exemplary embodiment, 5 to 95 wt. % of the polymerizable monomer composition (based on the weight of the total monomers that make up the monomer composition to be polymerized) comprises an anionic vinyl monomer selected from a carboxylic acid group containing monomer(s), a salt of a carboxylic acid containing monomer(s), a sulfonic acid containing monomer(s), a salt of a sulfonic acid containing monomer(s), and combinations thereof. In another exemplary embodiment, 10 to 90 wt. % of the monomer mixture comprises an anionic vinyl monomer selected from a carboxylic acid group containing monomer(s), a salt of a carboxylic acid containing monomer(s), a sulfonic acid containing monomer(s), a salt of a sulfonic acid containing monomer(s), and combinations thereof. In still another exemplary embodiment, 10 to 80 wt. % the polymerizable monomer composition comprises an anionic vinyl monomer selected from a carboxylic acid group containing monomer(s), a salt of a carboxylic acid containing monomer(s), a sulfonic acid containing monomer(s), a salt of a sulfonic acid containing monomer(s), and combinations thereof.

In one aspect of the invention, examples of polymerizable anionic vinyl monomers that contain carboxylic and sulfonic acid functionality include but are not limited to acrylic acid, methacrylic acid, maleic acid, fumaric acid, itaconic acid, crotonic acid, oleic acid, cinnamic acid, styrene sulfonic acid, and 2-acrylamido-2-methylpropane sulfonic acid (AMPS® monomer), and the metal ion (e.g., Li, Na, K, Ca) and ammonium ion salts thereof.

In another aspect, polymers containing cationic repeating units can be synthesized by polymerizing a monomer composition comprising a cationic vinyl monomer selected from one or more dialkylaminoalkyl containing group containing monomers and salts thereof, quaternized vinylimidazole, methacryloyl ethyl betaine, and methacryloyl N-oxide in the presence of a dimethicone copolyol macromer. More specifically, the monomer can be selected from one or more of di-($C_1$ to $C_6$) amino ($C_1$ to $C_5$) alkyl acrylates and methacrylates (and the hydrogen halide salts thereof), and combinations thereof. The alkyl groups attached to the nitrogen atom can be the same or different (e.g., independent of one another). In one exemplary embodiment, 5 to 95 wt. % of the polymerizable monomer composition (based on the weight of the total monomers that make up the monomer composition) comprises a cationic vinyl monomer selected from one or more of di-($C_1$ to $C_6$) amino ($C_1$ to $C_5$) alkyl acrylates and methacrylates and the ($C_1$ to $C_{18}$) dialkyl sulphate and hydrogen halide salts thereof. In another exemplary embodiment, the amount of the cationic vinyl monomer comprises 10 to 90 wt. % of the monomer mixture, and in a still further exemplary embodiment, the amount of the cationic vinyl monomer comprises 10 to 80 wt. % of the total monomer mixture.

In a further embodiment of the invention, amphoteric polymers (e.g., the polymer backbone includes repeating units polymerized from anionic and cationic monomers and salts thereof) can be synthesized by polymerizing an amphoteric monomer composition comprising both acid functional monomers (and/or their salts) and dialkylaminoalkyl monomers (and/or their salts). An amphoteric monomer composition comprising the anionic vinyl and cationic vinyl monomers and the salts thereof set forth above can be polymerized to obtain a polymer having amphoteric character. The relative amount of anionic monomer(s) to cationic monomer(s) present in the polymerizable monomer composition can range from 1 to 99 parts anionic monomer(s) to 99 to 1 part cationic monomer(s). In one exemplary embodiment, amphoteric monomers comprise 5 to 95 wt. % of the total polymerizable monomer composition (based on the weight of the total monomer content of the polymerizable monomer mixture). In another exemplary embodiment, the amount of amphoteric monomer comprises 10 to 90 wt. % of the monomer mixture, and in a still further exemplary embodiment the amount of amphoteric monomer comprises 10 to 80 wt. % of the total monomer mixture.

In another embodiment, non-ionic polymers can be synthesized by polymerizing a non-ionic monomer mixture that contains one or more of the hydrophilic monomers described above that are non-salts and that do not form salts in the presence of an acid or a base (i.e., non-ionic monomers). Examples of non-ionic monomers include but are not limited to acrylamide, methacrylamide, vinyl pyrrolidone, vinyl caprolactam, and 2-hydroxyethyl methacrylate, hydroxypropyl methacrylate (all isomers), hydroxybutyl methacrylate (all isomers), 2-hydroxyethyl acrylate, hydroxypropyl acrylate (all isomers), hydroxybutyl acrylate (all isomers), polyethylene glycol monoacrylate, polyethylene glycol monomethacrylate, polypropylene glycol monoacrylate, polypropylene glycol monomethacrylate, and combinations thereof. In one exemplary embodiment of the invention, the polymerizable monomer mixture comprises 50 to 95 wt. % (based on the weight of the total polymerizable monomer mixture) of the hydrophilic non-ionic monomers. In another exemplary embodiment, the amount of hydrophilic non-ionic monomer comprises 60 to 95 wt. % of the monomer mixture, and in a still further exemplary embodiment the amount of hydrophilic non-ionic monomer comprises 65 to 80 wt. % of the total monomer mixture.

It should be recognized that the polymerizable monomer compositions of the invention can contain at least one monomer selected from the different classes of monomers recited above in combination with the dimethicone copolyol macromers of the invention.

While overlapping weight ranges for the various monomer components that make up the polymerizable monomer mixtures of the invention have been expressed for selected embodiments of the invention, it should be readily apparent that the specific amount of each monomer component in the monomer mixture will be selected from its disclosed range such that the desired amount of each monomer will be adjusted so that the sum of all monomer components in the polymerizable monomer mixture will total 100 wt. %.

Initiators which can be used for the free radical polymerization processes of the invention are the water soluble and water insoluble persulfate, peroxide, organic hydroperoxides, organic peracids, and azo compounds. Suitable initiators include but are not limited to the ammonium persulfate, potassium persulfate, sodium persulfate, hydrogen peroxide, dibenzoyl peroxide, benzoyl peroxide, acetyl peroxide, lauryl peroxide, tert-butyl perpivalate, tert-butyl per-2-ethylhexanoate, di-tert-butyl peroxide, di-(2-ethylhexyl)-peroxy di carbonate, tert-butyl hydroperoxide, cumene hydroperoxide, azobisisobutyronitrile, azobis(2-amidinopropane) dihydrochloride or 2,2'-azobis(2-methyl-butyronitrile), peracetic acid. The peroxides and peracids can optionally be activated with reducing agents, such as sodium bisulfite or ascorbic acid, transition metals, hydrazine, and the like. Mixtures of initiator systems can also be utilized, such as, for example, sulfate/sodium peroxodisulfate, tert-butyl hydroperoxide/sodium sulfite, tert-butyl hydroperoxide/sodium hydroxymethanesulfinate. The initiators can be employed in suitable amounts, for example, in amounts of from 0.05 to 5% by weight, based on the amount of monomers to be polymerized.

In one embodiment of the invention, the polymers can be prepared using solution polymerization in a polar solvent or non-polar solvent and mixtures thereof. Exemplary solvents include but are not limited to water, methanol, methylene chloride, chloroform, carbon tetrachloride, ethanol, isopropanol, hexane, cyclohexane, ethylacetate, methylethyl ketone and benzene, toluene, N-methylpyrrolidone, and mixtures of these solvents. The amounts of monomers and solvents can be chosen to give from 15 to 90% by weight of monomer in solution (based on the total weight of monomer and solvent). The polymerization is usually carried out at temperatures of from 40 to 140° C. and at atmospheric pressure or under autogeneous pressure.

In another embodiment of the invention, the polymers can be synthesized via anionic and cationic emulsion polymerization techniques as is well known in the polymer art. Typically the anionic emulsion polymerization process is carried out at a reaction temperature in the range of about 30 to about 95° C., however, higher or lower temperatures can be used. To facilitate emulsification of the monomer mixture, the emulsion polymerization can be carried out in the presence of anionic surfactants, such as fatty alcohol sulfates or alkyl sulfonates, nonionic surfactants, such as linear or branched alcohol ethoxylates, amphoteric surfactants, or mixtures thereof. The emulsion polymerization reaction mixture also includes one or more free radical initiators in an amount in the range of about 0.01 to about 3 wt. % based on total monomer weight. The polymerization can be performed in an aqueous or aqueous alcohol medium at a low pH, i.e., preferably not more than about pH 4.5.

Anionic surfactants suitable for facilitating emulsion polymerizations are well known in the polymer art, and include but are not limited to sodium lauryl sulfate, sodium dodecyl benzene sulfonate, disodium laureth-3 sulfosuccinate, sodium dioctyl sulfosuccinate, sodium di-sec-butyl naphthalene sulfonate, disodium dodecyl diphenyl ether sulfonate, disodium n-octadecyl sulfosuccinate, phosphate esters of branched alcohol ethoxylates, and the like.

In a typical cationic polymerization procedure, a mixture of monomers is added with mixing agitation to a solution of emulsifying surfactant, such as a nonionic surfactant, preferably a linear or branched alcohol ethoxylate, or mixtures of nonionic surfactants and anionic surfactants, such as fatty alcohol sulfates or alkyl sulfonates, in a suitable amount of water, in a suitable reactor, to prepare a monomer emulsion. The emulsion is deoxygenated by any convenient method, such as by sparging with nitrogen, and then a polymerization reaction is initiated by adding a polymerization catalyst (initiator) such as sodium persulfate, or any other suitable free radical polymerization catalyst, as is well known in the emulsion polymerization art. The reaction is agitated until the polymerization is complete, typically for a time in the range of about 4 to about 16 hours. The monomer emulsion can be heated to a temperature in the range of about 20 to about 80° C. prior to addition of the initiator, if desired. Unreacted monomer can be eliminated by addition of more catalyst, as is well known in the emulsion polymerization art. The resulting polymer emulsion product can then be discharged from the reactor and packaged for storage or use.

Nonionic surfactants suitable for facilitating cationic emulsion polymerizations are well known in the polymer art, and include, without limitation, linear or branched alcohol ethoxylates, $C_8$ to $C_{12}$ alkylphenol alkoxylates, such as octylphenol ethoxylates, polyoxyethylene polyoxypropylene block copolymers, and the like. Other useful nonionic surfactants include $C_8$ to $C_{22}$ fatty acid esters of polyoxyethylene glycol, mono and diglycerides, sorbitan esters and ethoxylated sorbitan esters, $C_8$ to $C_{22}$ fatty acid glycol esters, block copolymers of ethylene oxide and propylene oxide having an HLB value of greater than about 15, ethoxylated octylphenols, and combinations thereof.

In one aspect, alkylphenol alkoxylate surfactants include an octylphenol sold under the trade name IGEPAL® CA-897 by Rhodia, Inc. Preferred linear alcohol alkoxylates include polyethylene glycol ethers of cetearyl alcohol (a mixture of cetyl and stearyl alcohols) sold under the trade names PLURAFAC® C-17, PLURAFAC® A-38 and PLURAFAC®

A-39 by BASF Corp. Preferred polyoxyethylene polyoxypropylene block copolymers include copolymers sold under the trade names PLURONIC® F127, and PLURONIC® L35 by BASF Corp.

In another aspect, the nonionic surfactants include Ethoxylated (50) linear fatty alcohols such as DISPONIL® A 5060 (Cognis), branched alkyl ethoxylates such as GENAPOL® X 1005 (Clariant Corp.), secondary $C_{12}$ to $C_{14}$ alcohol ethoxylates such as TERGITOL® S15-30 and S15-40 (Dow Chemical Co.), ethoxylated octylphenol-based surfactants such as TRITON® X-305, X-405 and X-705 (Dow Chemical Co.), IGEPAL® CA 407, 887, and 897 (Rhodia, Inc.), ICONOL® OP 3070 and 4070 (BASF Corp.), SYNPERONIC® OP 30 and 40 (Uniqema), block copolymers of ethylene oxide and propylene oxide such as PLURONIC® L35 and F127 (BASF Corp.), and secondary $C_{11}$ alcohol ethoxylates such as EMULSOGEN® EPN 407 (Clariant Corp.). Numerous other suppliers are found in the trade literature.

The free radical polymerization initiators discussed above are suitable herein. Exemplary commercially available polymerization initiators include the VAZO® free radical polymerization initiators, available from DuPont, such as VAZO® 44 (2,2'-azobis(2-(4,5-dihydroimidazolyl)propane), VAZO® 56 (2,2'-azobis(2-methylpropionamidine) dihydrochloride), and VAZO® 68 (4,4'-azobis(4-cyanovaleric acid).

Optionally, other emulsion polymerization additives, which are well known in the emulsion polymerization art, such as buffering agents, chelating agents, inorganic electrolytes, chain terminators, antifoaming agent, biocides diluents, and pH adjusting agents can be included in the polymerization system.

An exemplary general anionic emulsion polymerization procedure for the preparation of alkali swellable or alkali soluble polymer embodiment of the present invention is provided below.

A monomer emulsion is prepared in a first reactor equipped with a nitrogen inlet and an agitator, by combining a desired amount of each monomer in water containing an emulsifying amount of an anionic surfactant under a nitrogen atmosphere and with mixing agitation. To a second reactor equipped with an agitator, nitrogen inlet and feed pumps are added a desired amount of water and additional anionic surfactant, if desired, under a nitrogen atmosphere, and the contents of the second reactor are heated with mixing agitation. After the contents of the second reactor reach a temperature in the range of about 55 to 98° C., a free radical initiator is injected into the so formed aqueous surfactant solution in the second reactor, and the monomer emulsion from the first reactor is then gradually pumped into the second reactor over a period of typically in the range of about one to about four hours at a controlled reaction temperature in the range of about 45 to 95° C. After completion of the monomer addition, an additional quantity of free radical initiator can be added to the second reactor, if desired, and the resulting reaction mixture is typically held at a temperature of about 45 to 95° C. for a time period sufficient to complete the polymerization reaction. The resulting polymer emulsion can then be cooled and discharged from the reactor.

One skilled in the polymer arts will recognize that the amounts of each monomer component can be adjusted to obtain polymers having any desired ratio of monomers. Larger or smaller proportions of water may also be utilized, as desired. Water miscible solvents, such as alcohols, and other polymerization additives, as described above, may also be included in the reaction mixture. Nonionic surfactants, such as linear or branched alcohol ethoxylates, can also be added as is known in the emulsion polymerization art.

The product polymer emulsions can be prepared to preferably contain about 1 percent to about 60 percent total polymer solids, more preferably about 10 percent to about 50 percent total polymer solids, most preferably about 15 percent to about 45 percent total polymer solids (TS) based on the weight of the polymer.

Prior to any neutralization, the polymer emulsions, as produced, typically have a pH in the range of about 2 to not more than about 5.5, a Brookfield viscosity of not more than about 100 milli-Pascal seconds (mPa·s) at ambient room temperature (spindle #2, 20 rpm) and a glass transition temperature (Tg) of not more than about 250° C. as determined by Method below.

Optionally, the produced polymer emulsions can be further processed by adjusting the pH to a value preferably in the range of about 3 to about 7.5 or greater, if an alkaline pH is desired, with alkaline materials, preferably alkali metal hydroxides, organic bases, and the like. The polymer emulsions typically swell to a viscosity greater than about 100 mPa·s and form viscous solutions or gels at neutral to alkaline pH, and the polymers are generally substantially stable at such pH values, even at pH values greater than about 12. Alkali-soluble polymer emulsions can also be made to be soluble at neutral to alkaline pH without the concomitant swelling or viscosity increase. The polymer emulsions can be diluted with water or solvent, or concentrated by evaporation of a portion of the water. Alternatively, the obtained polymer emulsion may be substantially dried to a powder or crystalline form by utilizing equipment well known in the art, such as, for example, a spray drier, a drum drier, or a freeze drier.

The polymers/monomers of the present invention insofar as they contain ionizable groups can be fully or partially neutralized with acids or bases before or after polymerization to adjust the solubility or dispersability in aqueous medium. In addition, the viscosity properties of the polymers can be adjusted by neutralizing the polymer.

Non limiting examples of suitable neutralizing agents for monomers and polymers that carry anionic groups are mineral bases and organic bases. Non limiting examples of mineral bases include the alkali metal hydroxides (e.g., lithium, sodium and potassium); sodium carbonate; ammonium hydroxide; and ammonia. Non limiting examples of organic bases such as amino alcohols (e.g., 2-amino-2-methyl-1-propanol, monoethanolamine, diethanolamine, triethanolamine, triisopropylamine, tris[(2-hydroxy)-1-propyl]amine, 2-amino-2-methyl-1,3-propanediol, 2-amino-2-hydroxymethyl-1,3-propanediol; diamines such as lysine; cocamine; oleamine; and mopholine.

Non limiting examples of suitable neutralizing agents for monomers and polymers that carry cationic groups are organic acids, including amino acids, and inorganic mineral acids. Non limiting examples of organic acids include acetic acid, citric acid, fumaric acid, glutamic acid, tartaric acid, lactic acid, and glycolic acid. Non limiting examples of mineral acids include hydrochloric acid, nitric acid, phosphoric acid, sodium bisulfate, sulfuric acid, and the like, and mixtures thereof.

The foregoing neutralizing agents also can be utilized a pH adjusting agents to adjust the pH of the neutralized polymer or a composition containing the neutralized polymer.

The polymers of the invention that contain anionic and/or cationic groups can swell upon neutralization with the appropriate base or acid. These polymers beneficially can thicken acidic or basic aqueous formulations to provide aesthetically smooth-textured products that flow smoothly and spread easily. The inventive, multi-purpose polymers can be employed as thickeners, emulsifiers, stabilizers, suspending agents, film formers, fixatives, conditioners, moisturizers, spreading aids, surface modifiers, shine enhancers, and carriers for enhancing the efficacy, deposition or delivery of chemically and physiologically active ingredients and cosmetic materials, and as vehicles for improving the psychosensory, and aesthetic properties of a formulation in which they are included.

The cationic character of the polymers at low pH makes them useful as antistatic agents, and, under certain conditions, may also provide biocidal, anti-microbial, or other preservative activity.

The anionic polymer embodiments of the invention when utilized in combination with at least one anionic, zwitterionic, amphoteric, nonionic, cationic surfactant or combinations thereof can be formulated by the "back-acid" thickening technique disclosed in U.S. Pat. No. 6,635,702, the disclosure of which is incorporated herein by reference. The back-acid technique involves neutralizing an anionic thickening polymer with alkaline neutralizing agent to build viscosity, and then subsequently reducing the pH with an acidic pH reducing agent to a desired final pH. The viscosity and yield value generally remain unchanged or often actually increase upon the subsequent reduction of the final pH of the formulation. This formulating technique broadens the scope of application of these polymers and provides the use of anionic viscosity modifying polymers in formulations that require an acidic pH regime. Additionally, the process of "back-acid" thickening can also be used to further increase the viscosity and stability of compositions formulated in the slightly acidic and in the alkaline pH regime.

At least one polymer of the present invention is added to water and mixed. The surfactant is subsequently added to the aqueous polymeric solution and mixed therein. An alkaline material is then added and mixed to increase the pH of the composition to at least about 5 in one embodiment of the invention, at least about 6 in another embodiment, and at least about 6.5 in a further embodiment. The alkaline material is preferably a neutralizing agent, such as sodium hydroxide, potassium hydroxide, triethanolamine, or another fatty acid amine neutralizing agent commonly used in said applications. Alternatively, other alkaline materials can be used, such as pre-neutralized surfactants. In one embodiment, the initial pH of the formulation should desirably be at least about 0.5 or 2 pH units and preferably at least 3, 4, or even 5 pH units above the final target pH of the composition. An acidic material or pH adjusting agent is then added to reduce the pH of the composition.

The material used to decrease the pH of the formulation is an acidic material, and can be selected from an organic acid, such as citric acid, acetic acid, alpha-hydroxy acid, beta-hydroxy acid, salicylic acid, lactic acid, glycolic acid, natural fruit acids, or combinations thereof. In addition, inorganic acids, for example hydrochloric acid, nitric acid, sulfuric acid, sulfamic acid, phosphoric acid, and combinations thereof can be utilized. The amount of such acid is such that the anionic moieties on the polymer backbone become sufficiently neutralized to build the desired viscosity values. In one aspect from about 0.1 to about 20%, in another from about 0.2% to 15%, and in still another aspect from about 0.25% to about 10% by weight based upon the total weight of the stabilized composition can be employed.

The desired pH to stabilize compositions of the present invention is obviously dependent on the specific applications. Generally, Personal Care applications have a desired pH range of about 3 to about 7.5, desirably from about 4 to about 6. Generally, Home Care applications have a desired pH range of about 1 to about 12, and desirably from about 3 to about 10. More specifically, when a generally insoluble silicone or pearlescent compound is utilized, a desired pH is from about 5.5 to about 12, whereas when a hair dye is stabilized, the pH is from about 5 to about 9.

The cationic polymer embodiments of the invention when utilized in combination with at least one zwitterionic and/or amphoteric surfactant can be formulated by a "back-alkaline" formulation technique to obtain higher pH compositions utilizing cationic rheology modifying polymers. In one embodiment of the invention, the surfactant is selected from at least one amphoteric or zwitterionic surfactant. Optionally, the cationic polymer/surfactant composition can contain other surfactants selected from anionic, nonionic, and cationic surfactants, or combinations thereof.

The formulations containing the cationic polymers of the invention in combination with an amphoteric surfactant are lowered to an initial acidic pH value using an acidic neutralizing agent (to build a desired increase in viscosity) and then a alkaline pH adjusting agent is subsequently added to raise the pH value to the desired final pH value of the formulation. The viscosity, turbidity and yield value generally remain unchanged or often actually improve. The back-alkaline formulating technique broadens the scope of application for the cationic polymers of the invention, allowing for the increase of the pH of a formulation subsequent to the acid treatment or polymer thickening step. Additionally, the process of back-alkaline thickening can be used to further increase the viscosity and stability of compositions formulated in the generally accepted pH range.

In one embodiment of the invention, the one or more cationic copolymers, polymers, and the like are added to water and mixed. An amphoteric and/or zwitterionic surfactant is subsequently added to the aqueous polymeric solution and mixed therein. If desired, optional surfactants selected from anionic, nonionic, and cationic surfactants, or combinations thereof can be added to the formulation. Suitable amphoteric, anionic, cationic and nonionic surfactants are described above. An acidic pH adjusting agent is then added and mixed to decrease the pH of the composition to obtain the desired low pH formulation. In one aspect, the pH of the composition can be initially adjusted with an acid to a pH of about 0.5 to about 7.0, in another aspect between about 3.0 to about 6.0, and in still a further aspect from about 4.0 to about 5.0. The acidic pH adjusting agent can be selected from the organic and mineral acids described herein. In another embodiment, any acidic ingredient that is capable of reducing the initial pH of the cationic polymer composition and effecting a viscosity increase of the polymer composition is contemplated within the scope of the invention. The acidic active ingredients can be employed with or without a pH adjusting agent. Examples of suitable acidic ingredients are selected from but not limited to the dermatological and cosmeceutical acidic active ingredients described herein.

When citric acid is employed in the cationic polymer neutralization step (i.e., pH lowering), the viscosity of the composition actually increases when the alkaline pH adjusting agent is subsequently added to the formulation. The pH of the acid thickened composition should desirably be at least about 1 and preferably 2 units and preferably at least 3 pH units below the final target pH of the composition. An alkaline pH adjusting agent is then added to increase the pH of the composition to the final target pH. Alkaline pH adjusting agents suitable for the Back-Alkaline formulation technique are described herein.

The desired pH of the compositions of the present invention is obviously dependent on the specific end product applications. Generally, Personal Care compositions have a pH range of about 3 to about 8.0. Generally, Home Care compositions have a pH range of about 1 to about 12.

Advantageously, the polymers of this invention can be employed, without being limited thereto, in personal care products, health care products, household care products, institutional and industrial (collectively "I&I") care products, and the like. The polymers can be employed as a film forming conditioner, and for promoting the deposition of silicone, conditioning agents or aids, color cosmetics and polar and non-polar oils on skin, hair, nails, and fibers. Further, the polymers can be employed in products for industrial chemical processes, textile finishing processes, printing, adhesive coating, and like applications as, for example, rheology modifiers, emulsifiers, stabilizers, solubilizers, suspending agents, flocculents, shine enhancers, surface modifiers, and pigment and grinding additives. The dimethicone copolyol containing polymers of the invention are useful in many applications such as, for example, thickeners and film-formers in a variety of dermatological, cosmeceutical compositions employed for topically ameliorating skin conditions caused by drying, photodamage, aging, acne, and the like, containing conditioners, moisturizers, antioxidants, exfoliants, keratolytic agents, vitamins, and the like, typically containing an active acidic ingredient and having a pH in the range of about 0.5 to about 5.

In one cosmeceutical aspect, a cationic polymer can be employed as a thickener for active skin treatment lotions and creams containing, as active ingredients, acidic anti-aging, anti-cellulite, and anti-acne agents, hydroxy carboxylic acids, such as alpha-hydroxy acid (AHA), beta-hydroxy acid (BHA), alpha-amino acid, alpha-keto acids (AKAs), and mixtures thereof. In such cosmeceuticals, AHAs can include, but are not limited to, lactic acid, glycolic acid, fruit acids, such as malic acid, citric acid, tartaric acid, extracts of natural compounds containing AHA, such as apple extract, apricot extract, and the like, honey extract, 2-hydroxyoctanoic acid, glyceric acid (dihydroxypropionic acid), tartronic acid (hydroxypropanedioic acid), gluconic acid, mandelic acid, benzilic acid, azelaic acid, alpha-lipoic acid, salicylic acid, AHA salts and derivatives, such as arginine glycolate, ammonium glycolate, sodium glycolate, arginine lactate, ammonium lactate, sodium lactate, alpha-hydroxybutyric acid, alpha-hydroxyisobutyric acid, alpha-hydroxyisocaproic acid, alpha-hydroxyisovaleric acid, atrolactic acid, and the like. BHAs can include, but are not limited to, 3-hydroxy propanoic acid, beta-hydroxybutyric acid, beta-phenyl lactic acid, beta-phenylpyruvic acid, and the like. Alpha-amino acids include, without being limited thereto, alpha-amino dicarboxylic acids, such as aspartic acid, glutamic acid, and mixtures thereof, sometimes employed in combination with fruit acid. AKAs include pyruvic acid. In some antiaging compositions, the acidic active agent may be retinoic acid, a halocarboxylic acid, such as trichloroacetic acid, an acidic antioxidant, such as ascorbic acid (vitamin C), kojic acid, a mineral acid, phytic acid, lysophosphatidic acid, and the like. Some acidic anti-acne actives, for example, can include salicylic acid, derivatives of salicylic acid, such as 5-octanoylsalicylic acid, retinoic acid, and its derivatives. When a cationic polymer embodiment of the invention is incorporated into the foregoing acidic products, the active acid ingredient can serve as both the active skin treatment agent and acid swelling agent for the cationic polymer to achieve the desired viscosity.

A discussion of the use and formulation of active skin treatment compositions is in COSMETICS & TOILETRIES®, C&T Ingredient Resource Series, "AHAs & Cellulite Products How They Work", published 1995, and "Cosmeceuticals", published 1998, both available from Allured Publishing Corporation, incorporated herein by reference. Compositions containing alpha-amino acids acidified with ascorbic acid are described in U.S. Pat. No. 6,197,317 B1, and a commercial cosmeceutical preparation utilizing these acids in an anti-aging, skin care regimen is sold under the tradename, AFAs, by exCel Cosmeceuticals (Bloomfield Hills, Mich.). The term "AFA", as described in the supplier's trade literature, was coined by the developer to describe the amino acid/vitamin C combination as Amino Fruit Acids and as the acronym for "Amino acid Filaggrin based Antioxidants."

Other health care products in which the instant polymers can be included are medical products, such as topical and non-topical pharmaceuticals, and devices. In the formulation of pharmaceuticals, a polymer embodiment of the invention can be employed as a thickener and/or lubricant in such products as creams, pomades, gels, pastes, ointments, tablets, gel capsules, purgative fluids (enemas, emetics, colonics, and the like), suppositories, anti-fungal foams, eye products (ophthalmic products, such as eye drops, artificial tears, glaucoma drug delivery drops, contact lens cleaner, and the like), ear products (wax softeners, wax removers, otitis drug delivery drops, and the like), nasal products (drops, ointments, sprays, and the like), and wound care (liquid bandages, wound dressings, antibiotic creams, ointments, and the like), without limitation thereto.

The film-forming ability of the polymer makes the polymer particularly suitable as a vehicle for topical medical compositions for promoting and enhancing the transdermal delivery of active ingredients to or through the skin, for enhancing the efficacy of anti-acne agents formulations and topical analgesics, and for controlling release of drugs, such as antacids from tablets, or syrups, at low pH, such as in the stomach; controlling drug release from tablets, lozenges, chewables, and the like in the mildly acidic environment of the mouth; or from suppositories, ointments, creams, and the like in the mildly acidic environment of the vagina; to promote deposition of dandruff control agents from shampoos, salves, and the like; to enhance the deposition of colorants on skin from pigmented cosmetics (makeups, lipsticks, rouges, and the like) and on hair from hair dyes, and the like.

In addition to the foregoing embodiments the cationic polymer of the invention at an acid pH, makes the polymer useful as a thickener for antistatic, biocidal, antimicrobial, and other preservative compositions, in a variety of personal care, health care, I&I, and medical applications. For example, the polymer can be employed as a thickener in over-the-counter (OTC) health care and pharmaceutical products where cationic biocides are typically employed, such as in oral care compositions for plaque and tartar control, and liquid vehicles containing therapeutic agents, such as syrups, gels, and the like. Under certain controlled pH conditions, the cationic character of the cationic polymer embodiment, itself, may also provide antistatic activity or biocidal, antimicrobial, or like preservative activity.

The polymers of the present invention can be employed, without limitation, as a lubricant coating for medical devices, such as soft tissue implants, surgical gloves, catheters, cannulae, and the like, as removable protective film coatings for medical instruments, wound dressings, and the like, as a muco-adhesive, especially in the acid environment of the stomach, as a carrier and thickener in formulated products for medical applications, such as disinfectant hand creams, anti-viral products (for anionic viruses), antibiotic ointments, sprays and creams, non-drip, sprayable disinfectant in hospitals, hard surface antimicrobial finish applied during routine maintenance, and the like.

In home care and I&I applications, the dimethicone copolyol containing polymers of the present invention can be used, for example, as a rheology modifier, fabric conditioning agent, antistatic agent, especially to improve formulation efficiency through "cling-on-surface" or improving efficacy of disinfectants, and biocidal formulations, and to synergistically improve fabric softening efficacy in combination with traditional fabric softeners. Typical household and I&I products that can contain polymers of the invention, include, without being limited thereto, laundry and fabric care products, such as detergents, fabric softeners (liquids or sheets), ironing sprays, dry cleaning aids, antiwrinkle sprays, spot removers and the like; hard surface cleansers for the kitchen and bathroom and utilities and appliances employed or located therein, such as toilet bowl gels, tub and shower cleaners, hard water deposit removers, floor and tile cleansers, wall cleansers, floor and chrome fixture polishes, alkali-strippable vinyl floor cleaners, marble and ceramic cleaners, air freshener gels, liquid cleansers for dishes, and the like; disinfectant cleaners, such as toilet bowl and bidet cleaners, disinfectant hand soaps, room deodorizers, and the like.

Products containing polymers of the present invention can contain various conventional additives and adjuvants known in the art, some of which can serve more than one function. The amounts employed will vary with the purpose and character of the product and can be readily determined by one skilled in the formulation arts and from the literature. The term "cosmetic adjuvant" includes cosmetically and pharmaceutically acceptable product stabilizing and product finishing agents that maintain the physical stability of the composition and its visible aesthetic appearance and market appeal during the useful shelf life of the composition.

The term "fixative" as applied to polymers encompasses the properties of film-formation, adhesion, or coating deposited on a surface on which the polymer is applied. The terms "hair styling and hair fixative" as commonly understood in the hair care arts, and as used herein, refer collectively to hair setting agents that are hair fixatives and film formers and which are topically applied to the hair to actively contribute to the ease of styling and/or holding of a hair set, and to maintain the restylability of the hair set. Hence, hair setting compositions include hair styling, hair fixative, and hair grooming products that conventionally are applied to the hair (wet or dry) in the form of gels, rinses, emulsions (oil-in-water, water-in-oil or multiphase), such as lotions and creams, pomades, sprays (pressurized or non-pressurized), spritzes, foams, such as mousses, shampoos, solids, such as sticks, semisolids and the like, or are applied from a hair setting aid having the hair setting composition impregnated therein or coated thereon, to leave the hair setting agent in contact on the hair for some period until removed, as by washing.

The term "conditioning agents", and grammatical variations thereof, as it relates to compositions for skin care and hair care includes cosmetically and pharmaceutically useful materials that are humectants, moisturizers, and emollients. It is recognized that some conditioning agents can serve more than one function in a composition, such as emulsifying agents, lubricants, and solvents.

In one aspect of the invention, a hair care composition embodiment comprises a polymer of the present invention in an amount effective to provide to the hair care composition a property, such as a hair fixative property, a hair conditioning property, a viscid property (thickening, rheology modifying), or a combination thereof. In addition to the instant polymer(s) the hair care composition can include one or more auxiliary film-forming agent, auxiliary hair-fixative agent, auxiliary hair conditioning agent, auxiliary rheology modifying agent, a structurant, or a mixture thereof, or any of the ingredients set forth and described herein as is well known to those skilled in the hair care formulation art. When included in hair styling compositions, the polymers of the inventions enhance resistance to humidity, stiffness, hold, gloss, conditioning, manageability, and restylability when used as the sole hair fixative component or in combination with other hair fixatives.

A structurant provides additional viscosity and structure to creams, gels, pomades, ointments, salves and semisolid highly viscous waxy products. Structurants are ingredients that are appropriate for topical administration to the hair and skin and are compatible with the other ingredients in a particular personal care formulation. Exemplary structurant materials include the waxes, petrolatum, fatty acids and alcohols and esters thereof, and the anionic, cationic, nonionic, and amphoteric surfactants set forth and described herein; and mixtures thereof. In one embodiment of the invention, the structurant can be present in an amount ranging from about 5 wt. % to about 50 wt. % of the weight of the total composition. In another embodiment the structurant can be present in an amount ranging from about 8 wt. % to about 30 wt. %.

In another embodiment of the invention, a skin care composition embodiment comprises a polymer of the present invention in an amount effective to provide to the skin care composition a property, such as a skin conditioning property, a viscid property (thickening, rheology modifying), or a combination thereof. Optionally, the skin care composition can include one or more auxiliary skin conditioning agent, auxiliary rheology modifying agent, or a mixture thereof.

Additives and adjuvant ingredients, products, or materials, which may be employed with the inventive polymers discussed herein will be referred to by the international nomenclature commonly referred to as INCI name given them in the International Cosmetic Ingredient Dictionary, published by the Cosmetic, Toiletry, and Fragrance Association, Washington D.C. (hereafter INCI Dictionary), such as can be found in any edition thereof, for example, Volumes 1 and 2, Sixth Edition, (1995) or Volumes 1-3, Seventh and Eighth Editions, (1997, 2000), or by their commonly used chemical names. Numerous commercial suppliers of materials listed by INCI name, trade name or both can be found in the INCI Dictionary and in numerous commercial trade publications, including but not limited to the 2001 McCutcheon's Directories, Volume 1: Emulsifiers & Detergents and Volume 2: Functional Materials, published by McCutcheon's Division, The Manufacturing Confectioner Publishing Co., Glen Rock, N.J. (2001); and 2001 Cosmetic Bench Reference, edition of COSMETICS & TOILETRIES®, 115 (13), published by Allured Publishing Corporation, Carol Stream, Ill. (2001); the relevant disclosures of each are incorporated herein by reference. Such components and the formulation of compositions are also described in detail in well known references, such as Cosmetics Science and Technology, First Edition (Sagarin (ed)), published 1957, and Second Edition (Balsam, et al. (eds)), published 1972-74; and The Chemistry and Manufacture of Cosmetics, Second Edition (deNavarre (ed)), published 1975, and Third Edition (Schlossman (ed)), published 2000, both available from Allured Publishing Corporation; Rieger (ed), Harry's Cosmeticology, 8th Edition, Chemical Publishing, Co., Inc., New York, N.Y. (2000); and various formularies available to those skilled in the pharmaceutical arts, such as Remington's Pharmaceutical Sciences, Fourteenth Edition, Mack Publishing Company, Easton, Pa. (1970); the relevant disclosures of each are incorporated herein by reference.

It is known that formulated compositions for personal care and topical, dermatological, health care, which are applied to the skin and mucous membranes for cleansing or soothing, are compounded with many of the same or similar physiologically tolerable ingredients and formulated in the same or similar product forms, differing primarily in the purity grade of ingredient selected, by the presence of medicaments or pharmaceutically accepted compounds, and by the controlled conditions under which products may be manufactured. Likewise, many of the ingredients employed in products for households, and I&I are the same or similar to the foregoing, differing primarily in the amounts and material grade employed. It is also known that the selection and permitted amount of ingredients also may be subject to governmental regulations, on a national, regional, local, and international level. Thus, discussion herein of various useful ingredients for personal care and health care products may apply to household and I&I products and industrial applications.

The choice and amount of ingredients in formulated compositions containing a polymer embodiment of the invention will vary depending on the product and its function, as is well known to those skilled in the formulation arts. Formulation ingredients for personal care and topical health care products containing the polymer embodiments of the invention typically can include, but are not limited to, solvents and diluents (including water), anionic, cationic, amphoteric, and nonionic surfactants and silicone containing derivatives thereof (as cleansing agents, emulsifying agents, foam boosters, hydrotropes, solubilizing agents, and suspending agents); nonsurfactant suspending agents; emulsifiers; emulsion stabilizers; waxes; dispersants; hair and skin conditioning agents; lubricants and slip aids; moisture barriers and emollients; humectants; moisturizers and the like; auxiliary rheology modifiers; viscosity adjusting agents such as solvents, electrolytes, hydrotropes, and the like; hair conditioning agents, auxiliary conditioning agents, such as antistatic agents, synthetic oils, vegetable or animal oils, silicone oils, monomeric or polymeric quaternized ammonium compounds and derivatives thereof, sheen enhancers, hair fixatives, film-formers, skin protectants, binders, chelating agents, antimicrobial agents, antifungal agents, antidandruff agents, antifoaming agents, abrasives, adhesives, absorbents, deodorant agents; antiperspirant agents; opacifying agents; pearlescent material (pearlizing agents); insoluble materials, antioxidants, preservatives, propellants (water-miscible or water immiscible) such as fluorinated hydrocarbons, liquid volatile hydrocarbons, compressed gases, and the like; polymer film modifying agents, such as plasticizers, tackifiers, detackifiers, wetting agents, and the like; spreading aids; sunscreen agents; sunless skin tanning accelerators; ultraviolet light absorbers, opacifiers; acidifying and alkalizing pH adjusting agents, buffering agents, botanical extracts; colorants (temporary or permanent) such as pigments and dyes; oxidizing agents; reducing agents; hair and skin bleaching agents, pigments; pearlescenting agents, proteinaceous materials and derivatives thereof; vitamins and derivatives thereof, physiologically active agents, anti-inflammatory agents, topical anesthetics, fragrance and fragrance solubilizers, and the like; and combinations thereof; in addition to ingredients previously discussed that may not appear herein. Oral care products, for example, can contain anticaries, antitartar and/or antiplaque agents in addition to surfactants, abrasives, humectants, and flavorants. An extensive listing of substances and their conventional functions and product categories appears in the INCI Dictionary, generally, and in Vol. 2, Sections 4 and 5 of the Seventh Edition, in particular, or www.ctfa-online.org incorporated herein by reference. An exemplary listing of suitable additives, adjuvants, ingredients, etc. for use in combination with the dimethicone copolyol polymers of the invention in personal care, topical health care, household care, institutional care, and industrial care products as well as in industrial processes along with exemplary amounts is set forth below.

Suitable chelators include EDTA (ethylene diamine tetraacetic acid) and salts thereof such as disodium EDTA and tetrasodium EDTA, citric acid and salts thereof, cyclodextrins, and the like, and mixtures thereof. Such suitable chelators typically comprise about 0.001 wt. % to about 3 wt. %, preferably about 0.01 wt. % to about 2 wt. %, and more preferably about 0.01 wt. % to about 1 wt. % of the total weight of the personal care compositions of the present invention.

Examples of compounds that are suitable for use as propellants are trichlorofluoromethane, dichlorodifluoromethane, dichlorotetrafluoroethane, monochlorodifluoromethane, difluroethane trichlorotrifluoroethane, dimethyl ether, propane, n-butane, and isobutane, either singly or admixed. Water-soluble gases such as dimethyl ether, carbon dioxide, and/or nitrous oxide also can be used to obtain aerosol sprays having reduced flammability.

Water-immiscible, liquefied, hydrocarbon and halogenated hydrocarbon gases such as propane, butane, and chlorofluorocarbons can be used advantageously to deliver the contents of an aerosol container without the dramatic pressure drops associated with other immiscible gases. The head space left inside the aerosol container is not a factor because the liquefied gas sits on top of the aqueous composition and the pressure inside the container is maintained at the vapor pressure of the saturated hydrocarbon vapor.

Other insoluble, compressed gases such as nitrogen, helium, and fully fluorinated oxetanes and oxepanes also are useful to deliver the compositions from aerosol containers. If the propellant, such as dimethyl ether, incorporates a vapor pressure suppressant (e.g., trichloroethane or dichloromethane), the amount of suppressant is included as part of the propellant for weight percentage calculations.

The amount of the propellant used is governed by normal factors well known in the aerosol art. For mousses the level of propellant is generally up to 30%, in one aspect from 2% to 30%, in another aspect and from 3% to 15% by weight in a further aspect based on total weight of the composition. If a propellant such as dimethyl ether includes a vapor pressure suppressant (e.g. trichloroethane or dichloromethane), for weight percentage calculations, the amount of suppressant is included as part of the propellant.

Examples of pearlescent materials included but are not limited to titanium dioxide coated mica, iron oxide coated mica, ethylene glycol mono-stearate, ethylene glycol distearate, polyethylene glycol distearate, bismuth oxychloride, coated mica, myristyl myristate, guanine, glitter (polyester or metallic), and mixtures thereof. Other pearlescent materials can be found in U.S. Pat. No. 4,654,207 and U.S. Pat. No. 5,019,376, herein incorporated by reference. The amount of the pearlescent material can generally be used in amounts of from about 0.05% to about 10% and desirably from about 0.15% to about 3% by weight based upon the total weight of the stabilized composition.

Examples of insoluble compounds include but are not limited to titanium dioxide; pumice; calcium carbonate; talc; potato starch; tapioca starch; jojoba beads; polyethylene beads; walnut shells; loofah; apricot seeds; almond meal; corn meal; paraffin; oat bran/oat hulls; gelatin beads; alginate beads; stainless steel fibers; iron oxide pigments; air bubbles; mica coated iron oxides; kaolin clay; zinc pyrithione; salicylic acid; zinc oxide; zeolite; styrofoam beads; phosphates; silica, and the like. Other generally insoluble compounds include teatree powder, microsponges, confetti (a trademark of united guardian company), talc, beeswax, and the like. The amount of the insoluble compounds incorporated into the instant compositions will vary depending upon its purpose, desired end result, and efficacy thereof. Hence amounts can vary widely, but frequently will be within a general range of from about 0.1% to about 50% by weight based upon the total weight of the composition.

A diluent such as water (often deionized) can be used and typically comprises about 5 wt. % to about 99 wt. %, and preferably about 20 wt. % to about 99 wt. % of the total weight of the personal care compositions of the present invention.

Suitable humectant skin and/or hair conditioners include allantoin; pyrrolidone carboxylic acid and its salts; hyaluronic acid and its salts; sorbic acid and its salts; urea; lysine, arginine, cystine, guanidine, and other amino acids; polyhydroxy alcohols such as glycerin, 1,2-propylene glycol, 1,3-propylene glycol, dipropylene glycol, hexylene glycol, hexanetriol, ethoxydiglycol, dimethicone copolyols, sorbitol, mannitol, xylitol, tripropylene glycol, tetrapropylene glycol, butylene glycol, 1,3-butylene glycol, 1,3-propanediol, 2,4-dihydroxy-2-methylpentane, and the esters thereof; polyethylene glycol; glycolic acid and glycolate salts (e.g. ammonium and quaternary alkyl ammonium); lactic acid and lactate salts (e.g. ammonium and quaternary alkyl ammonium); sugars and starches; sugar and starch derivatives (e.g. alkoxylated glucose); panthenols such as dl-panthenol; lactamide monoethanolamine; acetamide monoethanolamine; and the like, and mixtures thereof. Such suitable humectants typically comprise about 1 wt. % to about 10 wt. %, preferably about 2 wt. % to about 8 wt. %, and more preferably about 3 wt. % to about 5 wt. % of the total weight of the personal care compositions of the present invention.

Suitable lubricants and slip aids include volatile silicones, such as cyclic or linear polydimethylsiloxanes, and the like. The number of silicon atoms in cyclic silicones preferably is from about 3 to about 7 and more preferably 4 or 5. Exemplary volatile silicones, both cyclic and linear, are available from Dow Corning Corporation as Dow Corning 344, 345 and 200 fluids; Union Carbide as Silicone 7202 and Silicone 7158; and Stauffer Chemical as SWS-03314.

The linear volatile silicones typically have viscosities of less than about 5 mPa·s at 25° C., while the cyclic volatile silicones typically have viscosities of less than about 10 mPa·s at 25° C. "Volatile" means that the silicone has a measurable vapor pressure. A description of volatile silicones can be found in Todd and Byers, Volatile Silicone Fluids for Cosmetics, Cosmetics and Toiletries, Vol. 91, pp. 29-32, 1976 incorporated herein by reference. Other suitable lubricants include polydimethylsiloxane gums, aminosilicones, phenylsilicones, polydimethyl siloxane, polydiethylsiloxane, polymethylphenylsiloxane, polydimethylsiloxane gums, polyphenyl methyl siloxane gums, amodimethicone, trimethylsiloxyamodimethicone, diphenyl-dimethyl polysiloxane gums, and the like. Mixtures of lubricants can also be used. Such suitable lubricants typically comprise about 0.10 wt. % to about 15 wt. %, preferably about 0.1 wt. % to about 10 wt. %, and more preferably about 0.5 wt. % to about 5 wt. % of the total weight of the personal care compositions of the present invention.

Optionally, compositions of the present invention can include an emollient selected from silicone fluids (e.g., volatile silicone oils and non-volatile silicone oils); mineral oils; petrolatums; vegetable oils; hydrogenated vegetable oils; fish oils; fatty alcohols; fatty acids; fatty acid and fatty alcohol esters; alkoxylated fatty alcohols; alkoxylated fatty acid esters; benzoate esters; Guerbet esters; alkyl ether derivatives of polyethylene glycols, such as, for example methoxypolyethylene glycol (MPEG); and polyalkylene glycols; lanolin and lanolin derivatives; waxes; and the like. The emollient can be used alone or in combination with one or more emollients of the present invention. The emollient(s) can be utilized in an amount ranging from about 0.5 wt. % to about 50 wt. % by weight of the total antiperspirant composition in one aspect 0.1 wt. % to 25 wt. % in another aspect, and 5 wt. % to 40 wt. % in a further aspect.

Volatile silicone oils include cyclic and linear polydimethylsiloxanes, low molecular weight organo-functional silicones, and the like. Cyclic volatile silicones (cyclomethicones) typically contain about 3 to about 7 silicon atoms, alternating with oxygen atoms, in a cyclic ring structure. Each silicon atom is typically substituted with two alkyl groups, such as, for example, methyl groups. Volatile linear polydimethylsiloxanes (dimethicones) typically contain about 2 to about 9 silicon atoms, alternating with oxygen atoms in a linear arrangement. Each silicon atom is also substituted with two alkyl groups (the terminal silicon atoms are substituted with three alkyl groups), such as, for example, methyl groups. The linear volatile silicones typically have viscosities of less than about 5 cP at 25° C., while the cyclic volatile silicones typically have viscosities of less than about 10 cP at 25° C. "Volatile" means that the silicone has a measurable vapor pressure, or a vapor pressure of at least 2 mm of Hg at 20° C. Non-volatile silicones have a vapor pressure of less than 2 mm Hg at 20° C. A description of volatile silicones is found in Todd and Byers, Volatile Silicone Fluids for Cosmetics, Cosmetics and Toiletries, Vol. 91, pp. 29-32, 1976, and in Kasprzak, Volatile Silicones, Soap/Cosmetics/Chemical Specialties, pp. 40-43, December 1986, each incorporated herein by reference.

Exemplary volatile cyclomethicones are D4 cyclomethicone (octamethylcyclotetrasiloxane), D5 cyclomethicone (decamethylcyclopentasiloxane), D6 cyclomethicone, and blends thereof (e.g., D4/D5 and D5/D6). Volatile cyclomethicones and cyclomethicone blends are commercially available from G.E. Silicones as SF1173, SF1202, SF1256, and SF1258, Dow Corning Corporation as Dow Corning® 244, 245, 246, 345, and 1401 Fluids. Blends of volatile cyclomethicones and volatile linear dimethicones are also contemplated.

Exemplary volatile linear dimethicones include hexamethyldisiloxane, octamethyltrisiloxane, decamethyltetrasiloxane, dodecamethylpentasiloxane and blends thereof. Volatile linear dimethicones and dimethicone blends are commercially available from Dow Corning Corporation as Dow Corning 200® Fluid (e.g., product designations 0.65 CST, 1 CST, 1.5 CST, and 2 CST) and Dow Corning® 2-1184 Fluid.

Exemplary volatile low molecular weight organo-functional silicones include phenyl trimethicone, caprylyl trimethicone, caprylyl methicone, and hexyl methicone, and blends thereof. Low molecular weight organo-functional silicones are commercially available from Clariant under the trade name Silcare® 41M10, Slicare® 31M60, Silcare® 41M10, and Silcare® 41M15.

The non-volatile silicone oils useful as emollients in the present invention are linear and typically have viscosities of from about 10 cP to about 100,000 cP at 25° C. They typically contain above about 10 dialkyl/diaryl or monoalkyl/monoaryl substituted silicon atoms, alternating with oxygen atoms in a linear arrangement. They include polyalkylsiloxane, polyarylsiloxane, and polyalkylarylsiloxane polymers. Exemplary non-volatile silicone oils include the polydimethylsiloxanes (dimethicones), polydiethylsiloxanes, polymethylphenylsiloxanes, and the like. In one aspect of the invention, the non-volatile silicone oil is selected from a non-volatile polydimethylsiloxane having a viscosity range from about 10 cP to about 100,000 cP at 25° C. Non-volatile dimethicones are commercially available from Dow Corning Corporation as Dow Corning 200® Fluid (product designations 10 CST through 10,000 CST).

Mineral oils and petrolatums include cosmetic, USP and NF grades and are commercially available from Penreco under the Drakeol® and Penreco® trade names.

Exemplary vegetable oils suitable an emollient component in the present invention include but are not limited to peanut oil, sesame oil, avocado oil, coconut oil, cocoa butter, almond oil, safflower oil, corn oil, cotton seed oil, castor oil, olive oil, jojoba oil, palm oil, palm kernel oil, soybean oil, wheat germ oil, linseed oil, sunflower seed oil; and the mono-, di-, and triglycerides thereof, and hydrogenated derivatives thereof; and mixtures thereof. Exemplary mono-, di- and triglycerides are, for example, caprylic triglyceride, capric triglyceride, caprylic/capric triglyceride, and caprylic/capric/lauric triglyceride, caprylic/capric/stearic triglyceride, and caprylic/capric/linoleic triglyceride.

Ethoxylated mono- and diglycerides of the foregoing vegetable oils are also contemplated within the scope of the present invention, such as, for example, PEG-8 Caprylic/Capric Glycerides.

Suitable fatty alcohol emollients include but are not limited to fatty alcohols containing 8 to 50 carbon atoms. Exemplary fatty alcohols include capryl alcohol, pelargonic alcohol, capric alcohol, lauryl alcohol, myristyl alcohol, cetyl alcohol, isocetyl alcohol, stearyl alcohol, isostearyl alcohol, cetearyl alcohol, oleyl alcohol, ricinoleyl alcohol, arachidyl alcohol, icocenyl alcohol, behenyl alcohol, and mixtures thereof.

Suitable fatty acid emollients include but are not limited to fatty acids containing 10 to 50 carbon atoms. Exemplary fatty acids are selected from capric acid, lauric acid, myristic acid, palmitic acid, stearic acid, oleic acid, linoleic acid, arachidic acid, behenic acid, and mixtures thereof.

Suitable fatty acid and fatty alcohol ester emollients include but are not limited to hexyl laurate, decyl oleate, isopropyl stearate, isopropyl isostearate, butyl stearate, octyl stearate, cetyl stearate, myristyl myristate, octyldodecyl stearoylstearate, octylhydroxystearate, diisopropyl adipate, isopropyl myristate, isopropyl palmitate, ethyl hexyl palmitate, isodecyl oleate, isodecyl neopentanoate, diisopropyl sebacate, isostearyl lactate, isostearyl hydroxy stearate, diisostearyl fumarate, lauryl lactate, diethyl hexyl maleate, PPG-14 butyl ether and PPG-2 myristyl ether propionate, ethylhexyl octanoate, cetearyl octanoate, and mixtures thereof.

Alkoxylated fatty alcohols are ethers formed from the reaction of a fatty alcohol with an alkylene oxide, generally ethylene oxide or propylene oxide. Suitable ethoxylated fatty alcohols are adducts of fatty alcohols and polyethylene oxide. In one aspect of the invention the ethoxylated fatty alcohols can be represented by the formula R—$(OCH_2CH_2)_n$—OH wherein R represents the linear or branched aliphatic residue of the parent fatty alcohol and n represents the number of molecules of ethylene oxide. In another aspect of the invention, R is derived from a fatty alcohol containing 8 to 40 carbon atoms. In one aspect n is an integer ranging from 2 to 100, 3 to 80 in another aspect, and 3 to 50 in a further aspect. In a still further aspect, R is derived from a fatty alcohol emollient set forth above. Exemplary ethoxylated fatty alcohols are but are not limited to capryl alcohol ethoxylate, lauryl alcohol ethoxylate, myristyl alcohol ethoxylate, cetyl alcohol ethoxylate, stearyl alcohol ethoxylate, cetearyl alcohol ethoxylate oleyl alcohol ethoxylate, and, behenyl alcohol ethoxylate, wherein the number of ethylene oxide units in each of the foregoing ethoxylates can range from 2 and above in one aspect, and from 2 to about 150 in another aspect. It is to be recognized that the propoxylated adducts of the foregoing fatty alcohols and ethoxylated/propoxylated adducts of the foregoing fatty alcohols are also contemplated within the scope of the invention. More specific examples of alkoxylated alcohols are beheneth 5-30 (the 5-30 meaning the number of repeating ethylene oxide or propylene oxide units), Ceteareth 2-100, Ceteth 1-45, Cetoleth 24-25, Choleth 10-24, Coceth 3-10, C9-11 Pareth 3-8, C11-15 pareth 5-40, C11-21 Pareth 3-10, C12-13 Pareth 3-15, Deceth 4-6, Dodoxynol 5-12, Glycereth 7-26, Isoceteth 10-30, Isodeceth 4-6, Isolaureth 3-6, Isosteareth 3-50, Laneth 5-75, Laureth 1-40, Nonoxynol 1-120, Nonoxynol 5-150, Octoxynol 3-70, Oleth 2-50, Steareth 2-100, Trideceth 2-10, and so on.

Alkoxylated fatty acids are formed when a fatty acid is reacted with an alkylene oxide or with a pre-formed polymeric ether. The resulting product may be a monoester, diester, or mixture thereof. Suitable ethoxylated fatty acid ester emollients suitable for use in the present invention are products of the addition of ethylene oxide to fatty acids. The product is a polyethylene oxide ester of a fatty acid. In one aspect of the invention, the ethoxylated fatty acid esters can be represented by the formula R—$C(O)O(CH_2CH_2O)_n$—H, wherein R represents the linear or branched aliphatic residue of a fatty acid and n represents the number of molecules of ethylene oxide. In another aspect, n is an integer ranging from 2 to 50, 3 to 25 in another aspect, and 3 to 10 in a further aspect. In still another aspect of the invention, R is derived from a fatty acid containing 8 to 30 carbon atoms. In a still further aspect, R is derived from a fatty acid emollient set forth above. It is to be recognized that propoxylated and ethoxylated/propoxylated products of the foregoing fatty acids are also contemplated within the scope of the invention. Exemplary alkoxylated fatty acid esters include but are not limited to capric acid ethoxylate, lauric acid ethoxylate, myristic acid ethoxylate, stearic acid ethoxylate, oleic acid ethoxylate, coconut fatty acid ethoxylate, and polyethylene glycol 400 propoxylated monolaurate, wherein the number of ethylene oxide units in each of the foregoing ethoxylates can range from 2 and above in one aspect, and from 2 to about 50 in another aspect. More specific examples of ethoxylated fatty acids are PEG-8 distearate (the 8 meaning the number of repeating ethylene oxide units), PEG-8 behenate, PEG-8 caprate, PEG-8 caprylate, PEG-8 caprylate/caprate, PEG cocoates (PEG without a number designation meaning that the number of ethylene oxide units ranges from 2 to 50), PEG-15 dicocoate, PEG-2 diisononanoate, PEG-8 diisostearate, PEG-dilaurates, PEG-dioleates PEG-distearates, PEG Ditallates, PEG-isostearates, PEG-jojoba acids, PEG-laurates, PEG-linolenates, PEG-myristates, PEG-oleates, PEG-palmitates, PEG-ricinoleates, PEG-stearates, PEG-tallates, and the like.

Benzoate ester emollients are selected from but not limited to $C_{12}$ to $C_{15}$ alkyl benzoate, isostearyl benzoate, octyl dodecyl benzoate, stearyl benzoate, dipropylene glycol dibenzoate, methyl gluceth-20 benzoate, castor oil benzoate, cetyl ricinoleate benzoate, ethylhexyl hydroxystearate benzoate, dimethicone PEG/PPG-20/23 benzoate, and dimethicone PEG-8 benzoate.

Guerbet ester emollients are formed from the esterification reaction of a Guerbet alcohol with a carboxylic acid. Guerbet ester emollients are commercially available from Noveon, Inc. as G-20, G-36, G-38, and G-66.

Lanolin and lanolin derivatives are selected from lanolin, lanolin wax, lanolin oil, lanolin alcohols, lanolin fatty acids, alkoxylated lanolin, isopropyl lanolate, acetylated lanolin alcohols, and combinations thereof. Lanolin and lanolin derivatives are commercially available from Noveon, Inc. under the following trade names Lanolin LP 108 USP, Lanolin USP AAA, Acetulan™, Ceralan™, Lanocerin™, Lanogel™ (product designations 21 and 41), Lanogene™, Modulan™, Ohlan™, Solulan™ (product designations 16, 75, L-575, 98, and C-24), Vilvanolin™ (product desginations C, CAB, L-101, and P).

Waxes include those derived from plant, animal/insect, mineral, petroleum and synthetic sources. Synthetically modified natural (plant and animal/insect) waxes are also contemplated within the scope of the invention. Exemplary plant derived waxes include but are not limited to bayberry wax, candelilla wax, hydrolyzed candelilla wax, carnauba wax, ethoxylated carnauba wax (e.g., PEG-12 carnauba wax), hydrolyzed carnauba wax, carnauba acid wax, hydrogenated castor wax, esparto wax, hydrogenated Japan wax, hydrogenated jojoba oil, jojoba oil esters, sulfurized jojoba oil, ouricury wax, palm kernel wax, and hydrogenated rice bran wax. Exemplary animal/insect derived waxes include but are not limited to beeswax, oxidized beeswax, ethoxylated beeswax (e.g., PEG-6 beeswax, PEG-8 beeswax, PEG-12 beeswax, PEG-20 beeswax), dimethicone copolyol beeswax esters and dimethiconol beeswax ester (e.g. Bis-Hydroxyethoxypropyl Dimethicone Beeswax Esters, Dimethicone PEG-8 Beeswax, and Dimethiconol Beeswax available from Noveon, Inc. under the Ultrabee® trademark), Chinese wax, shellac wax, spermaceti wax, mink wax, and lanolin wax. Exemplary mineral waxes include but are not limited to ceresin waxes, montan wax, montan acid wax, and ozocerite. Exemplary petroleum waxes include paraffin waxes, microcrystalline waxes, and oxidized microcrystalline waxes. Exemplary synthetic waxes include synthetic beeswax, synthetic candelilla wax, synthetic carnauba wax, synthetic Japan wax, snythetic jojoba oil, polyolefin waxes (e.g., polyethylene wax), ethylene glycol diesters or triesters of fatty acids containing 18 to 40 carbon atoms. Mixtures of two or more of the forgoing waxes and classes of waxes are also contemplated.

Various antiperspirant agents that can be utilized according to the present invention include conventional antiperspirant metal salts and complexes of metal salts. In one aspect of the invention the metal salts and metal salt complexes utilized as the antiperspirant agents are acidic and are based on aluminum and zirconium and combinations thereof. These salts include but are not limited to aluminum halides, aluminum hydroxyhalides, aluminum sulfate, zirconium (zirconyl) oxyhalides, zirconium (zirconyl) hydroxyhalides, and mixtures or complexes thereof. Complexes of aluminum and zirconium salts include aluminum and zirconium salt complexes with amino acids, such as, for example, glycine or complexes with a glycol, such as, for example, propylene glycol (PG) or polyethylene glycol (PEG). Exemplary antiperspirant agents include but are not limited to aluminum chloride, aluminum chlorohydrate, aluminum dichlorohydrate, aluminum sesquichlorohydrate, zirconyl hydroxychloride, aluminum chlorohydrex PEG (aluminum chlorohydrex polyethylene glycol), aluminum chlorohydrex PG (aluminum chlorohydrex propylene glycol), aluminum dichlorohydrex PEG (aluminum dichlorohydrex polyethylene glycol), aluminum dichlorohydrex PG (aluminum dichlorohydrex propylene glycol), aluminum sesquichlorohydrex PEG (aluminum sesquichlorohydrex polyethylene glycol), aluminum sesquichlorohydrex PG (aluminum sesquichlorohydrex propylene glycol), aluminum zirconium trichlorohyrate, aluminum zirconium tetrachlorohyrate, aluminum zirconium pentachlorohyrate, aluminum zirconium octachlorohyrate, aluminum zirconium chlorohydrex GLY (aluminum zirconium chlorohydrex glycine), aluminum zirconium trichlorohydrex GLY (aluminum zirconium trichlorohydrex glycine), aluminum zirconium tetrachlorohyrex GLY (aluminum zirconium tetrachlorohyrex glycine), aluminum zirconium pentachlorohyrex GLY (aluminum zirconium pentachlorohyrex glycine), and aluminum zirconium octachlorohyrex GLY (aluminum zirconium octachlorohyrex glycine). Other antiperspirant agents include ferric chloride and zirconium powder. Mixtures of any of the foregoing antiperspirant agents are also suitable for use in the present invention.

The amount of the antiperspirant agent incorporated into the compositions of the present invention is an amount that is sufficient to reduce the flow of perspiration from the location to which the antiperspirant product is applied, for example to the axillary area of the human body.

Generally, the level of antiperspirant agent utilized in the compositions of the present invention range from about 0.5 wt. % to about 35 wt. % based on the total weight of the composition. In another aspect of the invention, the amount of antiperspirant agent in the composition can range from about 5 wt. % to about 25 wt. %, in a further aspect from about 5 wt. % to about 20 wt. %, and in a still further aspect from about 10 wt. % to about 15 wt. %, based on the total weight of the composition. The foregoing weight percentages are calculated on an anhydrous metal salt basis exclusive of the complexing agent (e.g., glycine or glycol).

Suitable neutralizers include triethanolamine, aminomethyl propanol, ammonium hydroxide, sodium hydroxide, other alkali hydroxides, borates, phosphates, pyrophosphates, cocamine, oleamine, diisopropanolamine, diisopropylamine, dodecylamine, PEG-15 cocamine, morpholine, tetrakis(hydroxypropyl)ethylenediamine, triamylamine, triethanolamine, triethylamine, tromethamine 2-amino-2-(hydroxymethyl)-1,3-propanediol, and the like, and mixtures thereof. Such suitable neutralizers typically comprise about 0 wt. % to about 3 wt. %, preferably about 0.01 wt. % to about 2 wt. %, and more preferably about 0.1 wt. % to about 1 wt. % of the total weight of the personal care compositions of the present invention. The forgoing neutralizers can be employed to neutralize the polymer or adjust the pH of the final formulated composition.

Suitable opacifiers include glycol fatty acid esters; alkoxylated fatty acid esters; fatty acid alcohols; hydrogenated fatty acids, polymeric opacifiers, waxes and oils; kaolin; magnesium silicate; titanium dioxide; silica; and the like, and mixtures thereof. Such suitable opacifiers typically comprise about 0.1 wt. % to about 8 wt. %, preferably about 0.5 wt. % to about 6 wt. %, and more preferably about 1 wt. % to about 5 wt. % of the total weight of the personal care compositions of the present invention.

Suitable pharmaceutical actives useful in the present invention include any chemical substance, material or compound suitable for topical administration to induce any desired local or systemic effect. Such actives include, but are not limited to antibiotics, antiviral agents, analgesics (e.g. ibuprofen, acetyl salicylic acid, naproxen, and the like), antihistamines, anti-inflammatory agents, antipruritics, antipyretics, anesthetic agents, diagnostic agents, hormones, antifungals, antimicrobials, anti-dandruff, cutaneous growth enhancers, pigment modulators, antiproliferatives, antipsoriatics, retinoids, anti-acne medicaments (e.g. benzoyl peroxide, sulfur, and the like), antineoplastics agents, phototherapeutic agents, and keratolytics (e.g. resorcinol, salicylic acid, and the like), botanical extracts, and the like, and mixtures thereof. Botanical extracts are commercially available from Cosmetochem International Ltd., Steinhausen, Switzerland. Such pharmaceutical actives typically comprise about 0.1 wt. % to about 20 wt. % of the total weight of the personal care compositions of the present invention.

Suitable preservatives include polymethoxy bicyclic oxazolidine, methyl paraben, propyl paraben, ethyl paraben, butyl paraben, benzoic acid and the salts of benzoic acid, e.g., sodium benzoate, benzalkonium chloride, benzyltriazole, DMDM hydantoin (also known as 1,3-dimethyl-5,5-dimethyl hydantoin), iodopropynyl butylcarbonate, imidazolidinyl urea, phenoxyethanol, phenoxyethylparaben, methylisothiazolinone, methylchloroisothiazolinone, benzoisothiazolinone, triclosan, sorbic acid, salicylic acid salts, and the like, and mixtures thereof. Such suitable preservatives typically comprise about 0.01 wt. % to about 1.5 wt. %, preferably about 0.1 wt. % to about 1 wt. %, and more preferably about 0.3 wt. % to about 1 wt. % of the total weight of the personal care compositions of the present invention.

Suitable spreading or slip aids include hydroxypropyl methylcellulose, hydrophobically modified cellulosics, xanthan gum, cassia gum, guar gum, locust bean gum, dimethicone copolyols of various degrees of alkoxylation, boron nitride, talc, and the like, and mixtures thereof. Such suitable spreading or slip aids typically comprise about 0.01 wt. % to about 5 wt. %, preferably about 0.1 wt. % to about 3 wt. %, and more preferably about 0.1 wt. % to about 2.0 wt. % of the total weight of the personal care compositions of the present invention.

Suitable sunscreens can be used in safe and photoprotectively effective amounts in the personal care compositions of the present invention. Suitable sunscreens include those set forth in Segarin et al., Cosmetics Science and Technology, Chapter VIII, pages 1890 et seq., as well as 64 Federal Register, Vol. 64, No. 98, pp. 27666-27693, May 21, 1999. Specific suitable sun screening agents include, for example, p-aminobenzoic acid and its salts and derivatives (ethyl, isobutyl, glyceryl esters; p-dimethylaminobenzoic acid; 2-ethylhexyl-N,N-dimethylaminobenzoate); anthranilates (i.e., o-aminobenzoates; methyl, octyl, amyl, menthyl, phenyl, benzyl, phenylethyl, linalyl, terpinyl, and cycohexenyl esters); salicylates (octyl, amyl, phenyl, benzyl, menthyl, glyceryl, and dipropyleneglycol esters); cinnamic acid derivatives (ethylhexyl-p-methoxy; menthyl and benzyl esters, phenyl cinnamonitrile; butyl cinnamoyl pyruvate); dihydroxycinnamic acid derivatives (umbelliferone, methylumbelliferone, methylaceto-umbelliferone); trihydroxycinnamic acid derivatives (esculetin, methylesculetin, daphnetin, and the glucosides, esculin and daphnin); hydrocarbons (diphenylbutadiene, stilbene); dibenzalacetone and benzalacetophenone; naphtholsulfonates (sodium salts of 2-naphthol-3,6-disulfonic and of 2-naphthol-6,8-disulfonic acids); dihydroxy-naphthoic acid and its salts; o- and p-hydroxybiphenyldisulfonates; coumarin derivatives (7-hydroxy, 7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, oleate, and tannate); quinoline derivatives (8-hydroxyquinoline salts, 2-phenyl quinoline); hydroxymethoxy-substituted benzophenones; uric and vilouric acids; tannic acid and its derivatives (e.g. hexaethylether); (butyl carbityl) (6-propyl piperonyl) ether; hydroquinone; benzophenones (oxybenzone, sulisobenzone, dioxybenzone, benzoresorcinol, 2,2',4,4'-tetrahydroxybenzophenone, 2,2'-dihydroxy-4, 4'-dimethoxybenzophenone, octabenzone; 4-isopropyldibenzoylmethane; butylmethoxyldibenzoylmethane; octocrylene; 4-isopropyl-dibenzoylmethane; and camphor derivatives such as methylbenzylidene or benzylidene camphor; and the like, and mixtures thereof. Other sunscreens include the inorganic sunblocks such as titanium dioxide (micronized titanium dioxide, 0.03 microns), zinc oxide, silica, iron oxide and dioxide, and the like, and mixtures thereof with one another and with the aforementioned organic sunscreens. Without being limited by theory, it is believed that these inorganic materials provide a sun screening benefit through reflecting, scattering, and absorbing harmful UV, visible, and infrared radiation. Particularly useful are the sunscreens ethylhexyl-p-methoxycinnamate, octyl salicylate and benzophenone, either alone, as a mixture, or in combination with the physical sunscreen titanium dioxide.

By "safe and photoprotectively" is meant an amount of sunscreen sufficient to provide photoprotection when the composition is applied, but not so much as to cause any side effects such as skin reactions. Suitable sunscreens typically comprise about 0.5 wt. % to about 50 wt. %, preferably about 0.5 wt. % to about 30 wt. %, and more preferably about 0.5 wt. % to about 20 wt. % of the total weight of the skin and hair care compositions of the present invention. Exact amounts will vary depending upon the sunscreen chosen and the desired Sun Protection Factor (SPF).

SPF is a commonly used measure of photoprotection of a sunscreen against erythema. This number is derived from another parameter, the minimal erythemal dose (MED). MED is defined as the least exposure dose at a specified wavelength that will elicit a delayed erythema response. The MED indicates the amount of energy reaching the skin and the responsiveness of the skin to the radiation. The SPF of a particular photoprotector is obtained by dividing the MED of protected skin by the MED of unprotected skin. The higher the SPF, the more effective the agent in preventing sunburn. The SPF value tells how many times longer a person can stay in the sun with use of the sunscreen (compared to the same person with unprotected skin) before that person will experience 1 MED. For example, utilizing a sunscreen with an SPF of 6 will allow an individual to stay in the sun six times longer before receiving MED. As the SPF value of a sunscreen increases, a lesser chance exists for development of tanning of the skin. Commercially available sun screening products have SPF values ranging from 2 to 50.

Suitable viscosity adjusting agents or diluents include isopropyl alcohol, ethanol, sorbitol, propylene glycol, diethylene glycol, triethylene glycol, dimethyl ether, butylene glycol, and the like, and mixtures thereof. Such suitable viscosity adjusters or diluents typically comprise about 0.1 wt. % to about 85 wt. %, in one aspect, about 1 wt. % to about 60 wt. % in another aspect, and about 5 wt. % to about 40 wt. % in a still further aspect of the total weight of the personal care compositions of the present invention.

Skin conditioning polymers include quaternized guar gum, quaternized cellulosics, polyquaternium 4, polyquaternium 7, polyquaternium 10, polyquaternium 11, polyquaternium 39, polyquaternium 44, and the like, and mixtures thereof. Such suitable conditioning agents typically comprise about 0.01 wt. % to about 5 wt. %, preferably about 0.1 wt. % to about 3 wt. %, and more preferably about 0.1 wt. % to about 2 wt. % of the total weight of the skin care compositions of the present invention.

Various vitamins also can be included in the compositions of the present invention. Suitable vitamins include but are not limited to vitamin A, vitamin B, biotin, pantothenic acid, vitamin C, vitamin D, vitamin E, tocopherol acetate, retinyl palmitate, magnesium ascorbyl phosphate, and the like, and derivatives and mixtures thereof.

Suitable rheology modifiers/emulsifiers and texture modifiers include natural, semi-synthetic, and synthetic polymers. Examples of natural and modified natural polymers include polygalactomannan gums and modified polygalactomannan gums such as guar gum and cassia gum, xanthan gums, cellulosics, modified cellulosics, starches, polysaccharides, and the like. Polygalactomannan gums and modified polygalactomannan gums are disclosed in U.S. Pat. No. 4,753,659 and in International Patent Publication Nos. WO2004/113390 and WO2004/112733. Examples of synthetic polymers include polymers and copolymers of acrylic acid crosslinked with polyallylsucrose as described in U.S. Pat. No. 2,798,053 which is herein incorporated by reference, polyacrylates, acrylate copolymers or alkali swellable emulsion acrylate copolymers (e.g., Aculyn® 33, Rohm and Haas; Carbopol® Aqua SF-1, Noveon, Inc.), hydrophobically modified alkali swellable copolymers (e.g., Aculyn 22, Aculyn 28 and Aculyn 38, Rohm and Haas), hydrophobically modified non-ionic polyurethanes (e.g., Aculyn 44, Rohm and Haas), polyethylene oxides (e.g., PEG-90M and PEG-180M, Polyox™ resins from Dow/Amerchol), and the like. Commercially available crosslinked homopolymers of acrylic acid include Carbopol® 934, 940, 941, 956, 980 and 996 carbomers available from Noveon, Inc. Other commercially available crosslinked acrylic acid copolymer rheology modifiers include the Carbopol® Ultrez grade series (Ultrez 10, 20 and 21) and the ETD grade series (ETD 2020 and 2050) rheology modifiers available from Noveon, Inc. Mixtures of the foregoing natural, modified natural and synthetic polymers can also be used. Such suitable rheology modifiers/emulsifiers, alone or in combination, typically comprise about 0.1 wt. % to about 5 wt. %, preferably about 0.3 wt. % to about 3 wt. %, and more preferably about 0.5 wt. % to about 2 wt. % of the total weight of the personal care compositions of the present invention.

The polymers of the present invention that are prepared as aqueous emulsions are particularly useful for water-based formulations, and formulations containing water-miscible auxiliary solvents or diluents, but are not limited thereto. Useful solvents commonly employed are typically liquids, such as water (deionized, distilled or purified), alcohols, fatty alcohols, polyols, and the like, and mixtures thereof. Non-aqueous or hydrophobic auxiliary solvents are commonly employed in substantially water-free products, such as nail lacquers, aerosol propellant sprays, or for specific functions, such as removal of oily soils, sebum, make-up, or for dissolving dyes, fragrances, and the like, or are incorporated in the oily phase of an emulsion. Non-limiting examples of auxiliary solvents, other than water, include linear and branched alcohols, such as ethanol, propanol, isopropanol, hexanol, and the like; aromatic alcohols, such as benzyl alcohol, cyclohexanol, and the like; saturated $C_{12}$ to $C_{30}$ fatty alcohol, such as lauryl alcohol, myristyl alcohol, cetyl alcohol, stearyl alcohol, behenyl alcohol, and the like. Non-limiting examples of polyols include polyhydroxy alcohols, such as glycerin, propylene glycol, butylene glycol, hexylene glycol, $C_2$ to $C_4$ alkoxylated alcohols and $C_2$ to $C_4$ alkoxylated polyols, such as ethoxylated, propoxylated, and butoxylated ethers of alcohols, diols, and polyols having about 2 to about 30 carbon atoms and 1 to about 40 alkoxy units, polypropylene glycol, polybutylene glycol, and the like. Non-limiting examples of non-aqueous auxiliary solvents or diluents include silicones, and silicone derivatives, such as cyclomethicone, and the like, ketones such as acetone and methylethyl ketone; natural and synthetic oils and waxes, such as vegetable oils, plant oils, animal oils, essential oils, mineral oils, $C_7$ to $C_{40}$ isoparaffins, alkyl alkyl carboxylic esters, such as ethyl acetate, amyl acetate, ethyl lactate, and the like, jojoba oil, shark liver oil, and the like. Some of the foregoing non-aqueous auxiliary solvents or diluents may also be conditioners and emulsifiers.

Surfactants are generally employed as cleansing agents, emulsifying agents, stabilizers, foam boosters, structurants, hydrotropes and suspending agents. The dimethicone copolyol polymers of the present invention may be employed in formulations containing all classes of surfactants, i.e., anionic surfactants, cationic surfactants, nonionic surfactants, amphoteric surfactants. The term "amphoteric surfactant" as used herein includes zwitterionic surfactants. In addition to the foregoing references, discussions of the classes of surfactants are in Cosmetics & Toiletries® C&T Ingredient Resource Series, "Surfactant Encyclopedia", 2nd Edition, Rieger (ed), Allured Publishing Corporation (1996); Schwartz, et al., Surface Active Agents, Their Chemistry and Technology, published 1949; and Surface Active Agents and Detergents, Volume II, published 1958, Interscience Publishers; each incorporated herein by reference.

Anionic surfactants include substances having a negatively charged hydrophobe or that carry a negative charge when the pH is elevated to neutrality or above, such as acylamino acids, and salts thereof, for example, acylglutamates, acyl peptides, sarcosinates, and taurates; carboxylic acids, and salts thereof, for example, alkanolic acids and alkanoates, ester carboxylic acids, and ether carboxylic acids; phosphoric acid ester and salts thereof; sulfonic acids and salts thereof, for example, acyl isethionates, alkylaryl sulfonates, alkyl sulfonates, and sulfosuccinates; and sulfuric acid esters, such as alkyl ether sulfates and alkyl sulfates.

Non-limiting examples of anionic surfactants include mono-basic salts of acylglutamates that are slightly acidic in aqueous solution, such as sodium acylglutamate and sodium hydrogenated tallow glutamate; salts of acyl-hydrolyzed protein, such as potassium, palmitoyl hydrolyzed milk protein, sodium cocoyl hydrolyzed soy protein, and TEA-abietoyl hydrolyzed collagen; salts of acyl sarcosinates, such as ammonium myristoyl sarcosine, sodium cocoyl sarcosinate, and TEA-lauroyl sarcosinate; salts of sodium methyl acyltaurates, such as sodium lauroyl taurate, sodium methyl oleyl taurate and sodium methyl cocoyl taurate; alkanoic acids and alkanoates, such as fatty acids derived from animal and vegetable glycerides that form water-soluble soaps and water-insoluble emulsifying soaps, including sodium stearate, ammonium stearate, aluminum stearate, and zinc undecylenate; ester carboxylic acids, such as dinonoxynol-9-citrate; salts of acyl lactylates such as calcium stearoyl lactylate and laureth-6 citrate; ethercarboxylic acids derived from ethyoxylated alcohols or phenols having varying lengths of polyoxyethylene chains, such as nonoxynol-8 carboxylic acid, and sodium trideceth-13 carboxylate; mono- and di-esters of phosphoric acid and their salts, such as phospholipids, dilaureth-4-phosphate, DEA-oleth-10 phosphate and triethanolamine lauryl phosphate; salts of acylisethionate, such as sodium cocoyl isethionate; alkylarylbenzene sulfonates, such as alpha-olefin sulfonates (AOS) and alkali metal, alkaline earth metal, and alkanolamine salts thereof, and sodium dodecylbenzene sulfonate; alkyl sulfonates, such as sodium $C_{12}$ to $C_{14}$ olefin sulfonate, sodium $C_{14}$ to $C_{16}$ olefin sulfonate, sodium cocomonoglyceride sulfonate, sodium $C_{12}$ to $C_{15}$ pareth-15 sulfonate, and sodium lauryl sulfoacetate; sulfosuccinates, such as mono- and di-esters of sulfosuccinic acid, salts thereof and alkoxylated alkyl and alkylamido derivatives thereof, such as di-$C_4$ to $C_{10}$ alkyl sodium sulfosuccinate, disodium laureth sulfosuccinate, disodium oleamido MEA-sulfosuccinate, and disodium $C_{12}$ to $C_{15}$ pareth sulfosuccinate; alkyl ether sulfates, such as sodium and ammonium lauryl ether sulfate (having about 1 to about 12 moles ethylene oxide), e.g., sodium laureth sulfate; alkyl sulfates, such as sodium, ammonium and triethanolamine salts of $C_{12}$ to $C_{18}$ alkylsulfates, sodium $C_{12}$ to $C_{14}$ olefin sulfates, sodium laureth-6 carboxylate, sodium $C_{12}$ to $C_{18}$ pareth sulfate, and the like.

Cationic surfactants can have a hydrophobe that carries a positive charge or that is uncharged at pH values close to neutrality or lower, such as alkylamines, alkyl imidazolines, ethoxylated amines, and quaternary ammonium compounds. Cationic surfactants used in cosmetics are preferably N-derivatives and the neutralizing anion may be inorganic or organic. Among the cationic surfactant materials useful herein are quaternary ammonium compounds corresponding to the general formula: $(R^{14}R^{15}R^{16}R^{17}N^+)$ $E^-$, wherein each of $R^{14}$, $R^{15}$, $R^{16}$, and $R^{17}$ are independently selected from an aliphatic group having from 1 to about 30 carbon atoms, or an aromatic, alkoxy, polyoxyalkylene, alkylamido, hydroxyalkyl, aryl or alkylaryl group having 1 to about 22 carbon atoms in the alkyl chain; and $E^-$ is a salt-forming anion such as those selected from halogen, (e.g. chloride, bromide), acetate, citrate, lactate, glycolate, phosphate, nitrate, sulfate, and alkylsulfate. The aliphatic groups can contain, in addition to carbon and hydrogen atoms, ether linkages, ester linkages, and other groups such as amino groups. The longer chain aliphatic groups, e.g., those of about 12 carbons, or higher, can be saturated or unsaturated.

Alkylamines can be salts of primary, secondary and tertiary fatty $C_{12}$ to $C_{22}$ alkylamines, substituted or unsubstituted, and substances sometimes referred to as "amidoamines". Non-limiting examples of alkyl amines and salts thereof include dimethyl cocamine, dimethyl palmitamine, dioctylamine, dimethyl stearamine, dimethyl soyamine, soyamine, myristyl amine, tridecyl amine, ethyl stearylamine, N-tallowpropane diamine, ethoxylated stearylamine, dihydroxy ethyl stearylamine, arachidylbehenylamine, dimethyl lauramine, stearylamine hydrochloride, soyamine chloride, stearylamine formate, N-tallowpropane diamine dichloride, and amodimethicone (INCI name for a silicone polymer and blocked with amino functional groups, such as aminoethylamino propylsiloxane). Non-limiting examples of amidoamines and salts thereof include stearamido propyl dimethyl amine, stearamidopropyl dimethylamine citrate, palmitamidopropyl diethylamine, and cocamidopropyl dimethylamine lactate. Other cationic surfactants include distearyldimonium chloride, dicetyldimonium chloride, guar hydroxypropyltrimonium chloride, and the like. At low pH, amine oxides may protonate and behave similarly to N-alkyl amines.

Non-limiting examples of alkyl imidazolines include alkyl hydroxyethyl imidazoline, such as stearyl hydroxyethyl imidazoline, coco hydroxyethyl imidazoline, ethyl hydroxymethyl oleyl oxazoline, and the like. Non-limiting examples of ethyoxylated amines include PEG-cocopolyamine, PEG-15 tallow amine, quaternium-52, and the like.

Quaternary ammonium compounds are monomeric or polymeric materials containing at least one nitrogen atom that is linked covalently to four alkyl and/or aryl substituents, and the nitrogen atom remains positively charged regardless of the environmental pH. Quaternary ammonium compounds comprise a large number of substances that are used extensively as surfactants, conditioners, antistatic agents, and antimicrobial agents and include, alkylbenzyldimethyl ammonium salts, alkyl betaines, heterocyclic ammonium salts, and tetraalkylammonium salts. Long-chain (fatty) alkylbenzyldimethyl ammonium salts are preferred as conditioners, as antistatic agents, and as fabric softeners, discussed in more detail below. Other quaternary ammonium compounds include quaternary ammonium silicones.

Non-limiting examples of alkylbenzyldimethylammonium salts include stearalkonium chloride, benzalkonium chloride, quaternium-63, olealkonium chloride, didecyldimonium chloride, and the like. Alkyl betaine compounds include alkylamidopropyl betaine, alkylamidopropyl hydroxysultaine, and sodium alkylamido propyl hydroxyphostaine. Non-limiting examples of alkyl betaine compounds include oleyl betaine, coco-betaine, cocamidopropylbetaine, coco-hydroxy sultaine, coco/oleamidopropyl betaine, coco-sultaine, cocoamidopropylhydroxy sultaine, and sodium lauramidopropyl hydroxyphostaine. Heterocyclic ammonium salts include alkylethyl morpholinium ethosulfate, isostearyl ethylimidonium ethosulfate, and alkylpyridinium chlorides, and are generally used as emulsifying agents. Non-limiting examples of heterocyclic ammonium salts include cetylpyridinium chloride, isostearylethylimidonium ethosulfate, and the like. Non-limiting examples of tetraalkylammonium salts include cocamidopropyl ethyldimonium ethosulfate, hydroxyethyl cetyldimonium chloride, quaternium-18, and cocodimonium hyroxypropyl hydrolyzed protein, such as hair keratin, and the like.

Suitable amphoteric or zwitterionic surfactants for use in the present compositions include those broadly described as derivatives of aliphatic quaternary ammonium, phosphonium, and sulfonium compounds, wherein which the aliphatic radicals can be straight chain or branched, and wherein one of the aliphatic substituents contains about 8 to about 30 carbon atoms and another substituent contains an anionic water-solubilizing group, such as carboxy, sulfonate, sulfate, phosphate, phosphonate, and the like. Classes of zwitterionics include alkylamino sulfonates, alkyl betaines and alkylamido betaines, such as stearamidopropyldimethylamine, diethylaminoethylstearamide, dimethylstearamine, dimethylsoyamine, soyamine, myristylamine, tridecylamine, ethylstearylamine, N-tallowpropane diamine, ethoxylated (5 moles ethylene oxide) stearylamine, dihydroxy ethyl stearylamine, arachidylbehenylamine, and the like. Some suitable betaine surfactants include but are not limited to alkyl betaines, alkyl amidopropyl betaines, alkyl sulphobetaines, alkyl glycinates, alkyl carboxyglycinates, alkyl amphopropionates, alkyl amidopropyl hydroxysultaines, acyl taurates, and acyl glutamates, wherein the alkyl and acyl groups have from 8 to 18 carbon atoms. Non-limiting examples of preferred amphoteric surfactants include cocamidopropyl betaine, sodium cocoamphoacetate, disodium cocoamphodiacetate, cocamidopropyl hydroxysultaine, and sodium cocoamphopropionate, which are particularly suitable as mild-type cleansers for skin and hair.

Nonionic surfactants are generally uncharged amphiphiles and usually are alkoxylated to varying degrees. Classes of nonionic surfactants include alcohols, alkanolamides, amine oxides, alkyl glucosides, esters, and ethers. Nonionic alcohols are usually hydroxy derivatives of long-chain $C_8$ to $C_{18}$ alkane hydrocarbons, such as cetearyl alcohol, hydrogenated tallow alcohol, lanolin alcohols, alkanolamides, and the like. Alkanolamides contain at least one alkoxyl or one polyoxyethylene grouping and include alkanol-derived amides, such as acylamide DEA, N-alkyl pyrrolidone, palmamide MEA, peanutamide MIPA, and the like and ethoxylated amides, such as PEG-50 tallow amide. Amine oxides include alkylamine oxides, such as lauramine oxide; and acylamidopropyl morpholine oxides, such as cocamidopropylamine oxide; and the like. The alkyl glucosides include linear and branched $C_4$ to $C_{24}$ alkyl glucosides, such as for example nonyl, decyl, dodecyl and lauryl glycoside. Esters include ethoxylated carboxylic acids, such as PEG-8 dilaurate, PEG-8 laurate, and the like; ethoxylated glycerides, such as PEG-4 castor oil, PEG-120 glyceryl stearate, triolein PEG-6 esters, and the like; glycol esters and derivatives thereof, such as glycol stearate SE, propylene glycol ricinoleate, and the like; monoglycerides, such as glyceryl myristate, glyceryl palmitate lactate, and the like; polyglyceryl esters, such as polyglyceryl-6-distearate, polyglyceryl-4 oleyl ether, and the like, polyhydric alcohol esters and ethers, such as methyl gluceth-20 sesquistearate, sucrose distearate; and the like; sorbitan/sorbitol esters, such as polysorbate-20, polysorbate-60, sorbitan sequiisostearate, and the like; and triesters of phosphoric acid, such as trideceth-3 phosphate, trioleth-8 phosphate, and the like. Exemplary ethers include ethoxylated alcohols, such as, Ceteareth-10, Ceteth-10, Ceteth-20, Isoceteth-20, Steareth-10, Steareth-16, Steareth-20, Steareth-25, Oleth-2, Oleth-10, Oleth-20, nonoxynol-9, and the like; ethoxylated lanolin, such as PEG-20 lanolin, PPG-12-PEG-65 lanolin oil, and the like; ethoxylated polysiloxanes, such as dimethicone copolyol, and the like; propoxylated POE ethers, such as meroxapol 314, poloxamer 122, PPG-5-ceteth-20, and the like; and alkyl polyglycosides, such as lauryl glucose, and the like.

Nonionic surfactants can be used as gelling agents, stabilizers, emulsifiers, suspending agents, solubilizers, foam boosters, and in some cases, as hydrotropes. Non-limiting examples of generally preferred nonionic surfactants include linear or branched alcohol ethoxylates, $C_8$ to $C_{12}$ alkylphenol alkoxylates, such as octylphenol ethoxylates, polyoxyethylene polyoxypropylene block copolymers, and the like; $C_8$ to $C_{22}$ fatty acid esters of polyoxyethylene glycol mono- and di-glycerides; sorbitan esters and ethoxylated sorbitan esters; $C_8$ to $C_{22}$ fatty acid glycol esters; block copolymers of ethylene oxide and propylene oxide; and the like. Non-limiting examples of surfactant boosters or hydrotropes include alkanolamides, such as acetamide MEA, monoethanolamide, diethanolamide, lauramide DEA, cocamide MEA, cocamide DEA, isopropanolamide, and the like; amine oxides, such as hydrogenated tallowamine oxide; short chain alkyl aryl sulfonates, such as sodium toluene sulfonate; sulfosuccinates, such as disodium stearyl sulfosuccinate; and the like.

The cationic polymer embodiments of the present invention are surprisingly compatible with cationic surfactants and other cationic compounds suitable as antistatic agents. The term "antistatic agents" refers to ingredients that alter the electrical properties of cosmetic raw materials or of human body surfaces (skin, hair, etc.) and textiles, for example, by reducing their tendency to acquire an electrical charge and thus, can condition hair, skin, fiber and fabrics. The cationic compatibility of the cationic polymer embodiment makes them suitable for incorporation into formulations containing antistatic agents typically employed in hair care compositions, such as shampoos, post-shampoo conditioning rinses, leave-on products sura as hair sprays, hair dressings and the like. The antistatic agent can be employed in amounts up to about 30 wt. % of the final composition, but is not limited thereto.

Antistatic agents include, but are not limited to, quaternary ammonium compounds, protein derivatives, synthetic quaternary ammonium polymers, amines, protonated amine oxides, betaines, silicones and silicone derivatives, and the like, which may act as antistatic agents in specific formulations and under controlled pH conditions in addition to any surfactant properties imparted by such materials. In addition to antistatic agents previously discussed, non-limiting examples of quaternary ammonium compounds useful as antistatic agents are acetamidopropyl trimonium chloride, behenamidopropyl dimethylamine, behenamidopropyl ethyldimonium ethosulfate, behentrimonium chloride, cetethyl morpholinium ethosulfate, cetrimonium chloride, cocoamidopropyl ethyldimonium ethosulfate, dicetyldimonium chloride, dimethicone hydroxypropyl trimonium chloride, hydroxyethyl behenamidopropyl dimonium chloride, quaternium-26, quaternium-27, quaternium-53, quaternium-63, quaternium-70, quaternium-72, quaternium-76 hydrolyzed collagen, PPG-9 diethylmonium chloride, PPG-25 diethylmonium chloride, PPG-40 diethylmonium chloride, stearalkonium chloride, stearamidopropyl ethyl dimonium ethosulfate, steardimonium hydroxypropyl hydrolyzed wheat protein, steardimonium hydroxypropyl hydrolyzed collagen, wheat germamidopropalkonium chloride, wheat germamidopropyl ethyldimonium ethosulfate, amodimethicone, and the like.

Synthetic quaternary ammonium polymers include film-forming polymers and conditioning polymers. Non-limiting examples of synthetic quaternary ammonium polymers include polymers and copolymers of dimethyl diallyl ammonium chloride, such as polyquaternium-4, polyquaternium-6, polyquaternium-7, polyquaternium-22, polyquaternium-10, polyquaternium-11 polyquaternium-15, polyquaternium-16, polyquaternium-24, polyquaternium-28, polyquaternium-32, polyquaternium-33, polyquaternium-35, polyquaternium-37, polyquaternium-39, polyquaternium-44, polyquaternium-55, polyquaternium-60, polyquaternium-65, polyquaternium-67, polyquaternium-68, PEG-2-cocomonium chloride, quaternium-52, and the like.

The term "hair setting composition" or "hair styling composition" encompasses products comprising at least one polymer of the present invention as a hair setting agent, which are applied to the hair (wet or dry) before, during or after configuring the hair into the shape (curly or straight) desired, without limitation as to product form.

The polymers of the present invention are surprisingly useful in hair setting and hair styling compositions as the sole film-forming, rheology modifying, conditioning fixative, conditioning agent or can be utilized in combination with an auxiliary rheology modifying agent. The polymers of the present invention are also useful in combination with commercially available auxiliary hair fixative polymers, such as nonionic, anionic, cationic, and amphoteric hair setting polymers, cationic conditioning polymers, structurants, and combinations thereof to enhance hair setting and hair styling characteristics. Conventional polymeric hair fixative and hair styling polymers, well known in the art, include natural gums and resins and neutral or anionic polymers of synthetic origin. Listings of commercially available hair fixative and conditioning fixative polymers can be readily found in the INCI Dictionary, CTFA (Cosmetic, Toiletry and Fragrance Association) listings, in supplier websites, and in the trade literature. See, for example, the Polymer Encyclopedia published in Cosmetics & Toiletries®, 117(12), December 2002 (Allured Publishing Corporation, Carol Stream, Ill.), the relevant disclosures of which are incorporated herein by reference.

Suitable commercially available nonionic polymers (i.e., neutral) used as hair styling or fixative polymers include, without limitation, polyvinylpyrrolidone (PVP), polyvinylpyrrolidone/vinylacetate copolymer (PVP/VA), VP/methacrylamide/vinyl Imidazole copolymer (Luviset® Clear, BASF), carbohydrates (e.g. monosaccharides, disaccharides, and polysaccharides), and the like.

Suitable anionic fixative polymers (i.e., supplied in pre-neutralized form or formed in situ by base neutralization) are disclosed in U.S. Pat. No. 6,410,005, and International Patent Application No. WO 03/061615 which are incorporated herein by reference. Such fixative polymers are commercially available from Noveon, Inc., Cleveland, Ohio, and are marketed under the trademarks Fixate® G-100 (supplied in neutralized form), INCI Nomenclature: AMP-acrylates/allyl methacrylate copolymer and Fixate® PLUS (supplied as a low pH emulsion), INCI Nomenclature: polyacrylate-14.

Other examples of anionic fixative polymers are acrylates copolymer (Luviflex Soft and Luvimer from BASF; Avalure® AC series from Noveon, Inc.), and PEG/PPG-25/25 dimethicone/acrylates copolymer (Luviflex® Silk, BASF) and acrylamide/sodium acryloyldimethyltaurate/acrylic acid copolymer (Acudyne® SCP, Rohm and Haas), methacrylic acid/sodium acrylamidomethyl propane sulfonate copolymer (Fixomer®, Nalco), and dehydroxanthan gum (Amaze™, National Starch).

Commercially available cationic fixative polymers include, without limitation thereto, polymers having the INCI name, polyquaternium, such as polyquaternium-4, a diallyldimonium chloride/hydroxyethylcellulose copolymer (such as CELQUAT® H-100, National Starch); polyquaternium-11, a quaternized vinyl pyrrolidone/dimethylaminoethyl methacrylate copolymer (such as GAFQUAT® 734, 755, 755N, ISP); polyquaternium-16, a quaternized vinyl pyrrolidone/vinylimidazolium chloride copolymer (such as LUVIQUAT® FC-370, BASF); polyquaternium-28, a vinylpyrrolidone/methacrylamidopropyltrimethylammonium chloride copolymer (such as GAFQUAT® HS-100, ISP); polyquaternium-46, a quaternized vinylcaprolactam/vinylpyrrolidone/methylvinylimidazolium methosulfate copolymer; polyquaternium-55, a quaternized vinylpyrrolidone/dimethylaminopropylmethylacrylamide/lauryldimethyl-propylmethacrylamidoammonium chloride copolymer (such as STYLEZE™ W-20, ISP), polyquaternium-68, a quaternized vinylpyrrolidone/methylacrylamide/vinylimidazole and 3-methyl-1-vinylimidazolium methylsulfate (such as Luviquat® Supreme, BASF), and the like; and amino-substituted polymers which are cationic under acidic pH conditions, such as vinylcaprolactam/PVP/dimethylaminoethylmethacrylate copolymer (such as GAFFIX® VC-713, ISP); VP/dimethylaminoethylmethacrylate copolymer (such as Copolymer 845, ISP), PVP/DMAPA acrylates copolymer (such as STYLEZE™ CC-10, ISP), the pyrrolidone carboxylic acid salt of chitosan, having the INCI name, Chitosan PCA (such as KYTAMER® PC, Amerchol), and the like.

Suitable amphoteric fixative polymers include, without limitation thereto, octylacryamide/acrylates/butylaminoethylmethacrylate copolymer (such as the AMPHOMER® polymers, National Starch), acrylates/lauryl acrylate/stearyl acrylate/ethylamine oxide methacrylate copolymers (such as the DIAFORMER® polymers from Clariant Corp., and Yokoformer™ from Mitsubishi Chemical Corporation), and the like.

Suitable commercial conditioning polymers include polymeric quaternary ammonium salts such as, without being limited thereto, polyquaternium-7, a polymeric quaternary ammonium salt of acrylamide and dimethyl diallylammonium chloride monomers (such as MACKERNIUM™-007, McIntyre Group, Ltd.); polyquaternium-10, a polymeric quaternary ammonium salt of hydroxyethylcellulose reacted with a trimethylammonium substituted epoxide (such as the UCARE® Polymers JR, LK, LR, SR series, Amerchol and CELQUAT® SC series, National Starch); polyquaternium-39, a polymeric quaternary ammonium salt of acrylic acid, diallyl dimethylammonium chloride and acrylamide (such as the MERQUAT® and MERQUAT® Plus polymers, Ondeo Nalco); quaternized derivatives of natural gums, e.g., guar hydroxypropyltrimonium chloride (such as the JAGUAR® and JAGUAR® Excel polymers, Rhodia, Inc.), and the like.

The personal care compositions of the present invention, particularly the hair and skin care embodiments, optionally can contain guerbet esters as a sheen and shine enhancing adjuvant. Guerbet esters also provide emollient properties and confer desirable sensory properties such as soft feel and soft, lustrous and healthy appearance. Guerbet esters are obtained from the reaction product of a guerbet alcohol and a fatty acid. Exemplary guerbet esters include octyldodecyl beeswax, octyldodecyl isostearate, octyldodecyl ricinoleate and trioctyldodecyl citrate. Guerbet esters are commercially available from Noveon, Inc. marketed under the Beesbutter® and Ultracas® G-20 and G-66 trademarks.

A number of quaternary ammonium compounds are used for fabric conditioning and fabric care, generally referred to as fabric softening agents, and are typically employed in amounts of up to about 20 wt. % of the total weight of the formulation, but are not limited thereto. Fabric softening agents useful in combination with the cationic polymers of the present invention generally include long-chain alkylated quaternary ammonium compounds such as dialkyldimethyl quaternary ammonium compounds, imidazoline quaternary compounds, amidoamine quaternary compounds, dialkyl ester quat derivatives of dihydroxypropyl ammonium compounds; dialkyl ester quat derivatives of methyltriethanol ammonium compounds, ester amide amine compounds, and diester quat derivatives of dimethyldiethanol ammonium chloride, as described in the review article by Whalley, Fabric Conditioning Agents, HAPPI, pp. 55-58 (February 1995), incorporated herein by reference.

In addition to the previously discussed antistatic agents, non-limiting examples of dialkyldimethyl quaternary ammonium compounds, include N,N-dioleyl-N,N-dimethylammonium chloride, N,N-ditallowyl-N,N-dimethylammonium ethosulfate, N,N-di(hydrogenated-tallowyl)-N,N-dimethylammonium chloride, and the like. Non-limiting examples of imidazoline quaternary compounds include 1-N-methyl-3-N-tallowamidoethylimidazolium chloride, 3-methyl-1-tallowylamidoethyl-2-tallowylimidazolinium methylsulfate, available from Witco Chemical Company under the tradename VARISOFT® 475, and the like. Non-limiting examples of amidoamine quaternary compounds include N-alkyl-N-methyl-N,N-bis(2-tallowamidoethyl)ammonium salts where the alkyl group can be methyl, ethyl, hydroxyethyl, and the like. Non-limiting examples of dialkyl ester quat derivatives of dihydroxypropyl ammonium compounds include 1,2-ditallowoyloxy-3-N,N,N-trimethylammoniopropane chloride, 1,2-dicanoloyloxy-3-N,N,N-trimethylammoniopropane chloride, and the like.

In addition, other types of long chain (e.g. natural oil and fatty acid-derived) alkylated quaternary ammonium compounds are suitable fabric softening agents, including, but not limited, to N,N-di(alkyloxyethyl)-N,N-dimethylammonium salts such as N,N-di(tallowyloxyethyl)-N,N-dimethylammonium chloride, N,N-di(canolyloxyethyl)-N,N-dimethylammonium chloride, and the like; N,N-di(alkyloxyethyl)-N-methyl-N-(2-hydroxyethyl)ammonium salts such as N,N-di(tallowyloxyethyl)-N-methyl-N-(2-hydroxyethyl) ammonium chloride, N,N-di(canolyloxyethyl)-N-methyl-N-(2-hydroxyethyl)ammonium chloride, and the like; N,N-di (2-alkyloxy-2-oxoethyl)-N,N-dimethylammonium salts, such as N,N-di(2-tallowyloxy-2-oxoethyl)-N,N-dimethylammonium chloride, N,N-di(2-canolyloxy-2-oxoethyl)-N, N-dimethylammonium chloride, and the like; N,N-di(2-alkyloxyethylcarbonyloxyethyl)-N,N-dimethylammonium salts, such as N,N-di(2-tallowyloxyethylcarbonyloxyethyl)-N,N-dimethylammonium chloride, N,N-di(2-canolyloxyethylcarbonyloxyethyl)-N,N-dimethylammonium chloride, and the like; N-(2-alkanoyloxy-2-ethyl)-N-(2-alkyloxy-2-oxoethyl)-N,N-dimethyl ammonium salts, such as N-(2-tallowoyloxy-2-ethyl)-N-(2-tallowyloxy-2-oxoethyl)-N,N-dimethyl ammonium chloride, N-(2-canoloyloxy-2-ethyl)-N-(2-canolyloxy-2-oxoethyl)-N,N-dimethyl ammonium chloride, and the like; N,N,N-tri(alkyloxyethyl)-N-methyl ammonium salts, such as N,N,N-tri(tallowyloxyethyl)-N-methylammonium chloride, N,N,N-tri(canolyloxyethyl)-N-methylammonium chloride, and the like; N-(2-alkyloxy-2-oxoethyl)-N-alkyl-N,N-dimethyl ammonium salts, such as N-(2-tallowyloxy-2-oxoethyl)-N-tallowyl-N,N-dimethyl ammonium chloride, N-(2-canolyloxy-2-oxoethyl)-N-canolyl-N,N-dimethyl ammonium chloride, and the like.

Preferably, the long-chain alkyl groups are derived from tallow, canola oil, or from palm oil, however, other alkyl groups derived from soybean oil and coconut oil, for example, are also suitable, as are lauryl, oleyl, ricinoleyl, stearyl, palmityl, and like fatty alkyl groups. The quaternary ammonium salt compounds can have any anionic group as a counter-ion, for example, chloride, bromide, methosulfate (i.e. methylsulfate), acetate, formate, sulfate, nitrate, and the like.

Examples of preferred quaternary ammonium fabric softening compounds include N-methyl-N,N-bis(tallowamidoethyl)-N-(2-hydroxyethyl)ammonium methylsulfate and N-methyl-N,N-bis(hydrogenated-tallowamidoethyl)-N-(2-hydroxyethyl)ammonium methylsulfate, each of which materials are available from Witco Chemical Company under the trade names VARISOFT® 222 and VARISOFT® 110, respectively; dialkyl esterquat derivatives of methyltriethanol ammonium salts such as the DEHYQUART® AU series of bis(acyloxyethyl)hydroxyethylmethylammonium methosulfate esterquats available from Cognis, such as DEHYQUART® AU35, AU46, AU56, and the like; and N,N-di (tallowoyloxyethyl)-N,N-dimethylammonium chloride, where the tallow chains are at least partially unsaturated. Other preferred fabric softening agents include the well-known dialkyldimethyl ammonium salts such as N,N-ditallowyl-N,N-dimethyl ammonium methylsulfate, N,N-di(hydrogenated-tallowyl)-N,N-dimethyl ammonium chloride, N,N-distearyl-N,N-dimethyl ammonium chloride, N,N-dibehenyl-N,N-dimethylammonium chloride, N,N-di(hydrogenated tallow)-N,N-dimethyl ammonium chloride (trade name ADOGEN® 442), N,N-ditallowyl-N,N-dimethyl ammonium chloride (trade name ADOGEN® 470, PRAEPAGEN® 3445), N,N-distearyl-N,N-dimethyl ammonium chloride (trade name AROSURF® TA-100), all available from Witco Chemical Company; N,N-dibehenyl-N,N-dimethyl ammonium chloride, sold under the trade name KEMAMINE® Q-2802C by Humko Chemical Division of Witco Chemical Corporation; and N,N-dimethyl-N-stearyl-N-benzylammonium chloride sold under the trade names VARISOFT® SDC by Witco Chemical Company and AMMONYX® 490 by Onyx Chemical Company.

Any of the foregoing fabric softening agents, and mixtures thereof, can be utilized in combination with the polymers of the present invention, particularly in laundry and fabric care products. For ester-containing fabric softening agents, the pH of the compositions can influence the stability of the fabric softening agents, especially in prolonged storage conditions. The pH, as defined in the present context, is measured in the neat compositions at about 20° C. In one embodiment, the pH of the composition is less than about 6. In another embodiment, the pH is in the range of from about 2 to about 5, and in another embodiment from about 2.5 to about 3.5.

In addition to protein derivatives previously described, non-limiting examples of protein derivatives include cocodimonium hydroxypropyl hydrolyzed casein, cocodimonium hydroxypropyl hydrolyzed collagen, cocodimonium hydroxypropyl hydrolyzed hair keratin, cocodimonium hydroxypropyl hydrolyzed rice protein, cocodimonium hydroxypropyl hydrolyzed silk, cocodimonium hydroxypropyl hydrolyzed soy protein, cocodimonium hydroxypropyl hydrolyzed wheat protein, cocodimonium hydroxypropyl hydrolyzed silk amino acids, hydroxypropyl trimonium hydrolyzed collagen, hydroxypropyl trimonium hydrolyzed keratin, hydroxypropyl trimonium hydrolyzed silk, hydroxypropyl trimonium hydrolyzed rice bran, hydroxypropyl trimonium hydrolyzed soy protein, hydroxypropyl trimonium hydrolyzed vegetable protein, hydroxypropyl trimonium hydrolyzed wheat protein, soyethyldimonium ethosulfate, soyethyl morpholinium ethosulfate, and the like.

A pH adjusting agent can be added either to a previously acid-swollen, base swollen or water-swollen polymer or to a formulation containing a polymer embodiment of the invention. Thus, the pH adjusting agent can be utilized in any amount necessary to obtain a desired pH value in the final composition. Non-limiting examples of alkaline pH adjusting agents include alkali metal hydroxides, such as sodium hydroxide, and potassium hydroxide; ammonium hydroxide; organic bases, such as triethanolamine, diisopropylamine, dodecylamine, diisopropanolamine, aminomethyl propanol, cocamine, oleamine, morpholine, triamylamine, triethylamine, tromethamine (2-amino-2-hydroxymethyl)-1,3-propanediol), and tetrakis(hydroxypropyl)ethylenediamine; and alkali metal salts of inorganic acids, such as sodium borate (borax), sodium phosphate, sodium pyrophosphate, and the like, and mixtures thereof. Acidic pH adjusting agents can be organic acids, including amino acids, and inorganic mineral acids. Non-limiting examples of acidic pH adjusting agents include acetic acid, citric acid, fumaric acid, glutamic acid, glycolic acid, hydrochloric acid, lactic acid, nitric acid, phosphoric acid, sodium bisulfate, sulfuric acid, tartaric acid, and the like, and mixtures thereof.

The polymers of the present invention can be used as a thickener, film former, or as a dye or pigment suspending agent for promoting deposition of colorants on hair and skin. Colorants for hair can be temporary, semipermanent or permanent hair dyes or color restorers that pigment the hair gradually. Temporary and semipermanent hair dyes typically are rinses, gels, sprays, shampoos, sticks, and the like, and hair color restorers are typically in the form of hair dressings or emulsions. Permanent hair dyes, and longer-lasting semipermanent hair dyes, are generally two-part products, one part containing the oxidative dye intermediates and dye couplers, and the other part containing stabilized oxidizing agent, usually hydrogen peroxide at about pH 3-4, and are mixed together immediately before use. It is known that such two-part hair dyeing products are formulated with combinations of surfactant ingredients, usually nonionic surfactants or anionic surfactants, to thicken when the dye mixture is prepared. In addition to the foregoing literature, a general discussion of hair dyeing chemistry and compositions is in Brown et al, SCC Monograph, "Permanent Hair Dyes", Society of Cosmetic Chemists (1996), incorporated herein by reference. The polymers of the present invention may be incorporated in one or both of the two-parts of such hair dyeing systems, either as the thickener for the acidic stabilized oxidizing portion or in the non-oxidizing portion to be thickened upon mixing with the acidic portion.

In addition to ingredients discussed above, other ingredients commonly used for antiacne products, facial and body hair bleaches, and antiseptic products include oxidizing agents, such as hydrogen peroxide, benzoyl peroxide, and water-soluble inorganic persulfate compounds such as ammonium persulfate, potassium persulfate, and sodium persulfate.

The polymers of the present invention are useful stabilizers of silicone fluids, which are commonly used in shampoo products, such as the so-called "two-in-one" combination cleansing/conditioning shampoos. Silicone fluids are generally described as alkylsiloxane polymers. The most common class of silicone polymers are the linear polydimethyl siloxanes having the general formula $CH_3-(Si(CH_3)_2-O)_w-Si(CH_3)_3$ where w denotes an integer greater than 2. Silicones can also be branched materials wherein one or more alkyl groups in a polymer are replaced with oxygen to create a branch point. Silicone fluids are typically water-insoluble oils having a viscosity in the range of a few mPa·s to several hundred thousand mPa·s.

A particularly useful class of silicones for use in hair care products are the so-called rigid silicones (also known as silicone gums), as described, for example in U.S. Pat. No. 4,902,499, incorporated herein by reference, which generally have a viscosity (at about 20° C.) of greater than about 600,000 mPa·s and have a weight average molecular weight of at least about 500,000 Daltons as determined by intrinsic viscosity measurement. The polymers of the present invention are surprisingly effective for stabilizing two-in-one type shampoo formulations containing rigid silicone conditioning agents.

Another class of silicone materials that are particularly useful in combination with the polymers of the present invention is the volatile silicones, which are often used as lubricants in hair care products, such as shampoos. Volatile silicones include cyclic and linear polydimethylsiloxanes, and the like. Cyclic volatile silicones typically contain about 3 to about 7 silicon atoms, alternating with oxygen atoms, in a cyclic ring structure. Each silicon atom is also substituted with two alkyl groups, typically methyl groups. Linear volatile silicones are silicone fluids, as described above, having viscosities of not more than about 25 mPa·s. A description of volatile silicones is found in Todd and Byers, Volatile Silicone Fluids for Cosmetics, Cosmetics and Toiletries, Vol. 91, pp. 29-32, 1976, and in Kasprzak, Volatile Silicones, Soap/Cosmetics/Chemical Specialties, pp. 40-43, December 1986, each incorporated herein by reference.

Other silicone oils include the dimethicone copolyols, which are linear or branched copolymers of dimethylsiloxane (dimethicone) and alkylene oxides and can be functionalized through a hydroxyl group on a terminal alkylene oxide unit. The dimethicone polyols can be random or block copolymers. A generally useful class of dimethicone polyols is block copolymers having blocks of polydimethylsiloxane and blocks of polyalkylene oxide, such as blocks of polyethylene oxide, polypropylene oxide, or both. Silicone fluids, including volatile silicones, silicone gums, and silicone copolymers, are available from a variety of commercial sources such as Dow Corning, General Electric Company, and Noveon, Inc.

Other oily materials that are useful in combination with the polymers of the present invention include, for example, acetylated lanolin alcohols; lanolin alcohol concentrates; esters of lanolin fatty acids such as the isopropyl esters of lanolin fatty acid; polyol fatty acids; ethoxylated alcohols, such as ethoxylate and castor oils; sterols; sterol esters; sterol ethoxylates; and like materials Many of such esters and ethoxylates are also useful as non-ionic surfactants.

Numerous ingredients are known in the art as conditioning agents for hair or skin, and humectants, and in addition to those previously discussed, non-limiting examples include PCA (DL-pyrrolidone carboxylic acid) and its salts, such as lysine PCA, aluminum PCA, copper PCA, chitosan PCA, and the like, allantoin; urea; hyaluronic acid and its salts; ceramides; sorbic acid and its salts; sugars and starches and derivatives thereof; lactamide MEA; and the like.

While overlapping weight ranges for the various components and ingredients that can be contained in the compositions of the invention have been expressed for selected embodiments and aspects of the invention, it should be readily apparent that the specific amount of each component in the surfactant containing composition will be selected from its disclosed range such that the amount of each component is adjusted such that the sum of all components in the composition will total 100 wt. %. The amounts employed will vary with the purpose and character of the desired product and can be readily determined by one skilled in the formulation arts and from the literature.

It is also to be recognized that the choice and amount of ingredients in personal care, home care, institutional and industrial care compositions that include the polymers of the invention can vary depending on the intended product and its function, as is well known to those skilled in the formulation arts. An extensive listing of ingredients and their conventional functions and product categories have been disclosed and can be readily ascertained from the literature.

The following examples are presented for the purpose of illustrating the invention disclosed herein in greater detail. However, the examples are not to be construed as limiting the invention in any manner. Unless otherwise specified all parts are given by weight and the term "level" means wt. %.

Methods Description

Clarity

When reported, the clarity of the polymer-containing composition was measured in % T (transmittance) by Brinkmann PC 920 calorimeter at least about 24 hours after the composition was made. Clarity measurements were taken against deionized water (clarity rating of 100%). Compositions having a clarity of about 60% or more were substantially clear; compositions having a clarity in the range of about 45 to 59% were judged substantially translucent.

High Humidity Curl Retention (HHCR) Test

The resistance of a polymer fixative composition to high humidity (about 90% Relative Humidity (RH)) is measured by its ability to hold a curl set on hair after absorption of water from the applied composition and from the surrounding atmosphere employing the well known technique commonly referred to as high humidity curl retention (HHCR). Descriptions of the HHCR methodology are readily found in the cosmetic literature (see, for example, Ch. 30, Harry's Cosmeticology, 8th Ed., M. J. Rieger, Ph.D. (ed.), pp. 666-667, Chemical Publishing Co., Inc., New York, N.Y., 2000, and Diaz et al., J. Soc. Cosmet. Chem., 34, pp. 205-212, July 1983, the relevant disclosures of each are incorporated herein by reference.

Tresses of commercially blended untreated (virgin) human hair are prepared employing natural brown or black color European and/or Oriental hair supplied by International Hair Importers and Products Inc., New York. Each hair tress (about 2.5 grams weight) is about 7.5 inches in length and is crimped (by the root portion) within a metal clamp equipped with a wire hanger loop. Prior to use, each tress is washed with a dilute aqueous solution of sodium lauryl sulfate (10% SLS) followed by thorough rinsing with deionized water at ambient room temperature. The tresses are dried by towel blotting. The initial extended length of the hair tress ($L_e$) is measured and recorded. Varying amounts of polymer fixative composition to be evaluated are applied to each hair tress. The polymer fixative composition to be evaluated is applied to the hair tress and distributed uniformly from the root portion of the hair to tip portion. The treated hair tress is wrapped around a hair curler having an outer diameter of about 3 cm and dried for 12 hours at ambient room temperature of about 21 to 23° C. After drying, the curler is carefully removed, leaving the hair tress styled into a single curl, the initial length of the hair curl ($L_i$) is measured and recorded. The curled hair tress is vertically hung in a humidity chamber set at a temperature of about 26° C. and a relative humidity level of 90%.

High humidity curl retention is determined by measuring the length of the hair curl as the curl relaxes. Measurements are taken at selected intervals of time ($L_t$) over a 24 hour continuum of exposure to high humidity. The following equation is used to calculate percent curl retention, relative to the initial curl length ($L_i$) and length of the fully extended hair, before curling ($L_e$):

% Curl Retention=$L_e-L_t/L_e-L_i\times100$

The change in curl length (droop, helix formation) is periodically measured at selected intervals and is monitored over a period of 24 hours. An initial measurement is taken at time zero, followed by measurements at 0.25 hour intervals for the first hour of exposure, followed by measurements taken at 0.5 hour intervals for the second hour of exposure, followed by measurements taken at 1.0 hour intervals for the remaining 22 hours of exposure.

A curl retention of about 70% or more for a minimum period of about 0.75 hours at about 90% RH is a conventional benchmark for good high humidity resistance, and an HHCR greater than 70% after a period of at least about 3 hours is deemed very good to excellent.

High Humidity Spiral Curl Retention Test (HHSCR)

While the humidity resistance of a fixative composition can be evaluated by the HHCR test described above. The HHCR test is performed using regular salon roller type curlers, where the hair overlaps onto itself as it is rolled, which protects the fibers inside the curl from the test environment. The curl retention test can be rendered more stringent by using of spiral curlers. With this modification, hair is rolled into a spiral groove down the length of the curler rod without overlap. Thus, for a spiral curl, the entire length of the hair is fully exposed to the environment.

The same materials, methods, and evaluation techniques outlined for the previously described HHCR test are employed for the HHSCR test except that the hair tress weighs 0.5 g, is 6.5 inches long and is wrapped around a spiral perm rod (Cyber Sprials™ large spiral curling rods, 8 mm inner diameter, 13.5 mm outer diameter, 162 mm length, American Discount Beauty Supply, 269 South Beverly Drive #250, Beverly Hills, Calif.). The results are reported as percent curl retention calculated by the curl retention equation set forth above.

A curl retention of about 70% or more for a minimum period of about 0.75 hours at about 90% RH is a conventional benchmark for good high humidity resistance, and an HHCR greater than 70% after a period of at least about 3 hours is deemed very good to excellent.

High Humidity Stiffness Retention Test (HHSR)

Figure 5:
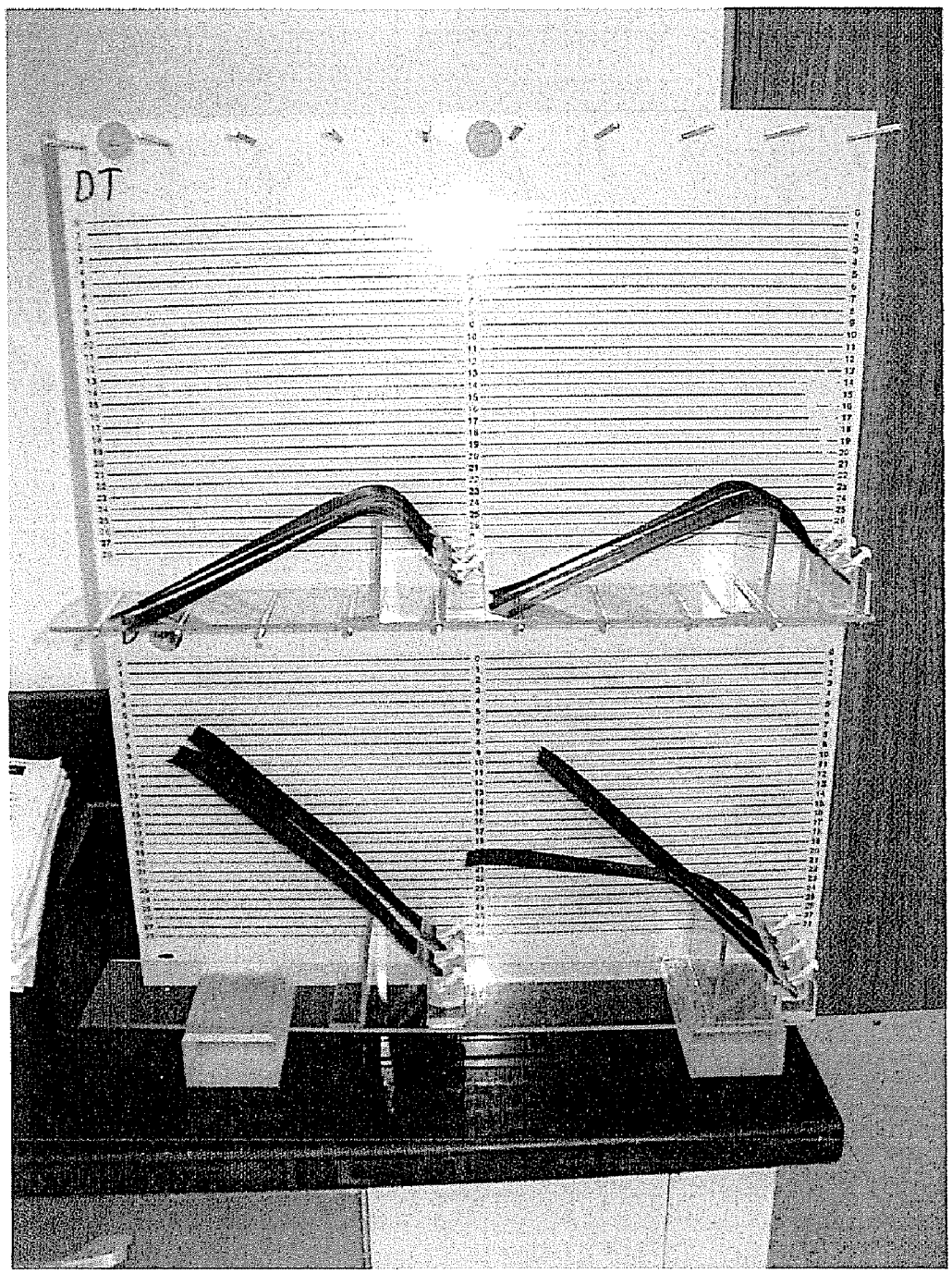
FIG. 5 is a photograph of the measuring apparatus utilized in the High Humidity Stiffness Curl Retention Test (HHSR) showing the hair swatch mounting stand with graduated measurement scale in the background.

The stiffness retention test is conducted by clamping a fixative treated hair swatch (test swatch) on a mounting stand (FIG. 5) that holds the test swatch by the binding at a 45° angle. The mounted test swatch is placed in a humidity chamber set at a temperature of about 26° C. and a relative humidity level of 90%. High humidity stiffness retention is determined by measuring the droop in the test swatch as the hair swatch relaxes upon exposure to the humidity conditions. Measurements are taken at selected intervals of time ($H_t$) over a 24 hour continuum of exposure to high humidity. The following equation is used to calculate percent stiffness retention relative to the initial swatch height ($H_i$) and the height of the swatch taken at each time interval ($H_t$):

% Stiffness Retention=$H_i-H_t/H_i\times100$

The change in swatch height is periodically measured at selected intervals and is monitored over a period of 24 hours. The swatch height is the distance between the bottom of the mounting platform to the tip of the test swatch. An initial measurement is taken at time zero (before humidity exposure), followed by measurements at 0.25 hour intervals for the first hour of exposure, followed by measurements taken at 0.5 hour intervals for the second hour of exposure, followed by measurements taken at 1.0 hour intervals for the remaining 22 hours of exposure.

A stiffness retention value of about 70% or more for a minimum period of about 0.75 hours at about 90% RH is a conventional benchmark for good high humidity resistance, and retention value greater than 70% after a period of at least about 3 hours is deemed very good to excellent.

The test hair swatches (6.5" long, 2.5 g in weight) consisting of virgin European or Asian hair are bound with a flat (sewn and waxed) binding so that the swatch has a uniform rectangular cross section along its whole length (a ribbon-like configuration). The swatches are washed with a stripping shampoo containing 10 wt. % ammonium lauryl sulfate and rinsed with deionized water. A designated amount of experimental fixative is evenly applied to the damp hair swatches. The swatches are laid flat on Teflon® foil to dry at 23° C. and 50% relative humidity for 16 hours.

Mannequin Head Hair Style Screening

To determine the styling efficacy of the fixative polymer gel embodiments of the invention for hard hold, stiffness, and high humidity curl retention properties, the following screening test is conducted:

Natural human hair implanted onto plastic mannequin heads is styled and evaluated according to the procedure below:

1) The hair of each mannequin head is shampooed (Quantum Clarifying Shampoo, Zotos International, Inc.) and is rinsed 3 times with deionized water.

2) The wet hair is parted down the center (from front to rear) of the mannequin head and equal portions of hair are combed away to each side from the center part. Along each side of the part line a grid consisting of 1"×1" squares arranged in two rows of 3 squares each is laid out. Row 1 is parallel to and contiguous with the center part line and Row 2 is parallel to and contiguous with Row 1.

3) On the left side of the center part (looking towards the face of the mannequin head) 3 hair spikes are formed within grid Row 1 while the hair is still wet. The spikes are formed by gathering the hair within a 1"×1" grid section, bundling it into a tress, working a desired amount of the experimental styling composition into the tress until the composition is evenly dispersed onto the hair, and combing the tress of hair upward from the scalp of the mannequin head to the tip of the tress to form a spike. The process is repeated for the remaining two grid sections in the row with the same amount of experimental styling composition worked into each tress.

In Row 2 of the grid, tresses are formed while the hair is still wet and treated in each grid section as described above. Each tress is rolled into a hair roller (plastic snap-on rollers, 5/8" diameter×2¼" long).

4) Step (3) is repeated on the right side of the mannequin head, except that a commercially available polymer fixative is applied to the respective hair tresses for comparative purposes.

5) A rubber band is placed around the untreated hair to hold it in place and the mannequin head is inverted upside down and suspended in a rack allowing the hair spikes to hang freely. The hair is allowed to air dry for 12 hours at room temperature at 50% relative humidity.

6) Upon drying the rollers are removed from the mannequin hair

7) The styled mannequin heads are placed in a humidity chamber set at 35° C. and 90% relative humidity.

8) The mannequin heads are evaluated at 1, 2 and 3 hour intervals to determine stiffness and curl retention.

Mechanical Stiffness Test Method

A TA XTPlus Texture Analyzer (Stable Micro Systems, Surrey, UK) fitted with a rectangular loading nose (3 mm thick×70 mm wide×99 mm high) and a 3-point bending rig is employed to evaluate the mechanical stiffness of a fixative treated hair tress. The texture analyzer is interfaced with a personal computer loaded with Texture Exponent 32 data acquisition software that collects and analysis the data inputted from the instrument. The bending rig consists of two parallel support legs that are spaced apart by approximately 25.4 mm. The treated hair swatch test sample is centered across the span of the support legs and the loading nose which is centered above and between the support legs is pressed through the sample at a rate of 40 mm/s for a distance of 20 mm. Data acquisition starts when the loading nose contacts the sample. The data acquisition software calculates and records the amount of force (Newtons) it takes to deflect the sample through a distance of 20 mm. The results are reported as Peak Force (N).

Hair swatches (6.5" long, 2.5 g in weight) consisting of virgin natural human hair are bound with a flat (sewn and waxed) binding so that the tress has a uniform rectangular cross section along its whole length. The tresses are washed with a stripping shampoo containing 10 wt. % ammonium lauryl sulfate and rinsed with deionized water. A designated amount of experimental fixative is evenly applied to the damp hair swatches. A first set of swatches are laid flat on Teflon® foil to dry at 23° C. and 50% relative humidity in a controlled laboratory environment for 16 hours and tested. A second set of swatches is similarly prepped and placed in a humidity chamber (Espec LHU-113) set at 23° C. and 90% relative humidity for 16 hours and subsequently tested for mechanical stiffness.

A subjective rating is assigned to the specific ranges of Peak Force (N) to classify the stiffness of the fixative polymer as follows:

| Mechanical Stiffness Average Peak Force (Newtons) | Stiffness Subjective Rating |
| --- | --- |
| <1 | Soft, Flexible (untreated hair swatch) |
| <3 | Soft, Flexible Hold |
| 3 to 4 | Soft to Slightly Hard Hold |
| 4 to 5 | Slightly Hard Hold |
| 5 to 6 | Hard Hold |
| 6 to 7 | Very Hard Hold |
| >7 | Super Hard Hold |

Glass Transition Temperature (Tg)

The glass transition temperature (Tg) of the inventive polymers is determined by well known Differential Scanning Calorimetry (DSC) technique.

Turbidity

When reported, the turbidity of a polymer-containing composition was determined in Nephelometric Turbidity Units (NTU) employing a nephelometric turbidity meter with distilled water (NTU=0) as the standard. Compositions having an NTU value of about 90 or greater were judged turbid.

Viscosity

The reported viscosity of each polymer containing composition was measured in milli-Pascal seconds (mPa·s), employing a Brookfield rotating spindle viscometer, (Brookfield, Model RVT) at about 20 revolutions per minute (rpm), at ambient room temperature of about 20 to 25° C. (hereafter referred to as Brookfield viscosity). Viscosity was measured on freshly prepared compositions (referred to as "initial viscosity", and re-measured after allowing the composition to age for at least about 24 hours at ambient room temperature (referred to as "24-hour viscosity"). Where only one viscosity value is shown, the viscosity value is the 24-hour viscosity, unless otherwise indicated.

Yield Value

Yield Value, also referred to as Yield Stress, is herein defined as the initial resistance to flow under stress. It can be measured using a number of techniques, such as via the use of a constant stress rheometer or via extrapolation using a Brookfield viscometer. These techniques and the usefulness of the Yield Value measurement are further explained in Technical Data Sheet Number 244 available from Noveon, Inc., herein incorporated by reference.

| Materials Abbreviations and Trade Names | |
|---|---|
| AA | acrylic acid |
| AAE5P5 | a randomly ethoxylated-5/propoxylated-5 allyl ether (BX-AA-E5P5, Bimax, Inc.) |
| Acudyne ® SCP | acrylamide/acrylamidomethyl propanesulfonic acid (sodium salt)/methacrylic Acid copolymer (Rohm and Haas) |
| AMP-95 | aminomethyl propanol (Angus) |
| AMPS ® monomer | 2-acrylamido-2-methylpropane sulfonic acid |
| APE | allylpentaerythritol |
| Arianor ® Madder Red | basic red 76 dye, CI No. 12245 (Sensient Technologies Corporation) |
| Arianor ® Sienna Brown | basic brown 17 dye, CI No. 12251 (Sensient Technologies Corporation) |
| Arianor ® Steel Blue | basic blue 99 dye, CI No. 56059 (Sensient Technologies Corporation) |
| Arlasolve ™ 200 | isoceteth-20 surfactant (Uniquema) |
| Bam | t-butylacrylamide |
| BEM25 | behenth-25 methacrylate |
| Bio-Terge ® AS-40 | sodium $C_{14}$ to $C_{16}$ olefin sulfonate, 40% surfactant (Stepan Company) |
| Bruggolite ® FF6 | sodium hydroxymethane sulfinate dihydrate - reducing agent (Bruggeman Chemical U.S.) |
| Carbopol ® Ultrez 21 | acrylates/$C_{10}$ to $C_{30}$ alkyl acrylate crosspolymer rheology modifier (Noveon, Inc.) |
| Carbopol ® 940 | crosslinked acrylic acid homopolymer carbomer (Noveon, Inc.) |
| Carbopol ® 980 | crosslinked acrylic acid homopolymer carbomer (Noveon, Inc.) |
| Carbopol ® 996 | crosslinked acrylic acid homopolymer carbomer (Noveon, Inc.) |
| Cetiol ® 868 | octyl stearate (Cognis Corp.) |
| Chemonic ™ OE-2 | oleth-2 emulsifier (Noveon, Inc.) |
| CitA | citraconic anhydride |
| CSEM25 | ceteareth-25 methacrylate |
| DC 193 | PEG-12 dimethicone copolyol (Dow Corning) |
| DC 1401 Fluid | cyclomethicone (and) dimethicone (Dow Corning) |
| DC 1664 | dimethicone (and) laureth-4 (and) laureth-23 emulsion (Dow Corning) |
| DC 1784 | dimethiconol (and) TEA-dodecylbenzene-sulfonate emulsion (Dow Corning) |
| DC 5103 | pendant dimethicone copolyol (PEG-7 dimethicone), MW = 2,500, CAS No. 68937-54-2 (Dow Corning) |
| DMAEMA | N,N'-Dimethylaminoethyl methacrylate |
| Drakeol ® 7 LT | light mineral oil (Penreco) |
| EA | ethyl acrylate |
| Emulgade ® 1000 NI | cetearyl alcohol (and) ceteareth-20 |
| EMULSOGEN ® EPN 407 | secondary $C_{11}$ ethoxylate having 40 ethylene oxide units per alcohol unit (Clariant Corp.) |
| FD&C Blue No. 1 | Hilton Davis (Noveon, Inc.) |
| Finsolv ® TN | $C_{12}$ to $C_{15}$ alkyl benzoate (Fintex Inc.) |
| Fixate ® Plus | polyacrylate-14 (Noveon, Inc.) |
| Fixate ® G100 | AMP-acrylates/allyl methacrylate copolymer (Noveon, Inc.) |
| Gafquat ® 755N | polyquartenium-11 a quaternized copolymer of vinylpyrrolidone and dimethylaminoethyl methacrylate (International Specialty Products Corporation) |
| Glydant Plus ® | blend of 1,3-dimethylol-5,5-dimethyl hydantoin and iodopropynyl butylcarbamate (Lonza Group Ltd.) |
| Germaben ® II | an antimicrobial blend of propylene glycol, diazolidinyl urea, methylparaben and propylparaben (International Specialty Products Corporation) |
| Germaben ® II-E | an antimicrobial blend of propylene glycol (and) diazolidinyl urea (and) methylparaben (and) propylparaben formulated for emulsion systems (International Specialty Products Corporation) |
| Herbasol ® Aloe Vera | *Aloe barbadensis* extract (Cosmetochem International Ltd.) |
| Herbasol ® Chamomile | *Chamomilla recutita* extract (Cosmetochem International Ltd.) |
| Herbasol ® Horsetail | *Equisetum arvense* extract (Cosmetochem International Ltd.) |
| Herbasol ® Stinging Nettle | *Urtica dioica* extract (Cosmetochem International Ltd.) |
| Herbasol ® Tea Tree | *Melaleuca alternifolia* extract (Cosmetochem International Ltd.) |
| Herbasol ® Witch Hazel | *Hamamelis virginiana* extract Cosmetochem International Ltd.) |
| Hostapon ® | sodium methyl oleyl taurate (Clariant) |
| Hydramol ™ PGPL Ester | polyethylene glycol 400 propoxylated monolaurate (Noveon, Inc.) |
| IPA | isopropyl alcohol |
| ItA | itaconic anhydride |
| Kathon ™ CG | methylchloroisothiazolinone (and) methylisothioazolinone |
| Kollidon ® K30 | polyvinylpyrrolidone fixative polymer (BASF Aktiengesellschaft) |
| Lipopearls ™ | vitamin E encapsulated in gelatin beads (Lipo Technologies Inc.) |
| Luperox 11M 75 | t-butyl peroxypivalate free radical initiator (75% solution in odorless mineral sprits) (Atofina) |
| Luviskol ® K90 | polyvinylpyrrolidone fixative polymer (BASF Aktiengesellschaft) |
| Luviskol ® VA 73 | vinylpyrrolidone/vinyl acetate copolymer |
| Luviset ® Clear | copolymer of N-vinylpyrrolidone, methacrylamide and N-vinyl imidazole (BASF Aktiengesellschaft) |
| MAA | methacrylic acid |
| MalA | maleic anhydride |
| MMA | methyl methacrylate |
| Murumuru Butter | *Astrocaryum murumuru* botanical oil (palm) emollient, (Chemyunion Quimica Ltda) |
| Neobee ® M-5 | tri caprylic/capric triglyceride (Stepan Company) |
| Oam | t-octylacrylamide |
| Panthenol | dl-panthenol 50 W (1-Methyl-4 (1 15-dimethyl-1-hydroxyhex-4(5)-enyl)cyclohexene) 50% aqueous solution (BASF Aktiengesellschaft) |
| Plantaren ® 2000 | decyl glucoside (Cognis Care Chemicals) |
| Practice Mannequin Head | implanted with human hair 18-20" long (manufactured by Marianna Industries; purchased from Sally Beauty Company, Inc.) |
| Phenonip ® | antimicrobial blend of methylparaben, ethylparaben, propylparaben, butylparaben and isobutylparaben, (Clariant-Nipa Laboratories) |
| RAL 307 | a randomly ethoxylated-30/propoxylated-5 allyl ether |
| Schercemol ™ DISF | diisostearyl fumarate (Noveon, Inc.) |
| SilSense ™ A-23 | PEG-7 amodimethicone (Noveon, Inc.) |
| SilSense ™ Copolyol-1 | PEG-33 (and) PEG-8 dimethicone (and) PEG-14 (Noveon, Inc.) |
| SilSense ™ Q-Plus | silicone quaternium-8 (dimethicone copolyol quaternized with an alkylamido dimethylamine (Noveon, Inc.) |
| Silsoft ® 305 | pendant dimethicone copolyol (PEG-5/PPG-3 methicone), MW = 600, CAS No. 134180-76-0, (GE Silicones/OSi Specialties) |
| Silsoft ® 475 | pendant dimethicone copolyol (PEG-23/PPG-6 dimethicone), MW = 19,000, CAS No. 68937-55-3, (GE Silicones/OSi Specialties) |
| Silsoft ® 810 | linear dimethicone copolyol (PEG-8 dimethicone), MW = 1,700, CAS No. 102783-01-7, (GE Silicones/OSi Specialties) |
| Silsoft ® 895 | pendant dimethicone copolyol (PEG-17 dimethicone), MW = 5,000, CAS No. 68937-54-2, (GE Silicones/OSi Specialties) |
| Sipomer ® WAM II | methacrylamidoethyl-N-ethylene urea (Rhodia, Inc.) |
| STY | styrene |
| SucA | succinic anhydride |
| TEGDMA | triethylene glycol dimethacrylate |
| Timiron ® Splendid Gold | gold mica cosmetic pigment, (EMD Chemicals Inc. RONA - Cosmetic Business Unit) |
| Timiron ® Diamond Cluster MP-149 | mica/titanium dioxide gray-white glimmering powder (EMD Chemicals Inc. RONA - Cosmetic Business Unit) |
| TMCHMA | trimethyl cyclohexyl methacrylate (Ciba Specialty Chemicals) |
| TMPEO15TA | trimethylolpropane PEG-15 triacrylate |
| TMPTA | trimethylolpropane triacrylate |
| Ultracas ® G-20 | octyldodecyl ricinoleate guerbet ester, (Noveon, Inc.) |

-continued

| Materials Abbreviations and Trade Names | |
|---|---|
| Unispheres ® YE-501 | cosmetic beads containing tocopheryl acetate (and) lactose, cellulose (and) hydroxypropyl methylcellulose (and) iron oxide (Induchem AG) |
| Wecobee ® | hydrogenated vegetable oil (Stepan Company) |
| Zinc Omadine ® | zinc pyrithione (Arch Chemicals, Inc.) |

EXAMPLES SM 1 TO SM 11

A. Dimethicone Copolyol Macromer Synthesis (Without Catalyst)

Dimethicone copolyol macromers (SM) containing terminal and pendant polyether groups conforming to Formulae III, IIIa, IV, and IVa are synthesized by reacting the cyclic anhydrides and the dimethicone copolyols set forth in Table 1A.

A 2 L glass reactor, equipped with a mechanical stirrer, nitrogen inlet, temperature probe connected to an electronic controller, and a water condenser is charged with the respective dimethicone copolyol (Table 1A). Under stirring the copolyol is heated to 80 to 105° C. and stripped under vacuum for 15 minutes to 1 hour. The reactor is cooled to 80 to 85° C., vacuum broken with $N_2$ and then the respective cyclic anhydride (Table 1A) is charged to the reactor. The stirred mixture is heated at 80 to 85° C. for 1 to 3 hours. The mixture is then stripped under vacuum for 15 minutes, vacuum broken with $N_2$, and cooled to 50° C. The mixture is then filtered to remove particulates. In each example, analysis by $^1H$ NMR spectroscopy confirms formation of the respective dimethicone copolyol carboxylate half esters.

B. Dimethicone Copolyol Macromer Synthesis (With Catalyst)

Using a set up identical to the no catalyst synthesis procedure above, dimethicone copolyol and anhydrous alkali metal acetate (0.7 g, 0.2% w/w of total recipe components) are heated to 80° C. under vacuum for 15 minutes. Following backfilling with $N_2$, the mixture is allowed to react with the cyclic anhydride for 1 to 2 hours at 80 to 82° C. Analysis by $^1H$ NMR spectroscopy confirms formation of the respective dimethicone copolyol carboxylate half ester (Table 1B).

TABLE 1A

Macromer Synthesis

| Ex. No. | Dimethicone Copolyol (DMC) | Amount of DMC (g) | Cyclic Anhydride (CA) | OH:CA (equivalents) | Amount of CA (g) |
|---|---|---|---|---|---|
| SM1 | Silsoft 305 | 299.6 | ItA | 1:1 | 54.8 |
| SM2 | Silsoft 810 | 299.7 | ItA | 1:1 | 45.8 |
| SM3 | Silsoft 810 | 300.0 | ItA | 1:0.5 | 23.1 |
| SM4 | Silsoft 810 | 300.0 | CitA | 1:1 | 46.1 |
| SM5 | DC 5103 | 672.1 | MalA | 1:0.75 | 77.9 |
| SM6 (comparative) | Silsoft 475 | 250.0 | SucA | 1:0.5 | 10.1 |
| SM7 | Silsoft 475 | 250.0 | MalA | 1:0.5 | 9.9 |
| SM8 | Silsoft 475 | 250 | ItA | 1:0.25 | 5.72 |
| SM9 | Silsoft 475 | 400 | ItA | 1:0.5 | 18.1 |
| SM9a[1] | Silsoft 475 | 335.9 | ItA | 1:0.5 | 13.4 |
| SM10 | Silsoft 475 | 238.0 | ItA | 1:0.75 | 16.1 |
| SM11 | Silsoft 895 | 470.9 | ItA | 1:0.5 | 29.1 |

[1]Catalyst: Anhydrous potassium acetate at 0.2% w/w of total recipe

TABLE 1B

Macromer Synthesis Product

| Ex. No | Formula | a | b | c | z | R residue source |
|---|---|---|---|---|---|---|
| SM1 | IV | 5 | 3 | 0 | z = y | ItA |
| SM2 | III | 8 | 0 | 0 | z = y | ItA |
| SM3 | III | 8 | 0 | 0 | z ≦ y | ItA |
| SM4 | III | 8 | 0 | 0 | z = y | CitA |
| SM5 | IVa | 7 | 0 | 0 | z ≦ y | MalA |
| SM6 | Comparative | 23 | 6 | 0 | z ≦ y | SucA |
| SM7 | IV | 23 | 6 | 0 | z ≦ y | MalA |
| SM8 | IV | 23 | 6 | 0 | z ≦ y | ItA |
| SM9 | IV | 23 | 6 | 0 | z ≦ y | ItA |
| SM9a | IV | 23 | 6 | 0 | z ≦ y | ItA |
| SM10 | IV | 23 | 6 | 0 | z ≦ y | ItA |
| SM11 | IV | 17 | 0 | 0 | z ≦ y | ItA |

Examples 1 and 2 illustrate the bulk homopolymerization of two olefinically unsaturated dimethicone copolyol macromers (SM) of the invention. One macromer is derived from a substituted cyclic anhydride (i.e., itaconic anhydride) and the other macromer is derived from an unsubstituted cyclic anhydride (i.e., maleic anhydride).

EXAMPLE I

A 100 ml three neck-round bottom flask with magnetic stirring, thermocouple is flushed with nitrogen. The flask is charged with 30 g of the dimethicone copolyol macromer of Example SM 11 (Table 1B). An ammonium persulfate initiator solution (2.6 g in 25 g water) is added in several portions at 4 hour intervals. The reaction was run under continuous stirring at 80 to 85° C. It took 8 hours for approximately 50% of the macromer to convert to the homopolymer and 16 hrs for approximately 70% of the macromer to convert to the homopolymer. $^1H$ NMR analysis from $CDCl_3$ extract of the polymer product indicates that unreacted itaconic anhydride derivatives are in the product.

EXAMPLE II

Example I is repeated with the macromer of Example SM 7 (Table 1B) except that 0.5% of Luperox 11M 75 initiator (based on the total monomer weight) is added to the monomer mixture which is then heated to 60° C. In 10 minutes the reaction mass gels after reaching an exotherm of 72° C. The maleate derivative of DMC is much more reactive than the trisubstituted (methyl) maleate derivative of Example 1. $^1H$ NMR analysis from $CDCl_3$ extract of this gel indicates that only a small portion of unreacted maleic anhydride remains in the reaction product.

The following examples illustrate the copolymerization of olefinically unsaturated dimethicone copolyol macromers (SM) of the invention with other olefinically unsaturated monomers such as AMPS, MMA, MAA and STY utilizing solution and precipitation polymerization techniques.

EXAMPLE III

A 500 ml jacketed reactor equipped with a condenser, thermocouple, mechanical stirring (half moon blade) and nitrogen blanket is charged with 2 parts of the dimethicone copolyol macromer of Example SM 9, 28.5 parts IPA, and 28.5 parts distilled water. Initiator (0.2 parts Luperox 11M75 in 1 part IPA) is injected into the reactor at 72° C. and a mixture of 18 parts AMPS 2405 monomer, 9 parts IPA, and 9 parts distilled water is metered in over 3 hours. An initiator booster (0.02 parts Luperox 11M75 in 1 part IPA) is added every hour after the metering commenced. Addition of booster continued until conversion of all reactants is confirmed by $^1$H NMR. A clear product is obtained by neutralizing with diluted AMP-95. The final product had 21.15% total solids content at pH 4.5.

EXAMPLE IV

A 500 ml jacketed reactor equipped as in Example III is charged with 15 parts of the dimethicone copolyol macromer of Example SM 9a, 380 parts distilled water and 100 parts of IPA. Initiator (0.4 parts Luperox 11M75 in 1 part IPA) is injected into the reactor at 80° C. and a mixture of 40 parts MMA and 20 parts MAA is metered into the reactor through a syringe pump. A mixture of 25 parts AMPS 2405 monomer and 25 parts water is metered into the reactor by another syringe pump over the course of 3 hours. An initiator booster (0.06 parts Luperox 11M75 in 1 part IPA) is added every hour after the metering commenced. The addition of booster continued until conversion of all reactants is confirmed by $^1$H NMR. The final product has a total solids content of 21.94% at pH 8.9 and appears as translucent liquid after stripping of the IPA and neutralizing with AMP-95.

EXAMPLE V

A 500 ml jacketed reactor equipped as in Example IV is charged with 5 parts of the dimethicone copolyol macromer of Example SM 9, 190 parts distilled water and 190 parts of IPA. Initiator (0.4 parts Luperox 11M75 in 1 part IPA) is injected into the reactor at 80° C. and a mixture of 55 parts styrene and 20 parts MAA is metered into the reactor through a syringe pump. A mixture of 20 parts AMPS 2405/10 parts water is injected into the reactor by another syringe pump over the course of 3 hours. An initiator booster (a total of 0.78 parts Luperox 11M75 in 1 part IPA) is added every hour after metering commenced. A polymer solid is obtained and is filtered and washed with 100 g IPA and followed by 50 g IPA/water mixture and then dried. The final product is a white powder.

The following examples illustrate copolymerization of the olefinically unsaturated dimethicone copolyol macromers (SM) of the invention with different types of monomers via anionic emulsion polymerization.

EXAMPLES VI TO VIII

Emulsion polymers are prepared from the monomers set forth in Table 2 as follows: A monomer reaction mixture is prepared in a first reactor equipped with an agitator rotating at about 900 rpm under a nitrogen atmosphere by combining 148 parts by weight of MAA, about 200 parts by weight of EA, and about 40.0 parts by weight of the macromer prepared in Example SM 7 in 192 parts by weight of deionized water containing about 13.3 parts by weight of 30% aqueous sodium lauryl sulfate. To a second reactor equipped with a mixing agitator and nitrogen inlet and feed pumps, is added about 580 parts by weight of deionized water and about 1.27 parts by weight of 30% aqueous sodium lauryl sulfate. The contents of the second reactor are heated with agitation at a rotation speed of about 200 rpm under a nitrogen atmosphere. After the contents of the second reactor reach a temperature in the range of about 85 to 88° C., about 7.84 parts of a 1.73% ammonium persulfate solution (free radical initiator) is injected into the warmed surfactant solution in the second reactor. The aqueous emulsion of the monomer mixture from the first reactor is gradually pumped into the second reactor over a period of about 180 minutes at a temperature in the range of about 85 to 88° C. Simultaneously, an initiator feed about 60 parts by weight of 1.7% ammonium persulfate solution is metered to the reaction mixture in the second reactor and the temperature of the reaction is maintained at about 90° C. for an additional one and half hours to complete polymerization. The resulting emulsion is cooled to room temperature, discharged from the reactor and collected. All three copolymers are analyzed by $^1$H NMR using CDCL$_3$ extract.

TABLE 2

| Ex. No. | MAA (wt. %) | EA (wt. %) | SM (wt. %) | SM Type | $^1$H NMR (CDCl$_3$ extract) |
|---|---|---|---|---|---|
| VI | 37 | 53 | 10 | SM 7 | No free SM 7 |
| VII (comparative) | 37 | 53 | 10 | SM 6 | Free SM 6 |
| VIII | 37 | 53 | 10 | SM 9 | No free SM 9 |

The copolymer of comparative Example VII showed $^1$H NMR peaks corresponding to non-reactive succinate dimethicone copolyol ester which is presumably not incorporated into the copolymer. Surprisingly, the copolymers of Examples VI and VIII containing reactive double bonds did not show a functional ester peak related to unreacted maleate ester derivative (SM 7) or unreacted itaconate derivative of dimethicone copolyol ester (SM 9). These experiments illustrate that the macromers of the invention are readily copolymerizable in emulsion polymerization.

EXAMPLES 1 TO 3

Emulsion polymers are prepared as in Examples VI to VIII utilizing the monomers and macromers set forth in Table 3. Three copolymers were synthesized using a non-reactive dimethicone copolyol (Silsoft® 475) in Example 3, the macromer SM 9 in Example 1, and no silicone additive in Example 2 to observe if incorporating the dimethicone copolyol macromers of the invention into a copolymer backbone has any affect on copolymer properties.

The viscosity of each polymer is measured at 1 and 2 percent solids mucilages neutralized with AMP-95 to pH 7. In addition Tg, clarity and turbidity (NTU) values are measured for each polymer. The results are reported in Table 3A.

TABLE 3

| Ex. No. | MMA level | Bam level | X-linker (level) | CSEM25[1] level | AAE5P5[2] level | MAA level | EA Level | SM Type (level) |
|---|---|---|---|---|---|---|---|---|
| 1 | 10 | 3 | TEGDMA (0.2) | 3 | 2 | 37 | 34.8 | SM 9 (10) |
| 2 (control) | 10 | 3 | TEGDMA (0.2) | 3 | 2 | 37 | 44.8 | No SM |
| 3 (comparative) | 10 | 3 | TEGDMA (0.2) | 3 | 2 | 37 | 34.8 | DMC[3] (10) |

[1]associative monomer
[2]semihydrophobic monomer
[3]Silsoft ® 475 dimethicone copolyol

TABLE 3A

| Ex. No. | Tg | 1% Viscosity (mPa·s) | Clarity (% T) | Turbidity (NTU) | 2% Viscosity (mPa·s) | Clarity (% T) | Turbidity (NTU) |
|---|---|---|---|---|---|---|---|
| 1a | 65 | 1,230 | 98 | 5 | 10,500 | | |
| 2a | 73 | 1,200 | 97 | 1 | 12,500 | 97.0 | 0.77 |
| 3a | 68 | 370 | 100 | 1 | 4,600 | | |

The viscosity efficiency of the polymer of Example 1 is maintained utilizing 10 wt. % of the dimethicone copolyol macromer of the invention. In contrast, the polymer of Example 3, which is made according to the teaching of U.S. Pat. No. 6,403,074 B1 containing 10 wt. % of a non-functionalized dimethicone copolyol has a lower viscosity at both 1 and 2 percent mucilages. The non-functionalized dimethicone copolyol (Silsoft 475) might be acting as chain transfer agent in Example 3a and causing the viscosity deficiency of the resulting associative polymer.

EXAMPLES 4 TO 6

Emulsion polymers are prepared as in Examples VI to VIII utilizing the monomers and macromers set forth in Table 4. The comonomers of Examples 4 and 5 are copolymerized in the presence of olefinically unsaturated dimethicone copolyol macromers of the invention, while the comonomers of comparative Example 6 are polymerized in the presence of a non-reactive (i.e., saturated dimethicone copolyol carboxylate). The polymers are compared for relative viscosity performance.

TABLE 4

| Ex. No. | MMA level | Bam level | X-linker (level) | CSEM25[1] level | AAE5P5[2] level | MAA level | EA level | SM Type (level) |
|---|---|---|---|---|---|---|---|---|
| 4 | 10 | 3 | TEGDMA (0.2) | 3 | 2 | 37 | 41.8 | SM 9 (3) |
| 5 | 10 | 3 | TEGDMA (0.2) | 3 | 2 | 37 | 41.8 | SM 7 (3) |
| 6 (comparative) | 10 | 3 | TEGDMA (0.2) | 3 | 2 | 37 | 41.8 | SM 6 (3) |

[1]hydrophobic monomer
[2]semihydrophobic monomer

The gel properties of each polymer are measured at 1 and 2 percent solids mucilages neutralized with AMP-95 to pH 7. When unsaturated functional dimethicone copolyol macromers (SM 9 and SM 7) are copolymerized into the associative polymer backbone, such polymers overcome the typical viscosity depression phenomenon exhibited by associative polymers containing saturated dimethicone copolyol (SM 6) as shown in Table 4A below. Glass transition and clarity values of the mucilages were maintained.

TABLE 4A

| Ex. No. | Tg | 1% Viscosity (mPa·s) | Clarity (% T) | Turbidity (NTU) | 2% Viscosity (mPa·s) | Clarity (% T) | Turbidity (NTU) |
|---|---|---|---|---|---|---|---|
| 4a | 70 | 700 | 96 | 4 | 8,350 | 94.8 | 1.64 |
| 5a | 69 | 1,000 | 96 | 1 | 7,750 | 94.0 | 0.24 |
| 6a | 69 | 370 | 99 | 1 | 3,800 | 98.0 | 0.53 |

EXAMPLES 7 TO 10

Emulsion polymers are prepared as in Examples VI to VIII utilizing the monomers and macromers set forth in Table 5. In these examples the loading effect of the cyclic anhydride to the dimethicone copolyol in synthesizing the dimethicone copolyol macromer on the gel properties of the final copolymer product is determined and reported in Table 5A.

TABLE 5

| Ex. No. | MMA level | Bam level | X-linker (level) | CSEM25[1] level | AAE5P5[2] level | MAA level | EA level | SM Type (level) |
|---|---|---|---|---|---|---|---|---|
| 7 | 10 | 3 | TMPE015TA (0.25) | 3 | 0 | 40 | 43.8 | none |
| 8 | 10 | 3 | TMPE015TA (0.25) | 3 | 0 | 40 | 40.8 | SM 9 (3) |
| 9 | 10 | 3 | TMPE015TA (0.25) | 3 | 0 | 40 | 40.8 | SM 8 (3) |
| 10 | 10 | 3 | TMPE015TA (0.25) | 3 | 0 | 40 | 40.8 | SM 10 (3) |

[1]associative monomer
[2]semihydrophobic monomer

TABLE 5A

| Ex. No. | Tg | 1% Viscosity (mPa·s) | Clarity (% T) | Turbidity (NTU) | 2% Viscosity (mPa·s) | Clarity (% T) | Turbidity (NTU) |
|---|---|---|---|---|---|---|---|
| 7a | 78 | n/a | n/a | n/a | 9,650 | 97.0 | 0.89 |
| 8a | 77 | n/a | n/a | n/a | 9,750 | 98.0 | 0.43 |
| 9a | 75 | 1,100 | 96 | 0.89 | 1,260 | 98.0 | 0.39 |
| 10a | 74 | 12,280 | 96 | 1.3 | 10,300 | 96.0 | 0.38 |

The gel properties of each polymer are measured at 1 and 2 percent solids mucilages neutralized with AMP-95 to pH 7. From the data in Table 5A polymers polymerized from macromers synthesized from anhydride loading to dimethicone copolyol loadings of between 0.25 to 0.75 equivalents (based on the OH number of the dimethicone copolyol) give optimal gel properties.

EXAMPLES 11 AND 12

Emulsion polymers are prepared as in Examples VI to VIII utilizing the monomers and macromers set forth in Table 6. Two copolymers were polymerized utilizing the monomers and macromers set forth in Table 6. The reactive dimethicone copolyol macromers of Examples SM 5 and SM 7 are synthesized from dimethicone copolyols of differing molecular weights (MW=2,500 and 19,000, respectively). Copolymers synthesized from low and high molecular weight dimethicone copolyol macromers give good sensory and gel properties.

TABLE 6

| Ex. No. | MMA level | Bam level | X-linker (level) | CSEM25[1] level | AAE5P5[2] level | MAA level | EA level | SM Type (level) |
|---|---|---|---|---|---|---|---|---|
| 11 | 10 | 3 | TMPE015TA (0.25) | 3 | 0 | 40 | 40.8 | SM 7 (3) |
| 12 | 10 | 3 | TMPE015TA (0.25) | 3 | 0 | 40 | 40.8 | SM 5 (3) |

[1]associative monomer
[2]semihydrophobic monomer

The gel properties of each polymer are measured at 1 and 2 percent solids mucilages neutralized with AMP-95 to pH 7. The data are presented in Table 6A.

TABLE 6A

| Ex. No. | Tg | 1% Viscosity (mPa·s) | Clarity (% T) | Turbidity (NTU) | 2% Viscosity (mPa·s) | Clarity (% T) | Turbidity (NTU) |
|---|---|---|---|---|---|---|---|
| 11a | n/a | 1,500 | 97.5 | 0.99 | 12,600 | 98 | 0.39 |
| 12a | n/a | 980 | 96 | 0.8 | 8,750 | 96 | 0.65 |

EXAMPLES 13 TO 20

Emulsion polymers are prepared as in Examples VI to VIII utilizing the monomers and macromers set forth in Table 7. Several non-associative copolymers are synthesized utilizing dimethicone copolyol macromers containing terminal and pendant polyether groups that are fully functionalized with an unsaturated carboxylate group (R=R'=cyclic anhydride residue in Formula IIIa; z=y in Formula VIa) or partially functionalized with an unsaturated carboxylate group (one of R or R'=hydrogen in Formula IIIa; z≦y in Formula VIa). The viscosity of each polymer is measured at 1 and 2.5 percent solids mucilages neutralized with AMP-95 to pH 7. In addition Tg, clarity, and turbidity (NTU) values are measured for each polymer. The results are reported in Table 7A.

TABLE 7

| Ex. No. | Acrylate Monomer (level) | Amide Monomer (level) | X-linker (level) | MAA level | EA level | SM (level) |
|---|---|---|---|---|---|---|
| 13 | 0 | 0 | TMPTA (0.3) | 32 | 62.7 | SM 9 (5) |
| 14 | 0 | 0 | TMPTA (0.3) | 35 | 61.7 | SM 9 (3) |
| 15 | 0 | 0 | TMPTA (0.3) | 37 | 59.7 | SM 9 (3) |
| 16 | 0 | Bam (3) | TEGDMA (0.2) | 37 | 56.8 | SM 9 (3) |
| 17 | MMA (20) | Bam (3) | TEGDMA (0.2) | 37 | 36.8 | SM 9 (3) |
| 18 | MMA (15) | Oam (3) | TMPE015TA (0.3) | 40 | 38.7 | SM 9 (3) |
| 19 | MMA (15) | Bam (3) | TMPE015TA (0.3) | 40 | 38.7 | SM 9 (3) |
| 20 | TMCHMA (10) | Bam (3) | TMPE015TA (0.2) | 40 | 43.8 | SM 9 (3) |
| 20a | 0 | 0 | TMPTA (0.3) | 35 | 59.7 | SM 3 (5) |
| 20b | 0 | 0 | TMPTA (0.3) | 35 | 59.7 | SM 4 (5) |
| 20c | 0 | 0 | TMPTA (0.3) | 35 | 59.7 | SM 1 (5) |
| 20d | 0 | 0 | TMPTA (0.3) | 35 | 59.7 | SM 2 (5) |

TABLE 7A

| Ex. No. | Tg | 1% Viscosity (mPa·s) | Clarity (% T) | Turbidity (NTU) | 2.5% Viscosity (mPa·s) | Clarity (% T) | Turbidity (NTU) |
|---|---|---|---|---|---|---|---|
| 13a | 45.6 | 2,660 | N/A | 29.4 | 7,650 | N/A | 9.3 |
| 14a | 54 | 720 | 93 | 5 | 2,400 | 91.0 | 3.10 |
| 15a | 59 | 640 | 95 | 4 | 1,500 | 95.0 | 2.20 |
| 16a | 81 | 105 | 100 | 0.7 | N/A | N/A | N/A |
| 17a | 87 | 57 | 100 | 0.71 | N/A | N/A | N/A |
| 18a | 85 | 280 | 94.0 | 2.27 | 360 | 95.0 | 2.07 |
| 19a | 88 | 220 | 98.0 | 0.59 | 280 | 97.0 | 0.54 |
| 20a | 83 | 200 | 96.0 | 1.53 | 980 | 94.0 | 1.88 |
| 20aa | 56.5 | 3,770 | 87.5 | 14.7 | 7,350 | 83.6 | 14 |
| 20ba | 58.8 | 7,550 | 81.1 | 36.9 | 16,200 | 70.1 | 31 |
| 20ca | N/A | 1,880 | 89.9 | 21.4 | 5,250 | 91.3 | 9.65 |
| 20da | N/A | 1,320 | 92.0 | 10.3 | 4,900 | 84.2 | 13.8 |

EXAMPLES 21 TO 54

Emulsion polymers are prepared as in Examples VI to VIII utilizing the monomers and macromers set forth in Table 8. The viscosity of each polymer is measured at 2, 3, and 5 percent solids mucilages neutralized with AMP-95 to pH 7. In addition Tg, clarity and turbidity (NTU) values are measured for each polymer. The results are reported in Table 8A.

TABLE 8

| Ex. No. | Monomer (level) | Amide (level) | X-linker (level) | CSEM25[1] level | AAE5P5[2] level | MAA level | EA level | SM Type (level) |
|---|---|---|---|---|---|---|---|---|
| 21 | MMA (15) | Bam (3) | TEGDMA (0.2) | 3 | 0 | 40 | 35.8 | SM 9 (3) |
| 22 | MMA (10) | Bam (3) | TEGDMA (0.3) | 1 | 2 | 40 | 40.7 | SM 9 (3) |
| 23 | TMCHMA (10) | Bam (1) | TEGDMA (0.3) | 1 | 0 | 37 | 47.7 | SM 9 (3) |
| 24 | MMA (15) | Oam (3) | TMPEO15TA (0.3) | 1 | 2 | 37 | 38.7 | SM 9 (3) |
| 25 | MMA (10) | Oam (1) | TEGDMA (0.1) | 3 | 2 | 37 | 43.9 | SM 9 (3) |
| 26 | MMA (10) | Oam (3) | TMPEO15TA (0.2) | 1 | 0 | 37 | 45.8 | SM 9 (3) |
| 27 | TMCHMA (15) | Bam (3) | TMPEO15TA (0.3) | 1 | 0 | 40 | 37.7 | SM 9 (3) |
| 28 | TMCHMA (10) | Bam (3) | TEGDMA (0.1) | 3 | 0 | 37 | 43.9 | SM 9 (3) |
| 29 | MMA (15) | Oam (1) | TMPEO15TA (0.1) | 3 | 2 | 37 | 38.9 | SM 9 (3) |
| 30 | TMCHMA (10) | Oam (3) | TMPEO15TA (0.1) | 1 | 2 | 40 | 40.9 | SM 9 (3) |
| 31 | TMCHMA/MMA (5/5) | Bam (3) | TMPEO15TA (0.15) | 1 | 1.8 | 40 | 41.1 | SM 9 (3) |
| 32 | TMCHMA/MMA (5/5) | Bam (3) | TMPEO15TA (0.15) | 1 | 1.8 | 40 | 41.1 | SM 9 (3) |
| 33 | MMA (15) | Oam (3) | TMPEO15TA (0.2) | 1 | 0 | 37 | 40.8 | SM 9 (3) |
| 34 | MMA (10) | Bam (3) | TMPEO15TA (0.25) | 3 | 0 | 40 | 42.8 | SM 9 (1) |
| 35 | n/a | n/a | TMPEO15TA (0.3) | 1 | 0 | 40 | 56.9 | SM 9 (1.8) |
| 36 | MMA (10) | Bam (3) | TMPEO15TA (0.25) | 3 | 0 | 40 | 41.8 | SM 9 (2) |
| 37 | MMA (10) | Bam (3) | TMPEO15TA (0.25) | 3 | 0 | 40 | 40.8 | SM 9 (3) |
| 38 | MMA (10) | Bam (3) | TMPEO15TA (0.25) | 2 | 0 | 40 | 41.8 | SM 9 (3) |
| 39 | MMA (10) | Bam (3) | TMPEO15TA (0.3) | 1 | 0 | 40 | 42.7 | SM 9 (3) |
| 40 | MMA (10) | Bam (3) | TMPEO15TA (0.3) | 1.5 | 0 | 40 | 42.2 | SM 9 (3) |
| 41 | n/a | n/a | TMPEO15TA (0.3) | 1 | 0 | 40 | 55.7 | SM 9 (3) |
| 42 | n/a | Oam (1.8) | TMPEO15TA (0.3) | 1 | 0 | 40 | 53.9 | SM 9 (3) |
| 43 | n/a | Oam (4) | TMPEO15TA (0.3) | 1 | 0 | 40 | 51.7 | SM 9 (3) |
| 44 | WAM II (1.3) | n/a | TMPEO15TA (0.3) | 1 | 0 | 40 | 54.4 | SM 9 (3) |
| 45 | WAM II (2.9) | n/a | TMPEO15TA (0.3) | 1 | 0 | 40 | 52.8 | SM 9 (3) |
| 46 | MMA (52) | n/a | n/a | 0 | 0 | 35 | 10 | SM 9 (3) |
| 47 | MMA (10) | Bam (3) | TEGDMA (0.2) | 6 | 2 | 37 | 38.8 | SM 9 (3) |
| 48 | n/a | n/a | TMPEO15TA (0.3) | 1 | 0 | 40 | 53.7 | SM 9 (5) |
| 49 | n/a | n/a | TMPEO15TA (0.3) | 1 | 0 | 40 | 51.2 | SM 9 (7.5) |
| 50 | n/a | n/a | TMPEO15TA (0.3) | 1 | 0 | 40 | 48.7 | SM 9 (10) |
| 51 | n/a | n/a | TMPEO15TA (0.3) | 1 | 0 | 40 | 53.7 | SM 3 (5) |
| 52 | n/a | n/a | TMPEO15TA (0.3) | 1 | 0 | 40 | 53.7 | SM 4 (5) |
| 53 | n/a | n/a | TMPEO15TA (0.3) | 1 | 0 | 40 | 53.7 | SM 2 (5) |

TABLE 8-continued

| Ex. No. | Monomer (level) | Amide (level) | X-linker (level) | CSEM25[1] level | AAE5P5[2] level | MAA level | EA level | SM Type (level) |
|---|---|---|---|---|---|---|---|---|
| 54 | n/a | n/a | TMPEO15TA (0.3) | 1 | 0 | 40 | 53.7 | SM 1 (5) |

[1]associative monomer
[2]semihydrophobic monomer

TABLE 8A

| Ex. No. | Tg | 2% Viscosity (mPa·s) | Clarity (% T) | Turbidity (NTU) | 3% Viscosity (mPa·s) | Clarity (% T) | Turbidity (NTU) | 5% Viscosity (mPa·s) | Clarity (% T) | Turbidity (NTU) |
|---|---|---|---|---|---|---|---|---|---|---|
| 21a | 84 | 5,600 | 97.0 | 2.07 | 25,600 | 96.0 | 2.92 | 115,000 | 89.0 | 3.95 |
| 22a | 79 | 1,320 | 98.9 | 0.38 | 5,150 | 98.2 | 0.60 | 15,300 | 96.9 | 0.68 |
| 23a | 71 | 1,680 | 96.0 | 3.62 | 9,800 | 94.0 | 5.53 | 52,000 | 90.0 | 8.52 |
| 24a | 78 | 2,740 | 97.0 | 2.00 | 8,700 | 93.0 | 1.77 | 15,000 | 93.0 | 2.28 |
| 25a | 70 | 10,000 | 94.0 | 0.95 | 35,200 | 95.0 | 0.92 | 78,000 | 93.0 | 0.95 |
| 26a | 72 | 1,800 | 99.0 | 0.52 | 5,500 | 98.0 | 0.59 | 14,000 | 97.0 | 0.68 |
| 27a | 91 | 2,680 | 82.0 | 8.40 | 15,500 | 83.0 | 6.48 | 92,000 | 88.0 | 5.77 |
| 28a | 73 | 10,600 | 94.0 | 3.04 | 38,000 | 94.0 | 2.32 | 104,000 | 88.0 | 3.04 |
| 29a | 73 | 14,900 | 98.0 | 0.77 | 40,500 | 91.0 | 100 | 92,000 | 94.0 | 1.20 |
| 30a | 79 | 840 | 97.0 | 1.88 | 5,850 | 96.0 | 1.84 | 30,000 | 93.0 | 3.57 |
| 31a | 76 | 720 | 98 | 0.78 | 2,400 | 97 | 0.98 | 8,250 | 97 | 1.18 |
| 32a | 75 | 540 | 97.0 | 0.77 | 1,900 | 96 | 0.91 | 7,050 | 94 | 1.28 |
| 33a | 78 | 860 | 99.0 | 0.3 | 3,100 | 99.0 | 0.26 | 8,300 | 98.0 | 0.31 |
| 34a | 77 | 10,400 | 97.0 | 0.53 | 32,700 | 96.0 | 0.54 | 104,000 | 95.0 | 0.59 |
| 35a | 60 | 4,980 | 96.0 | 1.01 | 13,500 | 95 | 0.83 | 28,000 | 94 | 0.81 |
| 36a | 77 | 8,250 | 98.0 | 0.33 | 27,900 | 97.0 | 0.38 | 93,000 | 96.0 | 0.56 |
| 37a | 78 | 10,200 | 97.0 | 0.45 | 25,300 | 97.5 | 0.42 | 86,000 | 95 | 0.75 |
| 38a | 84 | 5,400 | 97.5 | 0.48 | 20,900 | 96.5 | 0.67 | 68,000 | 95.5 | 0.6 |
| 39a | 81 | 3,100 | 98.0 | 0.41 | 8,800 | 98 | 0.42 | 29,100 | 96 | 0.99 |
| 40a | 85 | 5,200 | 97.0 | 0.61 | 29,100 | 96 | 0.99 | 75,000 | 94 | 1.28 |
| 41a | 61 | 6,700 | 93.0 | 1.63 | 17,000 | 93 | 1.74 | 49,000 | 90 | 1.93 |
| 42a | 59 | 3,060 | 98.4 | 2.03 | 7,450 | 97.8 | 2.85 | 25,600 | 97.5 | 2.48 |
| 43a | 60 | 2,200 | 98.3 | 1.09 | 5,300 | 98.9 | 1.23 | 14,400 | 96 | 1.77 |
| 44a | 60 | 24,500 | 89.0 | 22.1 | 46,000 | 89.7 | 11.37 | 93,000 | 90 | 6.44 |
| 45a | 60 | 11,800 | 88.5 | 50.1 | 24,500 | 90.1 | 2.81 | 50,500 | 90 | 2.9 |
| 46a | 121 | 1200 | n/a | 83 | n/a | n/a | n/a | n/a | n/a | n/a |
| 47a | 45 | 35,200 | 95.7 | 1.75 | n/a | n/a | n/a | n/a | n/a | n/a |
| 48a | 64.5 | 3,020 | 98.7 | 0.1 | 3,020 | 98.7 | 0.11 | n/a | n/a | n/a |
| 49a | 65.9 | 2,110 | 98 | 0.5 | 2,110 | 98 | 0.54 | n/a | n/a | n/a |
| 50a | 33.3 | 2,110 | 96.1 | 1.3 | 2,110 | 96.1 | 1.28 | n/a | n/a | n/a |
| 51a | 64.5 | 1,220 | 95 | 6.9 | 1,220 | 95 | 6.86 | n/a | n/a | n/a |
| 52a | 66.0 | 1,530 | 95.6 | 6.3 | 1,530 | 95.6 | 6.3 | n/a | n/a | n/a |
| 53a | 68.6 | 5,000 | 97.8 | 3.02 | n/a | n/a | n/a | n/a | n/a | n/a |
| 54a | 68.3 | 9,550 | 99.5 | 3.0 | n/a | n/a | n/a | n/a | n/a | n/a |

EXAMPLES 55 TO 59

Cationic acid-swellable associative emulsion polymers are polymerized from the monomers and macromers set forth in Table 9 according to the following procedure.

A monomer emulsion is prepared by adding (with mixing) the monomers in Table 9 into a reactor containing about 340 parts by weight of water, about 5.5 parts by weight of Emulsogen® EPN 407 nonionic surfactant and about 0.3 parts by weight of sodium lauryl sulfate (30%) anionic surfactant. The resulting mixture is agitated (about 400 rpm) at a temperature in the range of about 20 to about 25° C. under a nitrogen atmosphere until an emulsion is obtained. A solution of about 0.12 parts by weight of Bruggolite® FF6 (reducing agent) in about 5.0 parts by weight of water is then added to the monomer emulsion, with mixing agitation, to initiate the polymerization reaction. A solution of about 0.16 parts by weight of sodium persulfate (oxidizing agent) in about 5.0 parts by weight of water is then added to the monomer emulsion with mixing agitation to initiate the polymerization reaction. The temperature of the reaction mixture is maintained at a temperature in the range of about 60 to about 70° C. for about 2.5 hours after addition of the initiator. Additional quantities of initiator are added at about 0.5 hours and about 1.5 hours after the reaction is initiated (about 0.08 parts by weight of sodium persulfate in about 3.0 parts by weight of water for each additional quantity of initiator added).

The resulting polymer emulsion is cooled to a temperature in the range of about 44 to about 46° C. over a period of about 45 minutes and an oxidizing solution is added to the reaction mixture in two portions at one hour intervals thereafter. Each oxidizing (redox) solution contains about 0.15 parts by weight of t-butylhydroperoxide (70%), about 0.015 parts by weight of sodium lauryl sulfate (30%) and about 0.15 parts by weight of Bruggolite® FF6 reducing agent in about nine parts by weight of water. The polymer emulsions are cooled to ambient room temperature and discharged from the reactor.

TABLE 9

| Ex. No. | TEGDMA level | HEMA level | CSEM25[1] level | RAL 307 level | DMAEMA level | EA level | SM 9 level |
|---|---|---|---|---|---|---|---|
| 55 | 0.1 | 1.8 | 0 | 4 | 35 | 58.1 | 1 |
| 56 | 0.1 | 1.8 | 0 | 4 | 35 | 56.1 | 3 |
| 57 | 0.1 | 1.8 | 0 | 4 | 35 | 49.1 | 10 |
| 58 | 0.1 | 1.8 | 3 | 4 | 35 | 55.1 | 1 |
| 59 | 0.1 | 1.8 | 3 | 4 | 35 | 53.1 | 3 |

[1]associative monomer

The viscosity and clarity properties of each of the polymers are measured at 2 percent total solids mucilages neutralized to Ph 4 with a 50 percent solution of glycolic acid. The results are reported in Table 9A.

TABLE 9A

| Ex. No. | 2% Viscosity (mPa·s) | Yield Value (dynes/cm$^2$) | Turbidity (NTU) |
|---|---|---|---|
| 55a | 11,100 | 1,280 | 7.73 |
| 56a | 11,400 | 1,460 | 8.63 |
| 57a | 9,050 | 1,330 | 9.99 |
| 58a | 17,700 | 2,230 | 5.78 |
| 59a | 16,000 | 1,890 | 4.85 |

EXAMPLE 60

Several hair fixative gel compositions are formulated utilizing the dimethicone copolyol containing polymers, carbomer rheology modifiers, and other components identified in Table 10.

TABLE 10

| Component | Function | Amount |
|---|---|---|
| D.I.[1] water | diluent | q.s. to 100 wt. % |
| dimethicone copolyol polymer | fixative/rheology modifier | 5 wt. % (1.5% polymer solids) |
| carbomer | rheology modifier | 0.5 wt. % |
| Glydant Plus ® | preservative | 0.1 wt. % |
| AMP-95 | neutralizer | to pH 7 |

[1]D.I. = deionized

The gel compositions are formulated as follows: The rheology modifier is dispersed in water and mixed to achieve a uniform dispersion The rheology modifier dispersion is partially neutralized with AMP-95 to pH 6. The dimethicone copolyol polymer emulsions (5 wt. % as supplied or 1.5 wt. % polymer solids) synthesized according to the noted examples in Table 10A are slowly added with thorough mixing to the dispersion and neutralized to a final pH of 7. A preservative is then added to the neutralized composition. Clarity and viscosity values are measured for each gel sample. The results are reported in the table below.

TABLE 10A

| Ex. No. 60 | Polymer Ex. | Polymer Solids | Carbopol ® Rheology Modifier (grade designation) | Rheology Modifier (wt. %) | Viscosity (mPa·s) | Clarity (% T) |
|---|---|---|---|---|---|---|
| A | 23 | 1.5% | Ultrez 21 | 0.5 | 27,700 | 92.7 |
| B | 29 | 1.5% | Ultrez 21 | 0.5 | 50,000 | 96.3 |
| C | 23 | 1.5% | 940 | 0.5 | 16,800 | 79.9 |
| D | 29 | 1.5% | 940 | 0.5 | 36,600 | 92.1 |
| E | 23 | 1.5% | 980 | 0.5 | 13,300 | 78.6 |
| F | 29 | 1.5% | 980 | 0.5 | 39,250 | 95 |
| Control | n/a | n/a | Ultrez 21 | 0.5 | 39,200 | 94.5 |

EXAMPLE 61

A hair fixative composition is formulated from the polymer of Example 24 (2.0 wt. % polymer solids) using the ingredients and procedure set forth in Example 60, except that no rheology modifier is present. For comparative purposes a commercially available fixative polymer, Luviskol® K90 polymer, is similarly formulated (2.0 wt. % polymer solids) except that no neutralization is conducted.

The ability of the fixative formulations to hold a hair style under extreme humidity conditions is evaluated. The hair styles are prepared and evaluated in accord with the Mannequin Head Hair Style Screening Test described above. Two mannequin heads one implanted with Asian hair and the other implanted with Caucasian hair are used in the test. The hair tresses utilized to style the spikes and curls on the Asian hair mannequin head are approximately 2.5" and 4" in length, respectively. The hair tresses utilized to style the spikes and curls on the Caucasian hair mannequin head are approximately 4" and 5" in length, respectively. The hair tresses utilized to style the spikes and curls are on the Asian hair mannequin head are treated with 0.8 g/tress of the experimental and commercial fixative, and the hair tresses utilized to style the spikes and curls are on the Caucasian hair mannequin head are treated with 0.5 g/tress of the experimental and commercial fixative. The Asian hair is naturally courser and denser per unit area of mannequin scalp. Consequently, more fixative is utilized to maintain the initial style.

Figure 1A:
FIG. 1A is a photograph of an Asian hair mannequin head in which one half of the head is styled with a hair fixative composition containing a polymer of the invention and the other half of the head is styled with a commercial fixative composition. The photograph is taken before humidity chamber exposure.
Figure 2:
FIG. 2 is a photograph of the Caucasian hair mannequin head illustrated in FIG. 1 taken after 1 hour in a humidity chamber set at 35° C. and 90% relative humidity.
Figure 2A:
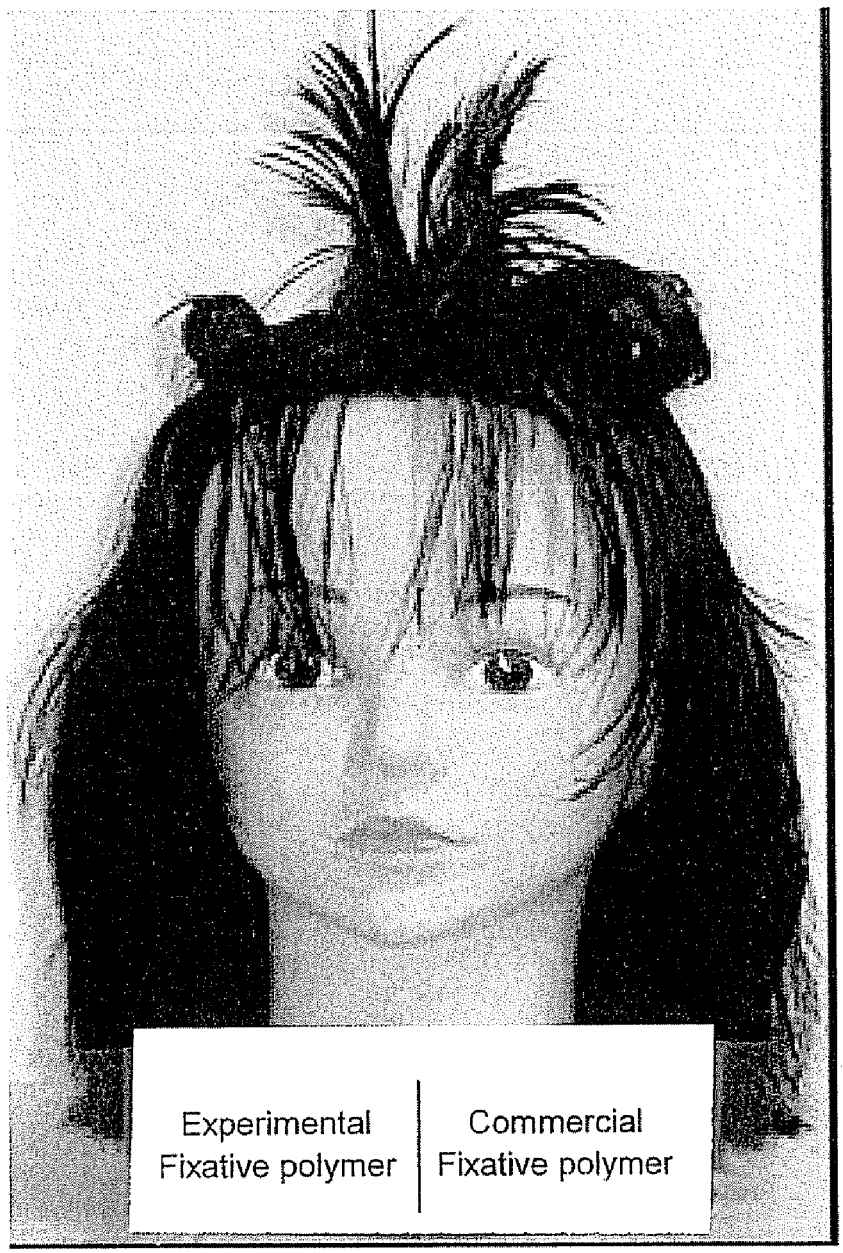
FIG. 2A is a photograph of the Asian hair mannequin head illustrated in FIG. 1A taken after 1 hour in a humidity chamber set at 35° C. and 90% relative humidity.
Figure 3:
FIG. 3 is a photograph of the Caucasian hair mannequin head illustrated in FIG. 1 taken after 2 hours in a humidity chamber set at 35° C. and 90% relative humidity.
Figure 3A:
FIG. 3A is a photograph of the Asian hair mannequin head illustrated in FIG. 1A taken after 2 hours in a humidity chamber set at 35° C. and 90% relative humidity.
Figure 4:
FIG. 4 is a photograph of the Caucasian hair mannequin head illustrated in FIG. 1 taken after 3 hours in a humidity chamber set at 35° C. and 90% relative humidity.
Figure 4A:
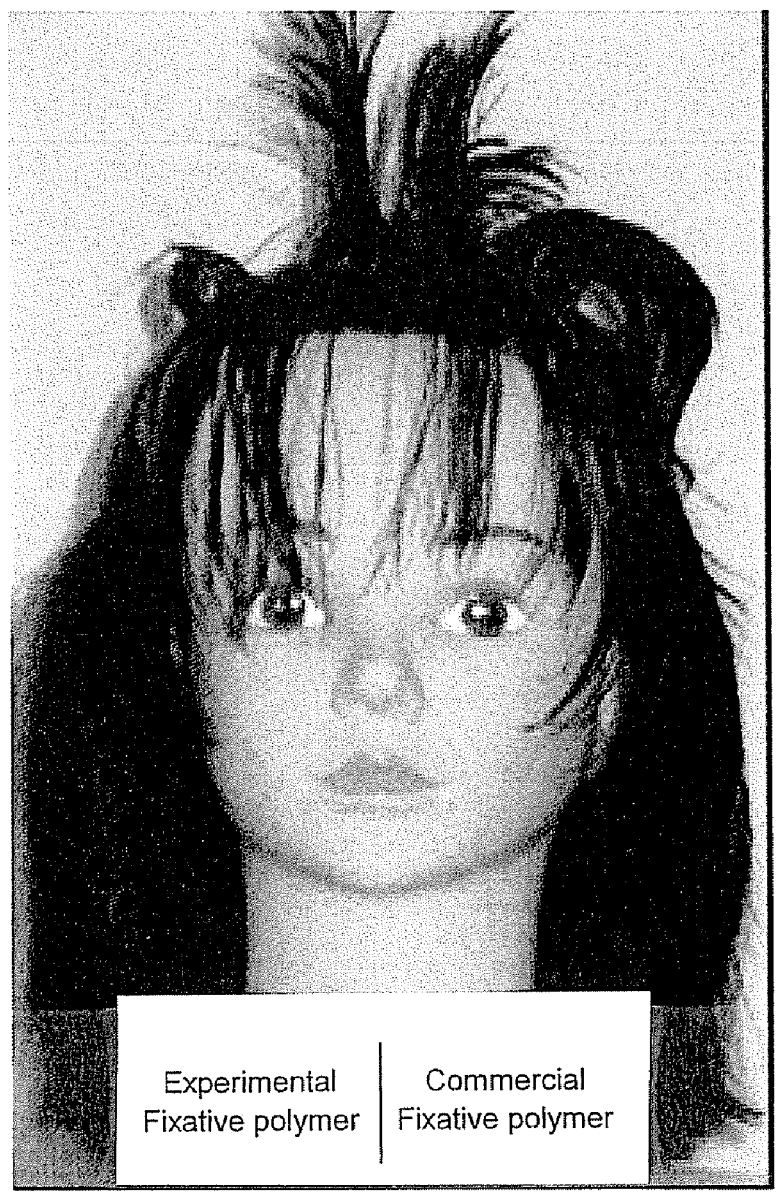
FIG. 4A is a photograph of the Asian hair mannequin head illustrated in FIG. 1A taken after 3 hours in a humidity chamber set at 35° C. and 90% relative humidity.

Upon drying, the styled portions of both mannequin heads are stiff and firm to the touch (FIGS. 1 and 1*a*). Both mannequin heads are placed in a humidity chamber (35° C. @ 95% R.H.) for a period of 3 hours. At one hour intervals each mannequin head is removed from the humidity chamber and each side is evaluated for styling hold retention and photographed (FIGS. 1/1A through 4/4A). From the photographs illustrated in FIGS. 2 and 2A, it is evident that the commercial fixative composition is failing after the first hour of exposure to high humidity conditions as the curls on both of the Caucasian and Asian hair mannequins are unwinding and the spikes on the Asian hair mannequin are beginning to droop.

As illustrated in FIGS. 3, 3A, 4 and 4A, curl and spike retention is maintained after 2 and 3 hour exposure to high humidity conditions for Asian hair and curl retention is demonstrated for Caucasian hair for the polymer of the invention. For the same exposure intervals, the commercial fixative polymer composition does not exhibit any curl retention, while the spikes are beginning lie down.

After the 3 hour humidity chamber exposure, the styles utilizing the polymer of the invention are stiffer, harder and firmer to the touch than the commercial polymer. The style is observed to have good shine and smooth feel.

EXAMPLE 62

The polymers obtained in Examples 4, 21, 23, 25, 30, 35, and 47 are formulated into fixative compositions in accordance with the procedure of Example 60 except that differing gel amounts are indicated in Table 11.

For comparative purposes a commercially available fixative polymer, Luviskol® K90 PVP, is similarly formulated to pH 7. Following formulation, repetitions of the fixative compositions are evaluated for high humidity curl retention via the (HHCR) test described above. The results are illustrated below in Table 11.

dance with the HHSR protocol above. The results are illustrated below in Table 12. The reported stiffness retention values (SR %) represent an average of 5 repetitions for both the experimental fixative and the comparative PVP fixative polymer.

TABLE 12

| Ex. No. | Polymer Ex. | Hair Type | Gel Amount (g) per gram of Hair | 0.75 hr SR % | 1.5 hr SR % | 8 hr SR % | 24 hr. SR % |
|---|---|---|---|---|---|---|---|
| 63[1] | 35 | Asian | 0.20 | 93.7 | 90.9 | 89.6 | 89.6 |
| 63A[1] | PVP | Asian | 0.20 | 88.4 | 85.5 | 82.0 | 81.3 |

[1]Formulated with 0.3 wt. % Carbopol ® Ultrez 21 rheology modifier

TABLE 11

| Ex. No. | Polymer Ex. | Hair Type | Gel Amount (g) per gram of Hair | 0.75 hr CR % | 1.5 hr CR % | 8 hr CR % | 24 hr CR % |
|---|---|---|---|---|---|---|---|
| 32A[1] | 4 | Caucasian | 0.32 | 100 | 99.1 | 97.3 | 97.3 |
| 62B[1] | 4 | Asian | 0.32 | 96.4 | 95.5 | 88.4 | 88.4 |
| 62C[2] | 21 | Asian | 0.32 | 96.2 | 93.9 | 92.0 | 92.0 |
| 62D | 23 | Asian | 0.32 | 100 | 98.1 | 94.7 | 94.7 |
| 62F[2] | 25 | Asian | 0.32 | 98.1 | 95.7 | 93.7 | 93.7 |
| 62G[2] | 30 | Asian | 0.32 | 99.0 | 97.4 | 91.0 | 87.5 |
| 62H[2] | 35[3] | Caucasian | 0.10 | 97.0 | 94.6 | 92.1 | 92.1 |
| 62I[1] | 47 | Caucasian | 0.32 | 99.0 | 97.2 | 96.3 | 96.3 |
| 62J[1] | 47 | Asian | 0.32 | 96.0 | 93.1 | 82.4 | 82.4 |
| 62K[1] | PVP[3] | Caucasian | 0.10 | 91.6 | 68.0 | 32.2 | 22.5 |

[1]Average of 5 repetitions
[2]Average of 9 repetitions
[3]Formulated with 0.3 wt. % Carbopol ® Ultrez 21 rheology modifier

EXAMPLE 63

A fixative gel is prepared from the polymer of Example 35 (3 wt. % polymer solids) according to the procedure outlined in Example 60. Carbopol® Ultrez 21 polymer is utilized as a rheology modifier. For comparative purposes a commercially available fixative polymer, Luviset® Clear fixative polymer (3 wt. % polymer solids), is similarly formulated to pH 7. The experimental gel is prepared, tested and evaluated in accor-

EXAMPLE 64

A fixative gel is prepared from the polymer of Example 35 (2 wt. % polymer solids) according to the procedure outlined in Example 60. Carbopol® Ultrez 21 polymer is utilized as a rheology modifier. For comparative purposes a commercially available fixative polymer, Luviset® Clear fixative polymer (2 wt. % polymer solids) and Luviskol® K90 PVP (2 wt. % polymer solids), are similarly formulated to pH 7. The experimental gel is prepared, tested and evaluated in accordance with the HHSCR protocol above. The results are illustrated below in Table 13. The reported spiral curl retention values (SCR %) represent an average of 5 repetitions for both the experimental fixative and the comparative PVP fixative polymer.

TABLE 13

| Ex. No. | Polymer Ex. | Hair Type | Gel Amount (g) per gram of Hair | 0.75 hr SCR % | 1.5 hr SCR % | 8 hr SCR % | 24 hr. SCR % |
|---|---|---|---|---|---|---|---|
| 64[1] | 35 | Caucasian | 0.15 | 80.0 | 80.0 | 75.6 | 71.8 |
| 64A[1] | PVP | Caucasian | 0.15 | 34.8 | 29.8 | 19.7 | 14.7 |
| 64B[1] | Luviset | Caucasian | 0.15 | 69.5 | 64.4 | 54.0 | 49.6 |

[1] Formulated with 0.3 wt. % Carbopol ® Ultrez 21 rheology modifier.

EXAMPLE 65

Hair gel formulations containing the polymers of the invention are formulated as set forth in Example 60 except that the amount of fixative polymer utilized ranges from 1 to 5 wt. % (polymer solids) as shown in Table 14 and that no rheology modifier is employed. Commercially available polymers known for hard hold fixative properties are also formulated. Asian type hair swatches are prepared, treated (0.8 g of fixative composition/swatch) and evaluated for mechanical stiffness after exposure to 50% and 90% relative humidity conditions as described above in the mechanical stiffness test method. Five replicates of each test sample are prepared and tested. The average peak force for the 5 replicates are calculated and recorded.

TABLE 14

| Ex. No. (Polymer Ex. No.) | Fixative (% TS) | Mechanical Stiffness (N) 50% RH | Mechanical Stiffness (N) 90% RH | Subjective Rating @ 50% RH | Subjective Rating @ 90% RH |
|---|---|---|---|---|---|
| 65A (44) | 4% | 11.4 | 10.1 | Super Hard Hold | n/a |
| 65B (45) | 4% | 8.1 | 6.9 | Super Hard Hold | n/a |
| 65C (42) | 4% | 9.7 | 9.8 | Super Hard Hold | n/a |
| 65D (35) | 4% | 8.3 | 8.3 | Super Hard Hold | n/a |
| 65E (41) | 4% | 7.7 | 7.5 | Super Hard Hold | n/a |
| 65F (8) | 4% | 7.1 | n/a | Super Hard Hold | n/a |
| 65G (39) | 4% | 6.9 | 7.2 | Hard Hold | Super Hard Hold |
| 65H (24) | 2% | 7.2 | 7.4 | Super Hard Hold | n/a |
| 65I (45) | 2% | 6.8 | 6.1 | Very Hard Hold | n/a |
| 65J (8) | 3% | 6 | n/a | Very Hard Hold | n/a |
| 65K (41) | 2% | 5.9 | 5.4 | Hard Hold | n/a |
| 65L (42) | 2% | 5.8 | 5.9 | Hard Hold | n/a |
| 65M (35) | 2% | 5.6 | 5.5 | Hard Hold | n/a |
| 65N (43) | 2% | 5.4 | n/a | Hard Hold | n/a |
| 65O (8) | 2% | 4.9 | n/a | Slightly Hard Hold | n/a |
| 65P (41) | 2% | 4.9 | 4.1 | Slightly Hard Hold | n/a |
| 65Q (8) | 1% | 3.7 | n/a | Soft Flexible Hold | n/a |
| Luviskol ® K90 | 5% | 7.8 | n/a | Super Hard Hold | n/a |
| Luviset ® Clear | 5% | 6.5 | n/a | Very Hard Hold | n/a |
| Fixate ® PLUS | 2% | 5.7 | n/a | Hard Hold | n/a |
| Kollidon ® K30 | 5% | 4.9 | n/a | Slightly Hard Hold | n/a |
| Luviskol ® K90 | 2% | 4.4 | n/a | Slightly Hard Hold | n/a |
| Luviset ® Clear | 2% | 4 | n/a | Slightly Hard Hold | n/a |
| Fixate ® G100 | 5% | 3.7 | n/a | Slightly Hard Hold | n/a |
| Acudyne ® SCP | 2% | 3.1 | n/a | Slightly crisp Hold | n/a |
| Kollidon ® K30 | 2% | 2.3 | n/a | Soft, flexible Hold | n/a |
| Fixate ® G100 | 2% | 2 | n/a | Soft, flexible | n/a |
| Luviskol ® VA73 | 2% | 1.2 | n/a | Soft, flexible | n/a |
| Asian hair swatch | Untreated Hair | 0.46 | n/a | Soft Flexible | n/a |

TABLE 14-continued

| Ex. No. (Polymer Ex. No.) | Fixative (% TS) | Mechanical Stiffness (N) 50% RH | Mechanical Stiffness (N) 90% RH | Subjective Rating @ 50% RH | Subjective Rating @ 90% RH |
|---|---|---|---|---|---|
| Caucasian (brown) hair swatch | Untreated Hair | 0.42 | n/a | Soft Flexible | n/a |

The data in Table 14 demonstrate that the fixative polymer embodiments of the invention exhibit mechanical stiffness values that range from 3 to 11.4 Newtons at 50% relative humidity (slightly soft hold to super hard hold styling performances). The commercial fixative polymers (e.g., Luviskol® and Luviset® Clear fixatives) exhibit mechanical stiffness values of 6.5 to 7.8 Newtons, equivalent to hard hold and super hard hold styling ratings, but higher concentrations (e.g. 5 wt. %) of polymer solids are needed to achieve these values. At lower polymer solids concentrations (e.g., 2 wt. %), these commercial polymers show reduced peak force values compared to the instant polymers.

EXAMPLE 66

Hair gel formulations containing the polymers of the invention are formulated as set forth in Example 60 with the amount of fixative polymer (wt. % polymer solids) set forth in Table 15. Commercially available polymers known for hard hold fixative properties are also formulated. Both the experimental and commercially available fixative polymers are formulated with 0.3 wt. % (based on the total wt. of the formulation components) Carbopol® Ultrez 21 rheology modifier. In addition comparative testing is also conducted utilizing commercial brand name hair fixative products. Asian type hair swatches are prepared, treated (0.8 g of fixative composition/swatch) and evaluated for mechanical stiffness after exposure to 50% and 90% relative humidity conditions as described above in the mechanical stiffness test method. Five replicates of each test sample are prepared and tested. The average peak force for the 5 replicates are calculated and recorded in the Table below.

TABLE 15

| Ex. No. (Polymer Ex. No.) | Fixative (% TS) | Mechanical Stiffness (N) 50% RH | Mechanical Stiffness (N) 90% RH | Subjective Rating @ 50% RH | Subjective Rating @ 90% RH |
|---|---|---|---|---|---|
| 66A (35) | 2.0 | 7.7 | 6.5 | Super Hard Hold | Very Hard Hold |
| 66B (41) | 2.0 | 6.7 | 5.8 | Very Hard Hold | Hard Hold |
| 66C (39) | 2.0 | 6.4 | 5.8 | Very Hard Hold | Hard Hold |
| 66D (8) | 2.0 | 5.8 | 5.4 | Hard Hold | Hard Hold |
| Luviskol ® K90 | 2.0 | 6.7 | 4.4 | Very Hard Hold | Slightly Hard Hold |
| Fixate ® PLUS | 2.0 | 6.2 | 6.1 | Very Hard Hold | Very Hard Hold |
| Luviset ® Clear | 2.0 | 5.7 | 4.7 | Hard Hold | Slightly Hard Hold |
| Acudyne ® SCP | 2.0 | 4.6 | 4.3 | Slightly Hard Hold | Slightly Hard Hold |
| Kollidon ® K30 | 2.0 | 3.9 | 1.7 | Soft to Slightly Hold | Soft, Flexible Hold |
| Fixate ® G100 | 2.0 | 3.7 | 4.6 | Soft to Slightly Hold | Slightly Hard Hold |
| Luviskol ® VA73 | 2.0 | 3.2 | 2 | Soft, flexible | Soft, flexible Hold |
| Shock Waves Xtrovert Styling Steel (Wella AG) | 15 | 9.15 | 8.3 | Super Hard Hold | Super Hard Hold |
| Studio Line Mega Glue (L'Oreal Group) | 7.1 | 7.3 | n/a | Super Hard Hold | n/a |
| Studio Line Mega Gel (L'Oreal Group) | 6.7 | 6.8 | n/a | Very Hard Hold | n/a |
| Fructis Style Hard Glue (Garnier, L'Oreal Group) | 9.5 | 6.1 | n/a | Very Hard Hold | n/a |

TABLE 15-continued

| Ex. No. (Polymer Ex. No.) | Fixative (% TS) | Mechanical Stiffness (N) 50% RH | Mechanical Stiffness (N) 90% RH | Subjective Rating @ 50% RH | Subjective Rating @ 90% RH |
|---|---|---|---|---|---|
| Suave Sculpting Freeze Gel (Unilever) | 6.8 | 5.6 | n/a | Hard Hold | n/a |
| Pantene Pro-V Total Control Shaping Gel (Procter & Gamble) | 5.8 | 5.4 | n/a | Hard Hold | n/a |
| Studio Line Melting Gel (L'Oreal Group) | 3.4 | 2.4 | n/a | Soft, Flexible Hold | n/a |
| Asian hair swatch | Untreated Hair | 0.46 | n/a | Soft Flexible | n/a |
| Caucasian (brown) hair swatch | Untreated Hair | 0.42 | n/a | Soft Flexible | n/a |

The mechanical stiffness values obtained for polymers of the invention (tested at 2 wt. % polymer solids with 0.3 wt. % Carbopol® Ultrez 21 rheology modifier, weights based on the weight of the total composition) ranges from 5.8 to 7.7 Newtons (average bending peak force). The experimental polymers exhibit hard hold to super hard hold styling performance at 50% relative humidity.

The mechanical stiffness values obtained for inventive polymers (tested at 2 wt. % polymer solids with 0.3 wt. % Carbopol® Ultrez 21 rheology modifier, weights based on the weight of the total composition) ranges from 5.4 to 6.5 Newtons (average bending peak force), giving long lasting, hard hold to very hard hold styling performance at 90% relative humidity with an excellent humidity resistance.

The rheology modifier improves the mechanical stiffness of all the fixative polymers as is illustrated when comparing the stiffness data in Table 14 (no rheology modifier) with the stiffness data in Table 15 (with rheology modifier).

Commercial fixative polymers afford mechanical stiffness at 50% relative humidity in the range 3.2 to 6.7 Newtons (average peak force), indicating hard hold to super hard hold style. However, mechanical stiffness values drop dramatically (except Fixate® PLUS, Fixate® G 100 polymers from Noveon and Acudyne™ SCP from Rohm and Haas) at 90% relative humidity, indicating poor humidity resistance properties.

Commercially marketed finished styling gel products from Procter & Gamble, L'Oreal, and Unilever also exhibit hard hold to super hard hold mechanical stiffness ratings (except Studio line melting gel from L'Oreal), but these commercial products are optimized and contain very high level of polymer solids including fixative polymers and other fixative ingredients of greater than 2.3 wt. % polymer solids.

The following examples illustrate the use of the instant polymers to formulate various hair care embodiments of the invention.

EXAMPLE 67

This example illustrates the use of the polymer synthesized in Examples 4, 10, 20, 28, 35, and 45 in a curl enhancing creme hair gel formulation shown in Table 16.

TABLE 16

| | Ingredient | Wt. % |
|---|---|---|
| | Part A | |
| 1 | D.I. water | q.s. to 100 |
| 2 | Carbopol ® Ultrez 21 rheology modifier | 0.70 |
| 3 | AMP-95 | 0.05 |
| 4 | Polymer Ex. 4, 10, 20, 28, 35, and 45 (fixative/rheology modifier) | 6.27 |
| 5 | AMP-95 (neutralizer) | 0.30 |
| | Part B | |
| 6 | D.I. water | 45.28 |
| 7 | Gafquat 755N (Conditioner) | 0.25 |
| | Part C | |
| 8 | Timiron ® pigment (pearlizing agent) | 0.20 |
| 9 | D.I. water | 5.0 |
| | Part D | |
| 10 | Sorbitol (70%) (humectant) | 0.60 |
| 11 | Glydant Plus (preservative) | 0.30 |
| | Part E | |
| 12 | Murumuru butter (shine enhancer) | 0.25 |
| 13 | AMP-95 (neutralizer) | 0.78 |

The rheology modifier is dispersed evenly in the D.I. water and pre-neutralized with AMP-95. The polymer of Examples 4, 10, 20, 28, 35, and 45 is slowly added to the pre-neutralized dispersion, mixed thoroughly and neutralized with additional AMP-95. The ingredients in Parts B, C, D and E are separately formulated and then added in alphabetical order to the Part A dispersion and mixed. The resulting gel formulation has an opaque gold appearance, a pH of greater than 6.3 and a viscosity of greater than 15,000 mPa·s.

EXAMPLE 68

This example illustrates the formulation of a high solids salon molding gel utilizing the polymer of Examples 4, 10, 20, 28, 35, and 45. The following ingredients are used to formulate the molding gel.

TABLE 17

| | Ingredient | Wt. % |
|---|---|---|
| 1 | D.I. Water | 66.39 |
| 2 | Polymer Ex. 4, 10, 20, 28, 35, and 45 (7.5 wt. % polymer solids) (fixative/rheology modifier) | 23.52 |
| 3 | Propylene Glycol (humectant) | 3.00 |
| 4 | Sorbitol (70%) (humectant) | 3.00 |
| 5 | Glycerin (humectant) | 0.50 |
| 6 | Panthenol (conditioner) | 0.50 |
| 7 | Tetrasodium EDTA (38% aqueous solution) (chelating agent) | 0.10 |
| 8 | Glydant Plus (preservative) | 0.30 |
| 9 | AMP-95 (neutralizer) | 2.69 |

Deionized water is weighed into a vessel and the experimental polymer is slowly added with mixing until an even dispersion is formed. Ingredients 3 to 8 are slowly added with mixing in the numerical order indicated in the Table. When a homogeneous dispersion is attained, the formulation is neutralized with ingredient 9 to a pH value of about 6.5.

The resulting gel formulation has a clear appearance (clarity value (% T) of greater than 90%), and a viscosity of greater than 10,000 mPa·s. The gel has excellent flow characteristics with a smooth, silky feel.

EXAMPLE 69

This example illustrates the formulation of a clear, low solids salon molding gel having low viscosity utilizing the polymer of Examples 4, 10, 20, 28, 35, and 45. The following ingredients are used to formulate the molding gel.

TABLE 18

| | Ingredient | Wt. % |
|---|---|---|
| 1 | D.I. Water | 84.48 |
| 2 | Carbopol ® Ultrez 21 rheology modifier | 0.5 |
| 3 | Polymer Ex. 4, 10, 20, 28, 35, and 45 (2.0 wt. % polymer solids) (fixative/rheology modifier) | 6.27 |
| 4 | Propylene Glycol (humectant) | 3.00 |
| 5 | Sorbitol (70%) (humectant) | 3.00 |
| 6 | Glycerin (humectant) | 0.50 |
| 7 | Panthenol (conditioner) | 0.50 |
| 8 | Tetrasodium EDTA (38% aqueous solution) (chelating agent) | 0.10 |
| 9 | Glydant Plus (preservative) | 0.30 |
| 10 | AMP-95 (neutralizer) | 1.35 |

Deionized water is weighed into a vessel and the rheology modifier is sprinkled into the vessel allowed to hydrate and then mixed to form a uniform dispersion. The inventive polymer is slowly added with mixing until an even dispersion is formed. Ingredients 3 to 9 are slowly added with mixing in the numerical order indicated in the Table. When a homogeneous dispersion is attained, the formulation is neutralized with ingredient 10 to a pH value of about 6.5.

The obtained gel formulation is subjectively compared to the high solids gel of Example 68 and is found to be just as clear but less viscous.

EXAMPLE 70

A "funky" (pigmented, easy to sculpt) hair gel is formulated with the polymer of Examples 4, 10, 20, 28, 35, and 45. This composition demonstrates the ability of the instant polymers to be formulated with ethanol, emollients and a texture modifier. The following ingredients are used to formulate the gel.

TABLE 19

| | Ingredient | Wt. % |
|---|---|---|
| | Part A | |
| 1 | D.I. water | q.s. to 100 |
| 2 | Carbopol ® Ultrez 21 rheology modifier | 0.30 |
| 3 | Polymer EX. 4, 10, 20, 28, 35, and 45 (5 wt. % total polymer solids) (fixative/rheology modifier) | 15.68 |
| | Part B | |
| 4 | Schercemol ™ DISF (emollient) | 1.0 |
| 5 | Ethanol | 3.0 |
| 6 | FD&C Blue No. 1 (color) | 0.10 |
| 7 | Glydant ® Plus (preservative) | 0.30 |
| 8 | AMP-95 (neutralizer) | 1.87 |
| | Part C | |
| 9 | PEG-90M (texture modifier) | 0.7 |
| 10 | Propylene Glycol (humectant) | 5.0 |
| 11 | D.I. water | 20.0 |

Deionized water is weighed into a suitable vessel and the rheology modifier is dispersed evenly in the D.I. water and then the polymer of Examples 4, 10, 20, 28, 35, and 45 is dispersed into the dispersion. The ingredients of Part B are added to the Part A dispersion in the order indicated in the Table concluding with the addition of ingredient 8. The ingredients of Part C are separately formulated and then added to the Part A dispersion with increased mixing. Additional AMP-95 is added (if necessary) to bring the final pH value to about 6.5. The resulting gel formulation has a blue appearance, a viscosity value of about 28,000 mPa·s and has a stretchy, stringy consistency.

EXAMPLE 71

The following high clarity hair gels demonstrate the ability of using the instant polymers with rheology modifiers to make smooth, low viscosity gels. The polymers of Examples 20, 35, and 45 are each formulated according to formulations A, B, and C as set forth in the table below (9 total formulations).

TABLE 20

| | Ingredient | A (wt %) | B (wt %) | C (wt %) |
|---|---|---|---|---|
| 1 | D.I. Water | 86.14 | 86.14 | 86.14 |
| 2 | Carbopol ® Ultrez 21 rheology modifier | 0.30 | | |
| | Carbopol ® 940 rheology modifier | | 0.30 | |
| | Carbopol ® 996 rheology modifier | | | 0.30 |
| 3 | Triethanolamine (99.5%) | 0.05 | 0.05 | 0.05 |
| 4 | Polymer Ex. 20, 35, and 45 (3 wt. % polymer solids) (fixative/rheology modifier) | 9.41 | 9.41 | 9.41 |
| 5 | Propylene Glycol (humectant) | 0.50 | 0.50 | 0.50 |
| 6 | Sorbitol (70%) (humectant) | 0.60 | 0.60 | 0.60 |
| 7 | Tetrasodium EDTA (38%) (chelating agent) | 0.10 | 0.10 | 0.10 |
| 8 | Glydant Plus (preservative) | 0.30 | 0.30 | 0.30 |
| 9 | Triethanolamine (99.5%) (neutralizer) | 2.60 | 2.60 | 2.60 |

Each formulation is prepared as follows. The rheology modifier is dispersed in D.I. water and mixed until a uniform dispersion is obtained. The aqueous dispersion is then partially neutralized with triethanolamine. Ingredient numbers 4 through 8 are then slowly added in numerical order with agitation until a homogenous dispersion is formed. The pH of the dispersion is adjusted to about 6.5 with additional triethanolamine to give smooth, low viscosity gels. All formulations are clear (>90% T) with a viscosity of <20,000 mPa·s.

EXAMPLE 72

Hair gels are formulated from the polymers of Examples 20, 35, and 45. Each polymer is formulated according to formulations A, B, and C as set forth in the table below (9 total formulations) demonstrating that clear, medium viscosity gels can be obtained. The formulation procedure of Example 71 is repeated for the medium viscosity gels.

TABLE 21

| | Ingredient | A (wt %) | B (wt %) | C (wt %) |
|---|---|---|---|---|
| 1 | D.I. Water | 85.74 | 85.74 | 85.74 |
| 2 | Carbopol ® Ultrez 21 rheology modifier | 0.70 | | |
| | Carbopol ® 940 rheology modifier | | 0.70 | |
| | Carbopol ® 996 rheology modifier | | | 0.70 |
| 3 | Triethanolamine (99.5%) | 0.05 | 0.05 | 0.05 |
| 4 | Polymer Ex. 20, 35, and 45 (3 wt. % total polymer solids) (fixative/rheology modifier) | 9.41 | 9.41 | 9.41 |
| 5 | Propylene Glycol (humectant) | 0.50 | 0.50 | 0.50 |
| 6 | Sorbitol (70%) (humectant) | 0.60 | 0.60 | 0.60 |
| 7 | Tetrasodium EDTA (38%) (chelating agent) | 0.10 | 0.10 | 0.10 |
| 8 | Glydant Plus (preservative) | 0.30 | 0.30 | 0.30 |
| 9 | Triethanolamine (99.5%) (neutralizer) | 2.60 | 2.60 | 2.60 |

All formulations are clear (>90% T) with a viscosity of <45,000 mPa·s.

EXAMPLE 73

Hair gels are formulated from the polymers of Examples 20, 35, and 45. Each polymer is formulated according to formulations A, B, and C set forth in the table below (9 total formulations) demonstrating that clear, high viscosity gels can be prepared by increasing the wt. % of the polymer solids. The formulation procedure of Example 71 is repeated for the high viscosity gel compositions.

TABLE 22

| | Ingredient | A (wt %) | B (wt %) | C (wt %) |
|---|---|---|---|---|
| 1 | D.I. Water | 79.58 | 79.48 | 79.48 |
| 2 | Carbopol ® Ultrez 21 rheology modifier | 0.60 | | |
| | Carbopol ® 940 rheology modifier | | 0.70 | |
| | Carbopol ® 996 rheology modifier | | | 0.70 |
| 3 | Triethanolamine (99.5%) (neutralizer) | 0.05 | 0.05 | 0.05 |
| 4 | Polymer Ex. 20, 35, and 45 (5 wt. % polymer solids) (fixative/rheology modifier) | 15.67 | 15.67 | 15.67 |
| 5 | Propylene Glycol (humectant) | 0.50 | 0.50 | 0.50 |
| 6 | Sorbitol (70%) (humectant) | 0.60 | 0.60 | 0.60 |
| 7 | Tetrasodium EDTA (38%) (chelating agent) | 0.10 | 0.10 | 0.10 |
| 8 | Glydant Plus (preservative) | 0.30 | 0.30 | 0.30 |
| 9 | Triethanolamine (99.5%) (neutralizer) | 2.60 | 2.60 | 2.60 |

All formulations are clear (>90% T) with a viscosity of >45,000 mPa·s.

EXAMPLE 74

Hair gels are formulated from the polymers of Examples 20, 35, and 45. Each polymer is formulated according to formulations A, B, and C set forth in the table below (9 total formulations).

TABLE 23

| | Ingredient | A (wt %) | B (wt %) | C (wt %) |
|---|---|---|---|---|
| 1 | D.I. Water | 91.98 | 91.98 | 91.98 |
| 2 | Carbopol ® Ultrez 21 rheology modifier | 0.50 | | |
| | Carbopol ® 940 rheology modifier | | 0.50 | |
| | Carbopol ® 996 rheology modifier | | | 0.50 |
| 3 | AMP-95 (neutralizer) | 0.05 | 0.05 | 0.05 |
| 4 | Polymer Ex. 20, 35, and 45 (2 wt. % polymer solids) (fixative/rheology modifier) | 6.27 | 6.27 | 6.27 |
| 5 | Propylene Glycol (humectant) | 0.10 | 0.10 | 0.10 |
| 6 | Sorbitol (70%) (humectant) | 0.40 | 0.40 | 0.40 |
| 7 | Panthenol (conditioner) | 0.10 | 0.10 | 0.10 |
| 8 | SilSense ™ Copolyol-1 (conditioner) | 0.20 | 0.20 | 0.20 |
| 9 | Tetrasodium EDTA (38%) (chelating agent) | 0.10 | 0.10 | 0.10 |
| 10 | Glydant ® Plus (preservative) | 0.30 | 0.30 | 0.30 |
| 11 | AMP-95 (neutralizer) | q.s. | q.s. | q.s. |

Each formulation is prepared as follows. The rheology modifier is dispersed in water and mixed until a uniform dispersion is obtained. The aqueous dispersion is then partially neutralized with AMP-95. Ingredient numbers 4 through 10 are then slowly added in numerical order with agitation until a homogenous dispersion is formed. The pH of the dispersion is adjusted to about 6.5 with additional AMP-95 to give smooth, low viscosity gels.

EXAMPLE 75

This formulation demonstrates the ability to create a wax formulation using the polymer of Examples 4, 10, 20, 28, 35, and 45 with oil and a mixture of surfactants and emulsifiers. Each polymer is formulated with the ingredients set forth in the table below.

TABLE 24

| | Ingredient | Wt. % |
|---|---|---|
| | Part A | |
| 1 | D.I. Water | q.s to 100 |
| 2 | Propylene Glycol (humectant) | 5.00 |
| 3 | Sorbitol (70%) (humectant) | 7.00 |
| 4 | Methyl Paraben (preservative) | 0.15 |
| 5 | Butyl Paraben (preservative) | 0.10 |
| | Part B | |
| 6 | Drakeol ® 7 LT Mineral Oil (emollient) | 11.00 |
| 7 | Arlasolve ™ 200 (surfactant/emulsifier) | 20.00 |
| 8 | Chemonic ™ OE-2 (emulsifier) | 6.00 |
| 9 | Propyl Paraben (preservative) | 0.15 |
| | Part C | |
| 10 | Polymer Ex. 4, 10, 20, 28, 35, and 45 (3 wt. % polymer solids) (fixative/rheology modifier) | 9.41 |
| | Part D | |
| 11 | AMP-95 (neutralizer) | q.s. to pH 6.5 |

The Part A ingredients are combined with mixing and heated to 70° C. In a separate vessel the Part B ingredients are combined with mixing and also heated to 70° C. Part B is combined with Part A, mixed and heated to 70° C. for 5 minutes. The pH of each formulation is adjusted to approximately 6.5 and a semi-solid waxy gel is obtained.

EXAMPLE 76

This example demonstrates the formulation of a curl enhancing creme gel utilizing the polymer of Examples 4, 10, 20, 28, 35, and 45 and a guerbet ester as a shine/sheen enhancing adjuvant. Each polymer is formulated with the ingredients set forth in the table below.

TABLE 25

| | Ingredient | Wt % |
|---|---|---|
| 1 | D.I. Water | q.s. to 100 |
| 2 | Carbopol ® Ultrez 21 rheology modifier | 0.6 |
| 3 | Polymer Ex. 4, 10, 20, 28, 35, and 45 (2.0 wt. % total polymer solids) (fixative/rheology modifier) | 6.27 |
| 4 | Sorbitol (70%) (humectant) | 0.60 |
| 5 | Ultracas ® G-20 guerbet ester (emollient/shine enhancer) | 3.00 |
| 6 | Glydant ® Plus (preservative) | 0.30 |
| 7 | AMP-95 (neutralizer) | 1.08 |

The rheology modifier is uniformly dispersed in D.I. water. Ingredients 3 through 6 are added in numerical order and mixed until a uniform dispersion is obtained. The dispersion is neutralized to a pH of approximately 6.3 where a creamy white gel is obtained. The gels have a viscosity of about 33,000 mPa·s and are shinny in appearance.

EXAMPLE 77

Two hairspray compositions utilizing the polymer of Example IV are prepared in aqueous and hydro-alcoholic (propellant compatible) formulations using the ingredients set forth in the table below.

TABLE 26

| Ingredients and Properties | A. Aqueous Hair Spray (wt. %) | B. Hydro-Alcoholic Hair Spray (wt. %) |
|---|---|---|
| D.I. Water | q.s. to 100 | q.s. to 100 |
| Polymer of Ex. IV | 5 | 5 |
| Ethanol | 0 | 55 |
| Glydant ® Plus (preservative) | 0.2 | 0 |
| pH | 8.6 | 7 |
| Viscosity (mPa·s) | 13.5 | 18.5 |
| Clarity (% T) | 46.0 | 87.0 |
| Turbidity (NTU) | 61.5 | 7.22 |

The hair spray compositions are prepared as follows utilizing conventional mixing techniques.

Formulation A: A 400 g batch of 5% active polymer solution is dispersed in D.I. water with 0.2% preservative and measured for viscosity, clarity and turbidity properties.

Formulation B: A 200 g sample 5% active polymer is dispersed in ethanol and measured for viscosity, clarity and turbidity properties.

Both the aqueous and the solvent based hair spray formulations have sufficiently low viscosity values to be sprayable. Each of the formulations provides good styling properties with excellent hold.

EXAMPLE 78

This example exemplifies the use of the instant polymers to formulate a hair styling mousse. Each of the polymers of Examples VI, 35, and 45 are formulated with the ingredients set forth in the table below to formulate hair styling mousse compositions.

TABLE 27

| | Ingredients | Wt. % |
|---|---|---|
| | Part A | |
| 1 | Lauramide DEA (foam booster) | 0.5 |
| 2 | Sodium methyl oleyl taurate (surfactant) | 1.5 |
| 3 | Behenyl alcohol (emollient/solvent) | 0.10 |
| 4 | Fragrance | 0.10 |
| | Part B | |
| 5 | D.I. Water | q.s. to 100 |
| 6 | Polymer Ex. IV, 35, and 45 | 3-5 |
| 7 | Glydant ® Plus (preservative) | 0.78 |
| 8 | Disodium EDTA (chelating agent) | 0.20 |
| 9 | AMP-95 (neutralizer) | q.s. to pH 6 |
| | Part C | |
| 10 | Propane/butane (propellant) | 10.0 |

The polymers are formulated as follows. Mix Part A with stirring and combine with the components of Part B in the listed order before neutralizing to pH 6. The AB composition is charged in to a suitable pressurizable container (polymer lined aluminum can) which is sealed with a mousse valve positioned on the top of the can. A vacuum is placed on the can to evacuate the headspace. The valve is then crimped into place and the can is charged with the propellant mixture (ingredient No. 10) through the valve stem.

In another embodiment of the invention, the polymers containing repeating units polymerized from the dimethicone copolyol macromers can be used in rinse-off hair treatment compositions (shampoo, conditioning shampoo, 2-in-1 shampoo, color maintenance shampoo, after color shampoo, and the like). These shampoos impart styling and "body" benefits to the hair without compromising the cleansing and/or conditioning attributes of the shampoo. "Body" benefits include root lift, increased hair volume, bounce, control (i.e. ease of styling) and manageability, i.e. maintenance of style without negative sensory feel. Such body attributes are particularly attractive to people with fine or long, weighty hair.

Formulations for surfactant cleansing applications such as, for example, shampoos (e.g., 2-in-1 shampoos, dandruff shampoos), bath gels, body washes, and the like) incorporating the polymers of the present invention can comprise an anionic surfactant, nonionic, a zwitterionic surfactant, an amphotheric surfactant or mixtures of; mono and polymeric quats for conditioning; silicones for conditioning; rheology modifiers; thickeners; suspending agents; preservatives; fragrance/fragrance solubilizer; colorants; pigments, neutralizers or pH adjusters; botanicals; vitamins; chelating agents; foam boosters; beads; air bubbles; mica; organic and inorganic pearlizing agents; water; viscosity reducers; hydrotropes; alcohols; anti-dandruff actives; salt and combinations thereof.

EXAMPLE 79

Separate clear bath gel compositions with suspended beads are formulated with the polymers of Examples 13, 20a, 20b, and 20c. The ingredients and amounts are set forth in the table below.

TABLE 28

| Ingredient | Wt. % |
|---|---|
| Part A | |
| D.I. Water | q.s. |
| Polymers (30 wt. % total solids) | 8.30 |

TABLE 28-continued

| Ingredient | Wt. % |
|---|---|
| Example 79A polymer of Ex. 13 | |
| Example 79B polymer of Ex. 20a | |
| Example 79C polymer of Ex. 20b | |
| Example 79D polymer of Ex. 20c | |
| Sodium Laureth Sulfate (2 mole ethoxylate; 28% aqueous solution) (surfactant) | 40.0 |
| Sodium hydroxide (18% aqueous solution) (neutralizer) | 1.32 |
| Part B | |
| Cocamidopropylbetaine (30% aqueous solution) (secondary surfactant) | 2.10 |
| Polyquaternium-39 (conditioner) | 2.10 |
| Tetrasodium EDTA (chelating agent) | 0.05 |
| Polysorbate 20 (surfactant/solubilizer) | 0.50 |
| Phenonip ® (preservative) | 0.50 |
| Fragrance | 0.50 |
| FD&C Blue #1 (dye) | 1.85 |
| FD&C Yellow #6 (dye) | 0.85 |
| Lipopearls ™ vitamin E beads | 1.00 |

Each bath gel composition is formulated by dispersing the respective experimental polymer in D.I. water. To the dispersed polymer is added the sodium laureth sulfate surfactant with gentle mixing. The Part A component is neutralized with NaOH to pH 6.5. The Part B ingredients are added to the Part A mixture in numerical order with mixing. The pH of the final composition is adjusted to 6.5 if necessary. Each of the bath gel compositions are evaluated for viscosity, yield and turbidity properties, as well as for suspension stability. From the bath gel properties set forth in the table below, the gels exhibit good clarity, rheology and suspension stability properties (i.e., the ability to suspend solid particulates for long periods of time).

TABLE 29

| | Example 79A | Example 79B | Example 79C | Example 79D |
|---|---|---|---|---|
| Appearance | Viscous clear liquid | Viscous clear liquid | Viscous clear liquid | Viscous clear liquid |
| pH | 6.4 | 6.4 | 6.4 | 6.4 |
| Viscosity | 2,080 | 3,300 | 5,700 | 3,290 |
| Yield Value (dynes/cm2) | 54 | 132 | 314 | 104 |
| Turbidity (NTU) | 8.78 | 9.65 | 167 | 28.2 |
| Suspension @ 45° C. | 12 wks. | 12 wks. | 12 wks. | 12 wks. |

EXAMPLE 80

The following formulation is an example of a temporary color shampoo or color maintenance shampoo using the polymer of Examples 13, 20a, 20b, and 20c. The shampoo demonstrates a stable viscous temporary hair color composition using cationic dyes; excellent suspension and stabilization of a pearlescent material with enhanced pearlescent appearance; improved rheological and sensory properties.

TABLE 30

| | Ingredient | Wt. % |
|---|---|---|
| | PART A | |
| 1 | D.I. Water | q.s. to 100 |
| 2 | Polymer Ex. 13, 20a, 20b, and 20c. (30 wt. % polymer solids) | 10.00 |
| | PART B | |
| 3 | D.I. Water | 15.00 |
| 4 | Disodium EDTA (chelating agent) | 0.05 |
| 5 | Butylene Glycol (solubilizer) | 5.00 |
| 6 | Sodium cocoamphoacetate (37% aqueous solution) (surfactant) | 15.00 |
| 7 | Cocamidopropylbetaine (35% aqueous solution) (secondary surfactant) | 3.00 |
| 8 | Polyquaternium-39 (conditioner) | 0.80 |
| 9 | Germaben ® II (biocide) | 0.45 |
| | PART C | |
| 10 | Deionized water | 10.00 |
| 11 | Arianor ® Sienna Brown (dye) | 0.25 |
| 12 | Arianor ® Steel Blue (dye) | 0.125 |
| 13 | Arianor ® Madder Red (dye) | 0.125 |
| 14 | DC 193 dimethicone copolyol (conditioner) | 0.20 |
| | PART D | |
| 15 | Plantaren ® 2000 (surfactant) | 4.00 |
| 16 | D.I. Water | 3.00 |
| 17 | Timiron ® Diamond Cluster MP-149 (mica/TiO₂) (Pearlizing agent) | 0.20 |

The Part A ingredients are combined and mixed thoroughly. In a separate vessel the Part B ingredients are formulated by dissolving disodium EDTA in warm D.I. water (approximately 50° C.). The remaining Part B ingredients (5 through 9) are added in numerical order with gentle mixing. Part B is slowly added to Part A with moderate mixing. The pH of the combined composition is adjusted to 7.0. The Part C ingredients are combined in a separate vessel by first dissolving the dyes (ingredients 11 through 13) in warm D.I. water (approximately 50° C.). The dimethicone copolyol is then added to the dye solution. Part C is combined with Part AB with gentle agitation. Part D ingredient No. 17 is pre-dispersed in D.I. water and is combined along with ingredient No. 15 in the Part ABC composition and mixed.

EXAMPLE 81

This example illustrates the formulation of a conditioning anti-dandruff shampoo utilizing a polymer embodiment of the invention. The composition is formulated by the "back-acid" technique herein described.

TABLE 31

| | Ingredient | Wt. % |
|---|---|---|
| | PART A | |
| 1 | D.I, Water | q.s. to 100 |
| 2 | Polymer Ex. 13, 20a, 20b, and 20c | 5.00 |
| 3 | Sodium Lauryl Sulfate (29% aqueous solution) (surfactant) | 16.00 |
| 4 | Sodium Laureth Sulfate (2 mole ethoxylate; 28% aqueous solution) (surfactant) | 16.00 |
| 5 | Sodium hydroxide (18% aqueous solution) (neutralizer) | 0.65 |
| | PART B | |
| 6 | D.I. Water | 10.00 |
| 7 | Polyquaternium-10 (conditioner) | 0.25 |
| 8 | Glydant ® Plus (preservative) | 0.30 |

TABLE 31-continued

| Ingredient | Wt. % |
|---|---|
| PART C | |
| 9 Cocamidopropylbetaine (35% aqueous solution) (secondary surfactant) | 4.00 |
| 10 Citric Acid (50%) (back-acid) | 0.75 |
| 11 Zinc Omadine ® (48% aqueous dispersion) (anti-dandruff agent) | 2.50 |
| 12 DC 1784 Emulsion (conditioner) | 3.00 |
| 13 FD&C Blue #1 (0.1%) (dye) | 1.00 |
| 14 Fragrance | 0.50 |
| 15 Sodium Chloride | 0.60 |

The ingredients of Part A are combined by dispersing the polymer of Examples 13, 20a, 20b, and 20c in D.I. water. The surfactants, ingredient Nos. 3 and 4 are added to the dispersion with gentle agitation to minimize air bubble entrapment. Part A is then neutralized with ingredient No. 5 to a pH of 6.5. The Part B ingredients are combined in a separate vessel and warmed to 45° C. to assist in the dissolution of the conditioner, ingredient No. 7. Part B is added to Part A and mixed. The Part C surfactant, ingredient No. 9, is added to Part AB and ingredient No. 10 is utilized to back-acid adjust the pH to 5.5. The remaining Part C ingredients, Nos. 11 through 14, are added in numerical order to the thickened Part ABC composition. Sodium chloride, ingredient No. 15 is added to adjust the viscosity of the formulation. The obtained anti-dandruff conditioning shampoo is stable and is able to suspend the insoluble anti-dandruff agent, zinc pyrithione, without any settling.

EXAMPLE 82

The polymers of the present invention containing surface active silicone moieties can be used in a variety of cosmetic hair formulations (leave-on and rinse-off), such as hair treatments, hair lotions, hair tonics, hair rinses, hair emulsions, treatment fluids for damaged ends, equalizers for permanent waves, hot-oil treatment preparations, conditioners, and the like. The following example illustrates the use of polymer embodiments of the invention in the formulation of a cationic compatible creamy conditioner with monomeric quaternium compounds, fatty alcohol emulsifiers and emollients. The composition ingredients are set forth in the table below.

TABLE 32

| Ingredient | Wt. % |
|---|---|
| Part A | |
| 1 D.I. Water | q.s. |
| 2 Cationic Emulsion Polymer(20 wt. % polymer solids) (see below) | 1.50 |
| 3 Propylene Glycol (humectant) | 2.50 |
| 4 Cetrimonium Chloride (29% solution) (conditioner/antistatic agent) | 3.45 |
| Part B | |
| 5 Cetyl Alcohol (emulsifier/opacifier) | 1.10 |
| 6 Stearyl Alcohol (emulsifier/opacifier) | 0.63 |
| 7 Wecobee ® (emollient) | 0.60 |
| 8 Neobee ® M-5 (emollient) | 1.68 |
| Part C | |
| 9 Glydant ® Plus (preservative) | 0.20 |
| 10 Citric Acid (10%) | 0.50 (q.s. to pH 4.0) |

Deionized water (ingredient No. 1) is heated to 65 to 67° C. The remaining Part A ingredients (Nos. 2 to 4) are added to the warm water and mixed thoroughly. In a separate vessel the Part B ingredients are combined under mixing and heated to 65 to 67° C. Part B is combined with Part A and mixed until a uniform dispersion is obtained. The Part AB dispersion is cooled to 40° C. Ingredient No. 9 is added and mixing is continued. The pH is adjusted with ingredient No. 10 to 4.0. The viscosity and appearance properties of the compositions are set forth in the table below.

TABLE 33

| | Ex. No. | | | |
|---|---|---|---|---|
| | 82A | 82B | 82C | 82D |
| Polymer of Ex. | 56 | 58 | 57 | 59 |
| Viscosity, mPa · s | 5,700 | 14,050 | 5,860 | 16,350 |
| Appearance | Smooth, Creamy | Smooth, Creamy | Smooth, Creamy | Smooth, Creamy |

EXAMPLE 83

This example illustrates the formulation of a conditioning anti-dandruff shampoo utilizing the cationic polymer embodiments and ingredients set forth in the table below. Each polymer is formulated separately.

TABLE 34

| Ingredient | Wt. % |
|---|---|
| PART A | |
| 1 D.I. Water | 49.39 |
| 2 Polyquaternium-10 (conditioner) | 0.25 |
| PART B | |
| 3 Sodium Lauryl Sulfate (30% aqueous solution) (surfactant) | 16.00 |
| 4 Sodium Laureth Sulfate (2 mole ethoxylate; 28% aqueous solution) (surfactant) | 16.00 |
| PART C | |
| 5 Polymer of Examples 56 to 59 | 6.96 |
| 6 Cocamidopropylbetaine (35% aqueous solution) (secondary surfactant) | 4.00 |
| 7 Zinc Omadine ® (48% aqueous dispersion) (anti-dandruff agent) | 2.50 |
| 8 DC 1664 Emulsion (conditioner) | 3.00 |
| 9 FD&C Blue No. 1 (0.1%) (colorant) | 0.50 |
| 10 Fragrance (XBF-800404-Lavender Breeze) | 0.30 |
| 11 Glydant ® Plus (antimicrobial) | 0.30 |
| 12 Herbasol ® Stinging Nettle Extract in propylene glycol (botanical extract) | 0.10 |
| 13 Herbasol ® Horsetail Extract in propylene glycol (botanical extract) | 0.10 |
| 14 Herbasol ® Chamomile Extract in propylene glycol (botanical extract) | 0.10 |
| 15 Citric Acid (50%) (neutralizer) | 0.50 |

Parts A and B are formulated in separate vessels with agitation to obtain uniform mixtures. Part A is slowly combined with Part B with mixing. The Part C ingredients (5 through 14) are mixed into the Part AB composition in numerical order and mixed until a uniform mixture is obtained. The pH of the ABC composition is adjusted with ingredient 15 to a pH value of between 4.9 and 5.3 inclusive. Stable shampoo compositions are obtained.

EXAMPLE 84

The following formulation is an example of a conditioning facial wash. It demonstrates a stable, aqueous surfactant composition in low pH formulation using salicylic acid. Each polymer is formulated with the ingredients listed in the table below

TABLE 35

| | Ingredient | Wt. % |
|---|---|---|
| | Part A | |
| 1 | D.I Water | 30.74 |
| 2 | Polymer of Examples 56 to 59 | 6.96 |
| 3 | Bio-Terge ® AS-40 (surfactant) | 17.50 |
| 4 | Citric Acid (50%) | 1.00 |
| | Part B | |
| 5 | D.I. Water | 10.00 |
| 6 | Bio-Terge ® AS-40 (surfactant) | 17.50 |
| 7 | Salicylic Acid (exfoliant) | 2.00 |
| | Part C | |
| 8 | Cocamidopropyl Betaine (35%) (secondary surfactant) | 10.00 |
| 9 | Glycerin (humectant) | 1.00 |
| 10 | Hydramol ™ PGPL Ester (moisturizer/conditioner) | 1.00 |
| 11 | Tocopheryl Acetate (anti-oxidant/moisturizer) | 0.10 |
| 12 | Herbasol ® Tea Tree Extract in propylene glycol (botanical extract) | 0.10 |
| 13 | Herbasol ® Witch Hazel Extract in propylene glycol (botanical extract) | 0.10 |
| 14 | FD&C Green No. 3 (0.1%) (colorant) | 0.50 |
| 15 | Unispheres ® YE-501 (Cosmetic Beads) | 1.00 |
| 16 | Citric Acid (50%) | 0.50 |

In a mixing vessel the Part A ingredients (1 to 3) are combined in the order listed in the table and uniformly mixed. The mixture is pre-neutralized with citric acid. The Part B ingredients are mixed in a separate vessel and combined with Part A. The Part C ingredients (8 to 15) are added to the Part AB mixture in the order listed and mixed until a uniform composition is obtained. The pH of the Part ABC formulation is adjusted with ingredient 15 to 4.0. A stable facial wash is obtained.

EXAMPLE 85

This example demonstrates the preparation of a clear conditioning shampoo containing a mixture of silicones, cationic materials and botanicals in a low pH formulation. The ingredients and formulation procedure are set forth below.

TABLE 36

| | Ingredients | Wt. % |
|---|---|---|
| | Part A | |
| 1 | D.I. Water | 43.49 |
| 2 | Polyquaternium-10 (conditioner) | 0.25 |
| 3 | Tetrasodium EDTA (chelating agent) | 0.05 |
| 4 | Sodium Benzoate (preservative) | 0.50 |
| 5 | Kathon ® CG (preservative) | 0.05 |
| | Part B | |
| 6 | Ammonium Lauryl Sulfate (30%) (surfactant) | 30.00 |
| | Part C | |
| 7 | Polymer of Examples 56 to 59 | 6.96 |
| 8 | Sodium Laureth Sulfate (2 mole ethoxylate; 28% aqueous solution) (surfactant) | 10.00 |
| 9 | Cocamide MEA (100%) (surfactant booster) | 1.00 |
| 10 | Cocamidopropyl Betaine (35%) (secondary surfactant) | 5.00 |
| 11 | Silsense ™ Q-Plus Silicone (conditioner) | 0.30 |
| 12 | SilSense ™ A-23 Silicone (conditioner) | 0.50 |
| 13 | Herbasol ™ *Aloe Vera* Extract in propylene glycol (botanical extract) | 0.10 |
| 14 | Tocopheryl Acetate (anti-oxidant/moisturizer) | 0.10 |
| 15 | *Chamomilla Recutita* (Matricaria) Flower Extract, Propylene Glycol | 0.10 |
| 16 | Fragrance (Blossoming Cucumber #UJ003904/00) | 0.30 |
| 17 | FD&C Green No. 3 (0.1%) (dye) | 0.5 |
| 18 | FD&C Yellow No. 5 (0.1%) (dye) | 0.5 |
| 19 | Citric Acid (50%) (pH adjuster) | 0.3 |

Part A is formulated by adding ingredient No. 2 to D.I. water and mixing until a uniform dispersion is obtained. Ingredients Nos. 3 to 5 are added to the dispersion and mixed. Part A is slowly combined with Part B and mixed. Part C ingredients, Nos. 7 through 18 are added in the order listed and mixed until a uniform mixture is obtained. The pH is adjusted with ingredient No. 19 to 5.0. A stable, homogeneous shampoo is obtained.

EXAMPLE 86

This example illustrates the formulation of a body lotion composition utilizing the polymer of Examples 13, 20a, 20b, 20c, and 20d. The composition components are set forth in the table below.

TABLE 37

| | Ingredient | Wt. % |
|---|---|---|
| | Part A | |
| 1 | D.I. Water | 76.80 |
| 2 | Glycerin (humectant) | 2.50 |
| 3 | Mineral Oil (emollient) | 4.00 |
| 4 | $C_{12}$-$C_{15}$ Alkyl Benzoate (emollient) | 2.50 |
| 5 | Cetiol ® 868(emollient) | 1.75 |
| 6 | Cetyl Alcohol (coemulsifier/opacifier) | 1.50 |
| 7 | Emulgade ® 1000 NI (emulsifier/moisture barrier) | 3.00 |
| | Part B | |
| 8 | Polymer Ex. 13, 20a, 20b, 20c and 20d (30% polymer solids) (rheology modifier/sensory enhancer) | 5.00 |
| 9 | Sodium hydroxide (18%) (neutralizer) | 0.95 |
| 10 | DC 1401 Fluid Cyclomethicone (and) Dimethicone (Lubricant) | 1.00 |
| 11 | Germaben ® II-E (preservative) | 1.00 |

The Part A ingredients are placed in a vessel in the number order indicated and heated to 65 to 70° C. under medium agitation for 20 minutes. The mixture is cooled to 60° C. and the polymer of Examples 13, 20a, 20b, 20c, and 20d is added to the formulation. The pH is adjusted to about 6.8 with ingredient No. 9 and the formulation is cooled to 50° C. Ingredient No. 10 is then added with mixing and the formulation is cooled to 40° C. Ingredient No. 11 is added and mixed until a homogeneous composition is obtained.

EXAMPLE 87

This example illustrates the use of the cationic polymer of Examples 56 to 59 in formulating a conditioning hair gel. The ingredients and method of preparation are set forth below.

TABLE 38

| | Ingredient | Wt % |
|---|---|---|
| 1 | D.I. Water | q.s. |
| 2 | Polyquaternium-4 (conditioner/hair fixative) | 1.00 |
| 3 | Tetrasodium EDTA Liquid (38%) (chelating agent) | 0.10 |
| 4 | Cationic Emulsion Polymer Ex. 56-59 (20 wt. % polymer solids) | 9.28 |

TABLE 38-continued

| | Ingredient | Wt % |
|---|---|---|
| | (rheology modifier/sensory enhancer/conditioner) | |
| 5 | SilSense ™ Copolyol-1 (conditioner) | 0.10 |
| 6 | Glydant Plus ® (preservative) | 0.30 |
| 7 | Glycolic Acid (50% solution) (neutralizer) | 0.50 |

Ingredient No. 1 is dispersed with mixing into D.I. water until a uniform mixture is obtained. Ingredient Nos. 2 through 6 are added in numerical order until and mixed. The pH of the mixture is adjusted to about 4.0 and the formulation is mixed until a homogeneous gel is formed. The gel properties are set forth in the table below.

TABLE 39

| | Ex. No. | | | |
|---|---|---|---|---|
| | 87A | 87B | 87C | 87D |
| Polymer of Example | 58 | 59 | 56 | 57 |
| pH | 3.98 | 4.04 | 3.94 | 3.96 |
| Viscosity (mPa · s @ 24 hours) | 22,800 | 22,950 | 17,100 | 17,100 |
| Turbidity (% T) | 4.91 | 4.20 | 8.21 | 8.50 |

The fixative compositions are evaluated for high humidity curl retention on hair tresses (9 repetitions/composition) via the (HHCR) test described above. The results are illustrated in the table below.

TABLE 40

| Polymer Ex. No. | Hair | Gel/g hair tress | 0.75 Hr HHCR % | 1.5 Hr HHCR % | 8 Hr HHCR % | 24 Hr HHCR % |
|---|---|---|---|---|---|---|
| 56 | Caucasian Brown | 0.32 | 99.0 | 97.1 | 92.7 | 91.2 |
| 58 | Caucasian Brown | 0.32 | 100.0 | 96.1 | 90.5 | 86.6 |
| 57 | Caucasian Brown | 0.32 | 99.0 | 98.0 | 82.8 | 81.3 |
| 59 | Caucasian Brown | 0.32 | 96.7 | 95.7 | 73.8 | 72.4 |

EXAMPLE 88

A clear bath gel is formulated with the ingredients set forth in the table below and utilizing the back-alkaline formulation procedure.

TABLE 41

| | Ingredient | Wt. % |
|---|---|---|
| 1 | D.I. Water | q.s. |
| 2 | Tetrasodium EDTA (chelating agent) | 0.05 |
| 3 | Phenonip ® preservative | 0.05 |
| 4 | Cationic Emulsion Polymer Ex. 56-59 (20 wt. % polymer solids) (rheology modifier/conditioner) | 7.50 |
| 5 | Sodium Laureth Sulfate (2 mole ethoxylate; 28% aqueous solution) (surfactant) | 40.00 |
| 6 | Cocamidopropyl Betaine (35%) (secondary surfactant) | 16.67 |
| 7 | Citric Acid (50%) to pH (neutralizer) | q.s. |
| 8 | Sodium Hydroxide (18%) to pH (pH adjusting agent) | q.s. |

Each of the polymers of Examples 56 to 59 is dispersed in deionized water (ingredient No. 1) and mixed until a homogeneous dispersion is obtained. Ingredient Nos. 2 and 3 are then added with mixing. Ingredient No. 6 is added to the dispersion and mixed. The pH of each formulation is adjusted to pH 6.0 with citric acid (ingredient No. 7) to increase the viscosity of the composition. A sample of each composition is tested for viscosity properties and recorded. The pH of each composition is back-alkaline adjusted with sodium hydroxide (ingredient No. 8) and the viscosity properties are again recorded as set forth in the table below.

TABLE 42

| | Ex. No. | | | |
|---|---|---|---|---|
| | 88A | 88B | 88C | 88D |
| Polymer of Ex. | 58 | 59 | 56 | 57 |
| 24 Hour Readings | | | | |
| Viscosity (mPa · s) | | | | |
| pH 6.0 | 7,040 | 6,660 | 5,320 | 4,320 |
| pH 4.0 | 9,960 | 9,500 | 8,280 | 6,380 |
| pH 6.0* | 8,600 | 8,040 | 7,120 | 5,500 |
| Turbidity (NTU) | | | | |
| pH 6.0 | 28.5 | 31.2 | 55.1 | 87.7 |
| pH 4.0 | 25.7 | 29.8 | 49.5 | 79.4 |
| pH 6.0 | 30.1 | 34.5 | 56.6 | 90.8 |

An exemplary embodiment of the invention relates to a composition comprising:

(I) a polymer formed from the polymerization of a monomer mixture comprising:

a) at least one silicone containing macromer selected from Formula III, IIIa, IV, and VIa above in optional combination with a monomer selected from:

b) at least one non-ionic monomer;

c) at least an acidic vinyl monomer;

d) at least one cationic vinyl monomer;

e) at least one associative vinyl monomer;

f) at least one semihydrophobic vinyl monomer;

g) a crosslinking monomer; and mixtures thereof; and mixtures thereof;

(II) an ingredient selected from water, a surfactant, a rheology modifier, and mixtures thereof; in optional combination with (III) one or more components selected from chelators, conditioners, diluents, fragrances, pigments, colorants, antioxidants, humectant skin and hair conditioners, lubricants, moisture barriers and emollients, neutralizers, opacifiers, pharmaceutical actives, preservatives, solvents, spreading aids, sunscreens, surfactants, conditioning polymers, vitamins, viscosity adjusters, viscosity modifiers, neutralizing agents, pH adjusting agents, and emulsifiers.

In another exemplary embodiment of the invention the silicone containing macromer is represented by the formulae:

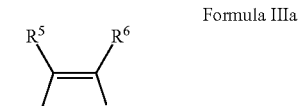
Formula IIIa

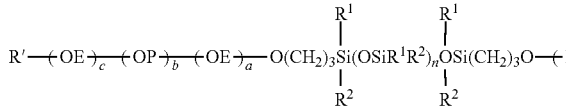

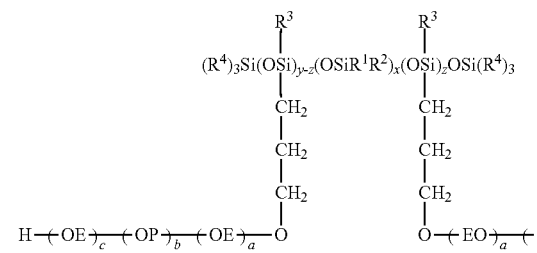

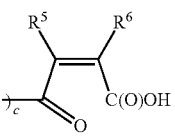
Formula IVa and isomers thereof, wherein R', R$^1$, R$^2$, R$^3$, R$^4$, R$^5$, R$^6$, EO(OE), PO(OP), a, b, c, n, x, y and z are as previously defined.

EXAMPLE 89

A washable hair molding wax is formulated with the ingredients set forth in Table 43.

TABLE 43

| | Ingredients | Wt. % |
|---|---|---|
| Part A | | |
| 1 | Butylene Glycol | 2.0 |
| 2 | Methyl Guceth-10 | 1.0 |
| 3 | D.I. Water | 52.31 |
| 4 | Disodium EDTA | 0.05 |
| 5 | Tocopheryl Acetate | 0.10 |
| Part B | | |
| 6 | Petrolatum | 12.0 |
| 7 | Isostearyl Hydroxy Stearate | 1.0 |
| 8 | Isoproyl Isostearate | 1.0 |
| 9 | Ethylhexyl Octanoate | 1.0 |
| 10 | Carnauba Wax | 4.0 |
| 11 | Microcrystalline Wax | 4.0 |
| 12 | Cetearyl Alcohol (and) Ceteareth-20 | 5.0 |
| 13 | Ceteareth-25 | 1.0 |
| Part C | | |
| 14 | Polymer of Example 35 (30 wt. % polymer solids) | 5.74 |
| 15 | D.I. water | 3.00 |
| Part D | | |
| 16 | Triethanolamine (99%) | 1.25 |
| 17 | Deionized Water | 5.00 |
| Part E | | |
| 18 | Fragrance (CA203005) | 0.05 |
| 19 | Methylisothiazolinone | 0.50 |

The ingredients of Part A are mixed and heated to 75° C. The ingredients of Part B are mixed and heated to a temperature ranging between 70° to 80° C. for a period of time until the ingredients are completely melted and a homogeneous mixture is obtained. Part A is slowly added to Part B with continuous mixing at 300 to 500 rpm while maintaining the temperature between 70° to 80° C. The Part A and B components are mixed until a uniform mixture is obtained. The Part AB mixture is allowed to cool to a temperature between 60° to 70° C. The Part C ingredients are combined and are added to the Part AB mixture while maintaining the temperature of the mixture between 60° to 70° C. The Part D ingredients are combined and are added to the Part ABC mixture with mixing until a uniform mixture is obtained. The Part ABCD mixture is allowed to cool to 50° C. whereupon the Part E ingredients are sequentially added to the mixture. The pH value of the composition is determined to be 7.4. The mixture is allowed to cool to a temperature between 40° to 45° C., poured into a container and allowed to solidify to give the hair wax product. The product has a glossy to off-white appearance. The product is allowed to rest for a 24 hour period at which point the Brookfield viscosity of the product is measured @ 40° C. @ 20 rpm using a no. 7 spindle and determined to be 150,000 mPa·s.

EXAMPLE 90

A clear ringing hair wax is formulated with the ingredients set forth in Table 44. The formulation provides a defined but pliable hair style and gives a non-greasy feel and look as well as a clear appearance when applied to the hair.

TABLE 44

| | Ingredients | Wt. % |
|---|---|---|
| Part A | | |
| 1 | D.I. Water | 62.22 |
| 2 | Cetereth-25 | 25.00 |
| 3 | Glycerin | 5.00 |
| 4 | D-Panthenol | 0.05 |
| 5 | Disodium EDTA | 0.03 |
| Part B | | |
| 6 | Polymer of Example 35 (30 wt. % polymer solids) | 3.00 |
| Part C | | |
| 7 | Sodium Hydroxide (18 wt. % aqueous solution) | 1.2-1.3 |
| Part D | | |
| 8 | PEG-12 Dimethicone | 3.00 |
| 9 | DMDM Hydantoin and Iodopropynyl Butylcarbamate | 0.40 |

Disodium EDTA is dissolved in glycerin and the remaining Part A ingredients are added to the solution. The Part A mixture is heated to 80° C. with mixing under slow agitation until a uniform mixture is obtained. The Part A mixture is cooled while under agitation to 60° C. Part B is added to Part A and mixed until homogeneous. The Part AB mixture is neutralized with Part C. Under moderate agitation, the ingredients of Part D are added and mixed until uniform. The ABCD composition is slowly agitated and allowed to cool. When the batch cools to a temperature of 40° to 45° C. it is poured into a wide mouth container and allowed to cool. The clear ringing hair wax product is allowed to rest for a 24 hour period at which point the Brookfield viscosity is measured @ 25° C. @ 20 rpm using a no. 7 spindle and determined to be 150,000 mPa·s.

EXAMPLE 91

Hair styling balms incorporating color, mica and/or glitter are formulated from the ingredients set forth in Table 45. The formulation promotes better washability, less build-up of residuals, longer lasting hold, and a non-greasy feel on the hair. Additionally, the formulation when applied to the hair exhibits excellent stiffness properties without the concomitant crunch and excessive waxy residues intrinsic to present day commercially available waxy hair products.

TABLE 45

| | Ingredients | Wt. % |
|---|---|---|
| Part A | | |
| 1 | PEG-40 Hydrogenated Castor Oil | 10 |
| 2 | Mineral Oil | 10 |
| 3 | Neopentyl Glycol Dioctanoate | — |
| 4 | PEG-90M | — |
| 5 | Oleth-10 | 10 |
| 6 | Oleth-20 | 11 |
| 7 | Cetearyl Alcohol | 2 |
| 8 | Propyl Paraben | 0.2 |
| Part B | | |
| 9 | D.I. Water | q.s. to 100 wt. % |
| 10 | Glycerin | 7 |
| 11 | Propylene Glycol | 5 |
| 12 | Methyl Paraben | 0.2 |
| Part C | | |
| 13 | Polymer of Example 35 (30 wt. % polymer solids) | 5.0 |
| Part D | | |
| 14 | Sodium Hydroxide | q.s. to pH 7 |
| Part E | | |
| 15 | Mica | |
| 16 | Color (FDC Blue No. 1) | 0.3 |
| 17 | D.I. Water | 5.0 |
| Part F | | |
| 18 | Glitter | 0.3 |
| 19 | Fragrance | 0.5 |

The ingredients of Part A are mixed and heated to about 75° C. The ingredients of Part B are mixed and heated to a temperature ranging between 70° to 80° C. for a period of time until the ingredients are completely melted and a homogeneous mixture is obtained. Part B is slowly added to Part A with continuous mixing at 300 to 500 rpm while maintaining the temperature between 70° to 80° C. The Part A and B components are mixed until a uniform mixture is obtained. The Part AB mixture is allowed to cool to a temperature between 60° to 70° C. The Part C ingredient is added to the Part AB mixture while maintaining the temperature of the mixture between 60° to 70° C. The Part D ingredient is added to the Part ABC mixture with mixing until a uniform blend is obtained. The Part ABCD blend is maintained at about 60° C. whereupon the Part E and Part F ingredients are sequentially added with mixing to achieve a homogeneous blend. The pH value of the composition is determined to be 7.3. The composition is allowed to cool to a temperature between 40° to 45° C., poured into a container and allowed to solidify to give the hair wax product.

What is claimed is:

1. A composition comprising:

A) A polymer polymerized from a free radically polymerizable monomer composition comprising at least one dimethicone copolyol macromer selected from formula III and IV:

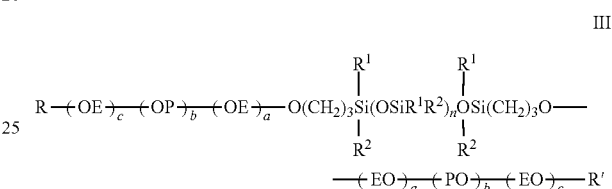

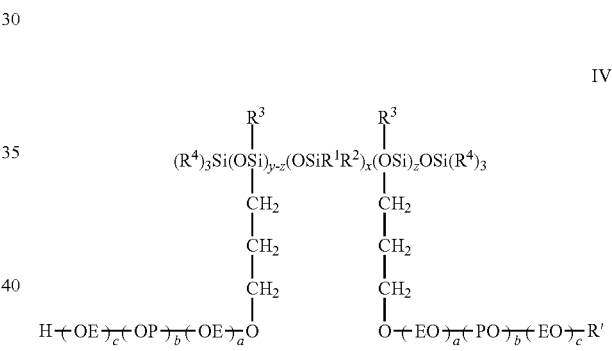

wherein in formula III R and R' independently represent hydrogen or a cyclic anhydride residue, subject to the proviso that R and R' do not both represent hydrogen at the same time, $R^1$ and $R^2$ independently represent a radical selected from $C_1$ to $C_{30}$ alkyl, $C_1$ to $C_{20}$ halo substituted alkyl, $C_3$ to $C_8$ cycloalkyl, $C_6$ to $C_{14}$ aryl, and $C_2$ to $C_{20}$ alkenyl, E represents a divalent ethylene radical, P independently represents a divalent propylene radical, a, b, and c are independently 0 to 100; and n is 0 to 200, E taken together with the oxygen atom to which is attached represents an ethylene oxide residue (EO or OE) and P taken together with the oxygen atom to which it is attached represents a propylene oxide residue (PO or OP), wherein EO and PO residues can be arranged in a random, non-random, and blocky order;

wherein in formula IV R', $R^1$ and $R^2$, E, P, EO, OE, PO, OP, a, b, and c are as defined above, $R^3$ represents a radical selected from $C_1$ to $C_{30}$ alkyl, $C_1$ to $C_{20}$ halo substituted alkyl, $C_3$ to $C_8$ cycloalkyl, $C_6$ to $C_{14}$ aryl, and $C_2$ to $C_{20}$ alkenyl, $R^4$ represents a radical selected from $C_1$ to $C_{30}$ alkyl, $C_6$ to $C_{14}$ aryl, and $C_2$ to $C_{20}$ alkenyl, x is 0 to 200, y is 1 to 200, z<y; and wherein said cyclic anhydride residue in formula III and IV is represented by the formula:

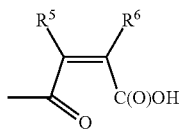

wherein $R^5$ and $R^6$ are independently selected from hydrogen and methyl, subject to the proviso that $R^5$ and $R^6$ do not both represent methyl at the same time;

B) at least one solvent or diluent; and optionally

C) one or more ingredients selected from a surfactant(s), a rheology modifier(s), a viscosity adjuster(s), an emollients, a humectant(s), a lubricant(s), an emulsifier(s), a conditioner(s), a structurant(s), a fixative(s), an opacifier(s), a spreading aid(s), an antioxidant(s), a sun screen agent, an antiperspirant agent(s), a pharmaceutical active(s), a vitamin(s), a preservative(s), an antimicrobial agent(s), an antifungal agent(s), a botanical extract(s), an antidandruff agent(s), an abrasive(s), a chelating agent(s), a pH adjusting agent(s), a neutralizing agent(s), a fragrance(s), a pigment(s), a colorant(s), a pearlescent agents(s), a propellant(s), an oxidizing agent(s), an antistatic agent(s), and combinations thereof.

2. A composition of claim 1 wherein said monomer composition further comprises at least one monomer selected from:
 a) at least one non-ionic vinyl monomer;
 b) optionally at least one acidic vinyl monomer;
 c) optionally at least one cationic vinyl monomer;
 d) optionally at least one associative vinyl monomer;
 e) optionally at least one semihydrophobic vinyl monomer;
 f) optionally at least one crosslinking monomer; and mixtures thereof.

3. A composition of claim 2 wherein said non-ionic vinyl monomer is selected from at least one monomer represented by the formula:

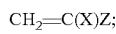

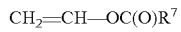

wherein, X is H or methyl; and Z is $-C(O)OR^8$, $-C(O)NH_2$, $-C(O)NHR^8$, $-C(O)N(R^8)_2$, $-C_6H_4R^8$, $-C_6H_4OR^8$, $-C_6H_4Cl$, $-C_6H_{11}$, $-C_6H_7(R^8)(R^8)(R^8)$, $-CN$, $-NHC(O)CH_3$, $-NHC(O)H$, N-(2-pyrrolidonyl), N-caprolactamyl, $-C(O)NHC(CH_3)_3$, $-C(O)NHCH_2CH_2-N$-ethyleneurea, $-Si(R^7)_3$, $-C(O)O(CH_2)_xSi(R^7)_3$, $-C(O)NH(CH_2)_xSi(R^7)_3$, or $-(CH_2)_xSi(R^7)_3$; x is an integer ranging from about 1 to about 6; $R^7$ independently represents linear and branched $C_1$ to $C_{18}$ alkyl; $R^8$ independently represents linear and branched $C_1$ to $C_{30}$ alkyl, hydroxy substituted $C_2$ to $C_{30}$ alkyl, and halogen substituted $C_1$ to $C_{30}$ alkyl.

4. A composition of claim 2 wherein said acidic vinyl monomer contains at least one acidic group selected from a carboxylic acid group and salts thereof, a sulfonic acid group and salts thereof, and a phosphonic acid group and salts thereof.

5. A composition of claim 4 wherein said acidic vinyl monomer is selected from acrylic acid, methacrylic acid, itaconic acid, citraconic acid, maleic acid, fumaric acid, crotonic acid, aconitic acid, $C_1$ to $C_{18}$ alkyl monoesters of maleic, fumaric, itaconic, or aconitic acid, anhydrides of dicarboxylic acids, vinyl sulfonic acid, 2-sulfoethyl methacrylate, styrene sulfonic acid, 2-acrylamido-2-methylpropane sulfonic acid, allyloxybenzene sulfonic acid, vinyl. phosphonic acid, allyl phosphonic acid, 3-acrylamidopropyl phosphonic acid; and salts thereof;
and mixtures thereof.

6. A composition of claim 2 wherein said cationic vinyl monomer is selected from mono-($C_1$ to $C_4$)alkylamino($C_1$ to $C_8$)alkyl (meth)acrylate, a di-($C_1$ to $C_4$)alkylamino($C_1$ to $C_8$)alkyl (meth)acrylate, a mono-($C_1$ to $C_4$)alkylamino($C_1$ to $C_8$)alkyl (meth)acrylamide, a di-($C_1$ to $C_4$)alkylamino($C_1$ to $C_8$)alkyl (meth)acrylamide, a nitrogen-containing heterocyclic (meth)acrylamide, a nitrogen-containing heterocyclic (meth)acrylate;
and salts thereof; and mixtures thereof.

7. A composition of claim 6 wherein said cationic vinyl monomer is selected from 2-(N,N-dimethylamino)ethyl (meth)acrylate, 3-(N,N-dimethylamino)propyl (meth)acrylate, 4-(N,N-dimethylamino)butyl (meth)acrylate, (N,N-dimethylamino)-t-butyl(meth)acrylate, 2-tert-butylamino)ethyl methacrylate, 2-(N,N-diethylamino)ethyl (meth)acrylate, 3-(N,N -diethylamino)propyl(meth)acrylate, 2-N,N-dimethylamino)neopentyl acrylate, 4-N,N -diethylamino)butyl(meth)acrylate, 2-(N,N-dipropylamino)ethyl (meth)acrylate, 3-N,N -dipropylamino)propyl (meth)acrylate, 4-N,N-dipropylamino)butyl (meth)acrylate, 3-(N,N -dimethylamino)propyl (meth)acrylate, 2-(4-morpholinyl) ethyl methacrylate, 2-(4-morpholinyl)ethyl acrylate, N'-(2-N,N-dimethylamino)ethyl methacrylamide, 2-N,N-dimethylamino)propyl methacrylamide, N'-3-N,N-dimethylamino) propyl (meth)acrylamide, N-(2-pyridyl)acrylamide, N-2-imidazoyl)(meth)acrylamide, N-(4-morpholinyl) (meth) acrylamide, N-4-morpholinyl)acrylamide, 2-vinyl pyridine, 4-vinyl pyridine, N-vinyl-2-methylimidazole, N-vinylimidazole, N-vinyl-4-methylimidazole, and N-vinyloxazolidone; and salts thereof; and mixtures thereof.

8. A composition of claim 5 wherein said cationic vinyl monomer is selected from 3-trimethylammonium propyl methacrylamide chloride, 3-trimethylammonium propyl acrylamide chloride, quaternized N,N-dimethylaminoethyl methacrylate with $C_1$ to $C_{30}$ alkyl sulphate, quaternized N,N-dimethylaminoethyl methacrylate with methylchloride, quaternized vinyl imidazole, methacryloyl ethyl betaine, and methacryloyl N-oxide.

9. A composition of claim 2 wherein said associative vinyl monomer is selected from at least one monomer represented by the formula:

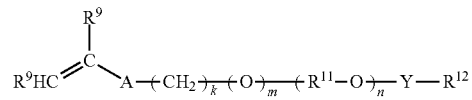

wherein, each $R^9$ is independently H, $C_1$ to $C_{30}$ alkyl, $-C(O)OH$, or $-C(O)OR^{10}$; $R^{10}$ is $C_1$ to $C_{30}$ alkyl; A is $-CH_2C(O)O-$, $-C(O)O-$, $-O-$, $-CH_2O-$, $-NHC(O)NH-$, $-C(O)NH-$, $-Ar-CE_2)_z-NHC(O)O-$, $-Ar-(CE_2)_z-NHC(O)NH-$, or $-CH_2CH_2NHC(O)-$; Ar is a divalent aryl; E is H or methyl; z is 0 or 1; k is an integer in the range of 0 to about 30, and m is 0 or 1, with the proviso that when k is 0, m is 0, and when k is in the range of 1 to about 30, m is 1; $(R^{11}-O)_n$ represents a polyoxyalkylene moiety of $C_2$ to $C_4$ oxyalkylene units, wherein $R^{11}$ is $C_2H_4$, $C_3H_6$, $C_4H_8$, or a mixture thereof, and n is an integer in the range of about 5 to about 250; Y is $-R^{11}O-$, $-R^{11}NH-$, $-C(O)-$, $-C(O)NH-$, $-R^{11}NHC(O)NH-$, or $-C(O)NHC(O)-$; and $R^{12}$ is a substituted or unsubstituted alkyl selected from a $C_8$ to $C_{40}$ linear alkyl, a $C_8$ to $C_{40}$ branched alkyl, a $C_8$ to $C_{40}$ carbocyclic alkyl, a $C_2$ to $C_{40}$ alkyl-substituted phenyl, an aryl-substituted $C_2$ to $C_{40}$ alkyl, and a $C_8$ to $C_{80}$ complex ester; wherein $R^{11}$ and $R^{12}$ optionally includes one or more substituents selected from hydroxyl, alkoxyl, and halogen.

10. A composition of claim 9 wherein said associative vinyl monomer is selected from cetyl polyethoxylated methacrylate, cetearyl polyethoxylated methacrylate, stearyl polyethoxylated (meth)acrylate, arachidyl polyethoxylated (meth)acrylate, behenyl polyethoxylated methacrylate, lauryl polyethoxylated methacrylate, cerotyl polyethoxylated (meth)acrylate, montanyl polyethoxylated (meth)acrylate, melissyl polyethoxylated (meth)acrylate, lacceryl polyethoxylated (meth)acrylate, tristyryl phenolpolyethoxylated methacrylate, hydrogenated castor oil polyethoxylated methacrylate, canola polyethoxylated (meth)acrylate, and cholesterol polyethoxylated methacrylate, wherein the polyethoxylated portion of the monomer contains from about 5 to about 100 ethylene oxide repeating units.

11. A composition of claim 2 wherein said semihydrophobic vinyl monomer is selected from at least one monomer represented by the formula:

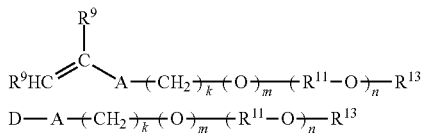

wherein $R^9$ is independently H, $C_1$ to $C_{30}$ alkyl, —C(O)OH, or —C(O)OR$^{10}$; $R^{10}$ is $C_1$ to $C_{30}$ alkyl; A is —CH$_2$C(O)O—, —C(O)O—, —O—, —CH$_2$O—, —NHC(O)NH—, —C(O)NH—, —Ar—CE$_2$)$_z$—NHC(O)O—, —Ar—(CE$_2$)$_z$—NHC(O)NH—, or —CH$_2$CH$_2$NHC(O)—; Ar is a divalent aryl; E is H or methyl; z is 0 or 1; k is an integer in the range of 0 to about 30, and m is 0 or 1, with the proviso that when k is 0, m is 0, and when k is in the range of 1 to about 30, m is 1; (R$^{11}$—O)$_n$ represents a polyoxyalkylene moiety of $C_2$ to $C_4$ oxyalkylene units, wherein $R^{11}$ is $C_2H_4$, $C_3H_6$, $C_4H_8$, or a mixture thereof, and n is an integer in the range of about 5 to about 250; Y is —R$^{11}$O—, —R$^{11}$NH—, —C(O)—, —C(O)NH—, —R$^{11}$NHC(O)NH—, or —C(O)NHC(O)—; wherein $R^{11}$ optionally includes one or more substituents selected from hydroxyl, alkoxyl, and halogen; D is a $C_8$ to $C_{30}$ unsaturated alkyl, or a carboxy-substituted $C_8$ to $C_{30}$ unsaturated alkyl; and $R^{13}$ is H or $C_1$ to $C_4$ alkyl.

12. A composition of claim 11 wherein said semihydrophobic vinyl monomer is represented by at least one monomer of the formulae:

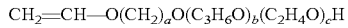

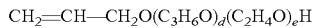

wherein a is an integer of 2, 3, or 4; b is an integer in the range of 1 to about 10; c is an integer in the range of about 5 to about 50; d is an integer in the range of 1 to about 10; and e is an integer in the range of about 5 to about 50.

13. A composition of claim 1 wherein said monomer composition comprises 0 to 5 weight percent based on the weight of the total monomers of a crosslinking monomer.

14. A composition of claim 1 wherein said monomer composition comprises at least 0.01 percent by weight based on the total monomer weight of a chain transfer agent.

15. A composition of claim 1 wherein said composition comprises an ingredient selected from a structurant(s), a humectant(s), an emollient(s), a fixative(s), a surfactant(s), a rheology modifier(s), a neutralizer(s), a conditioner, and combinations thereof.

16. The composition of claim 15 wherein said composition further comprises an ingredient selected form an auxiliary solvent, a propellant, and combinations thereof.

17. The composition of claim 16 wherein said composition is in the form of a cream, pomade, gel, paste, ointment, spray, lotion, spritz, and mousse.

18. A hair care composition comprising:
A) A polymer polymerized from a free radically polymerizable monomer composition comprising:
at least one dimethicone copolyol macromer selected from formula III and IV:

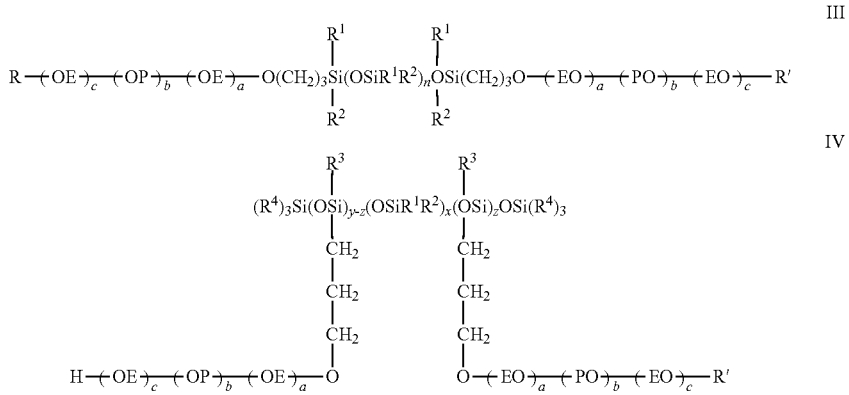

wherein in formula III R and R' independently represent hydrogen or a cyclic anhydride residue, subject to the proviso that R and R' do not both represent hydrogen at the same time, $R^1$ and $R^2$ independently represent a radical selected from $C_1$ to $C_{30}$ alkyl, $C_1$ to $C_{20}$ halo substituted alkyl, $C_3$ to $C_8$ cycloalkyl, $C_6$ to $C_{14}$ aryl, and $C_2$ to $C_{20}$ alkenyl, E represents a divalent ethylene radical, P independently represents a divalent propylene radical, a, b, and c are independently 0 to 100; and n is 0 to 200, E taken together with the oxygen atom to which is attached represents an ethylene oxide residue (EO or OE) and P taken together with the oxygen atom to which it is attached represents a propylene oxide residue (PO or OP), wherein EO and PO residues can be arranged in a random, non-random, and blocky order;

wherein in formula IV R', $R^1$ and $R^2$, E, P, EO, OE, PO, OP, a, b, and c are as defined above, $R^3$ represents a radical selected from $C_1$ to $C_{30}$ alkyl, $C_1$ to $C_{20}$ halo substituted alkyl, $C_3$ to $C_8$ cycloalkyl, $C_6$ to $C_{14}$ aryl, and $C_2$ to $C_{20}$ alkenyl, $R^4$ represents a radical selected from $C_1$ to $C_{30}$ alkyl, $C_6$ to $C_{14}$ aryl, and $C_2$ to $C_{20}$ alkenyl, x is 0 to 200, y is 1 to 200, z<y; and wherein said cyclic anhydride residue in formulae III and IV is represented by the formula:

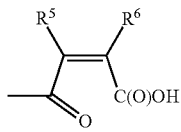

wherein $R^5$ and $R^6$ are independently selected from hydrogen and methyl, subject to the proviso that $R^5$ and $R^6$ do not both represent methyl at the same time;
  (ii) at least one acidic vinyl monomer;
  (iii) at least one non-ionic vinyl monomer;
  (iv) optionally at least one associative vinyl monomer; and
  (v) optionally at least one crosslinking monomer;
B) at least one solvent or diluent;
C) at least one ingredient selected from the group of a structurant, a rheology modifier, a conditioner, a surfactant, an emollient, a humectant, a neutralizer, a pH adjusting agent, a chelating agent, an auxiliary fixative, a preservative, a fragrance, a pearlizing agent, and combinations thereof.

19. A hair care composition of claim 18 wherein said structurant is selected from at least one wax, at least one fatty alcohol and esters thereof, at least one fatty acid and esters thereof, petrolatum, and combinations thereof.

20. A hair care composition of claim 18 wherein said composition is in the form of a cream, gel, pomade, paste, mousse, spray, or spritz.

21. A hair care composition of claim 18 wherein said acidic vinyl monomer is selected from acrylic acid, methacrylic acid, itaconic acid, citraconic acid, maleic acid, fumaric acid, crotonic acid, aconitic acid, $C_1$ to $C_{18}$ alkyl monoesters of maleic, fumaric, itaconic, or aconitic acid, anhydrides of dicarboxylic acids, vinyl sulfonic acid, 2-sulfoethyl methacrylate, styrene sulfonic acid, 2-acrylamido-2-methylpropane sulfonic acid, allyloxybenzene sulfonic acid, vinyl phosphonic acid, allyl phosphonic acid, 3-acrylamidopropyl phosphonic acid; and
  salts thereof; and mixtures thereof.

22. A hair care composition of claim 18 wherein said nonionic vinyl monomer is selected from $C_1$ to $C_{30}$ alkyl (meth)acrylates, cyclohexyl(meth)acrylates, 3,3,5-trimethylcyclohexyl(meth)acrylates, $C_1$ to $C_{30}$ alkyl (meth)acrylamides, styrene, vinyl toluene butyl styrene, isopropyl styrene, p-chloro styrene, vinyl acetate, vinyl butyrate, vinyl caprolate, vinyl pivalate, vinyl neodecanoate, methacrylonitrile, acrylonitrile, trimethylvinylsilane, dimethylethylvinylsilane, allyldimethylphenylsilane, allyltrimethylsilane, 3-acrylamidopropyltrimethylsilane, 3-trimethylsilylpropyl methacrylate, 2-hydroxyethyl methacrylate (HEMA), 2-hydroxyethyl acrylate (2-HEA), 3-hydroxypropyl acrylate, glycerol mono (meth)acrylate; tris(hydroxymethyl)ethane mono(meth) acrylate, pentaerythritol mono(meth)acrylate, N-hydroxymethyl (meth)acrylamide, 2-hydroxyethyl (meth)acrylamide, 3-hydroxypropyl (meth)acrylamide, (meth)acrylamide, t-octyl(meth)acrylamide, N-(2,3-dihydroxypropyl) acrylamide, t-butyl(meth)acrylamide, N-vinyl caprolactam, N-vinyl pyrrolidone, methacrylamidoethyl-N-ethyleneurea, methoxyethyl (meth)acrylate, 2-(2-ethoxyethoxy)ethyl (meth)acrylate; and mixtures thereof.

23. A hair care composition of claim 18 wherein said associative vinyl monomer is selected from at least one monomer represented by the formula:

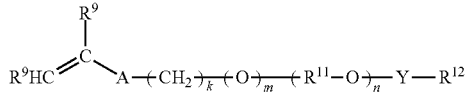

wherein, each $R^9$ is independently H, $C_1$ to $C_{30}$ alkyl, —C(O)OH, or —C(O)O$R^{10}$; $R^{10}$ is $C_1$ to $C_{30}$ alkyl; A is —CH$_2$C(O)O—, —C(O)O—, —O—, —CH$_2$O—, —NHC(O)NH—, —C(O)NH—, —Ar—CE$_2)_z$—NHC (O)O—, —Ar—(CE$_2)_z$—NHC(O)NH—, or —CH$_2$CH$_2$NHC(O)—; Ar is a divalent aryl; E is H or methyl; z is 0 or 1; k is an integer in the range of 0 to about 30, and m is 0 or 1, with the proviso that when k is 0, m is 0, and when k is in the range of 1 to about 30, m is 1; ($R^{11}$-0)$_n$ represents a polyoxyalkylene moiety of $C_2$ to $C_4$ oxyalkylene units, wherein $R^{11}$ is $C_2H_4$, $C_3H_6$, $C_4H_8$, or a mixture thereof, and n is an integer in the range of about 5 to about 250; Y is —$R^{11}$O—, —$R^{11}$NH—, —C(O)—, —C(O)NH—, —$R^{11}$NHC(O) NH—, or
—C(O)NHC(O)—; and $R^{12}$ is a substituted or unsubstituted alkyl selected from a $C_8$ to $C_{40}$ linear alkyl, a $C_8$ to $C_{40}$ branched alkyl, a $C_8$ to $C_{40}$ carbocyclic alkyl, a $C_2$ to $C_{40}$ alkyl-substituted phenyl, an aryl-substituted $C_2$ to $C_{40}$ alkyl, and a $C_8$ to $C_{80}$ complex ester; wherein $R^{11}$ and $R^{12}$ optionally includes one or more substituents selected from hydroxyl, alkoxyl, and halogen.

24. A composition of claim 23 wherein said associative vinyl monomer is selected from cetyl polyethoxylated methacrylate, cetearyl polyethoxylated methacrylate, stearyl polyethoxylated (meth)acrylate, arachidyl polyethoxylated (meth)acrylate, behenyl polyethoxylated methacrylate, lauryl polyethoxylated methacrylate, cerotyl polyethoxylated (meth)acrylate, montanyl polyethoxylated (meth)acrylate, melissyl polyethoxylated (meth)acrylate, lacceryl polyethoxylated (meth)acrylate, tristyryl phenolpolyethoxylated methacrylate, hydrogenated castor oil polyethoxylated methacrylate, canola polyethoxylated (meth)acrylate, and cholesterol polyethoxylated methacrylate, wherein the polyethoxylated portion of the monomer contains from about 5 to about 100 ethylene oxide repeating units.

* * * * *